(12) United States Patent
Shalwitz et al.

(10) Patent No.: US 9,278,930 B2
(45) Date of Patent: *Mar. 8, 2016

(54) METHODS FOR INCREASING THE STABILIZATION OF HYPOXIA INDUCIBLE FACTOR-α

(71) Applicant: Aerpio Therapeutics Inc., Cincinnati, OH (US)

(72) Inventors: Robert Shalwitz, Bexley, OH (US); Joseph H. Gardner, Cincinnati, OH (US)

(73) Assignee: AERPIO THERAPEUTICS, INC., Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/628,261

(22) Filed: Feb. 22, 2015

(65) Prior Publication Data

US 2015/0157617 A1 Jun. 11, 2015

Related U.S. Application Data

(60) Continuation of application No. 14/465,027, filed on Aug. 21, 2014, now Pat. No. 8,999,971, which is a continuation of application No. 13/770,135, filed on Feb. 19, 2013, now Pat. No. 8,883,774, which is a division of application No. 12/940,883, filed on Nov. 5, 2010, now Pat. No. 8,778,412.

(60) Provisional application No. 61/258,914, filed on Nov. 6, 2009, provisional application No. 61/258,918, filed on Nov. 6, 2009.

(51) Int. Cl.

| | |
|---|---|
| *A61K 31/4412* | (2006.01) |
| *C07D 211/96* | (2006.01) |
| *A61K 31/44* | (2006.01) |
| *A61K 31/4439* | (2006.01) |
| *A61K 31/4545* | (2006.01) |
| *A61K 31/496* | (2006.01) |
| *A61K 31/501* | (2006.01) |
| *A61K 31/5377* | (2006.01) |
| *A61K 31/541* | (2006.01) |
| *A61K 31/55* | (2006.01) |
| *C07D 213/02* | (2006.01) |
| *C07D 213/69* | (2006.01) |
| *C07D 401/06* | (2006.01) |
| *C07D 401/14* | (2006.01) |
| *C07D 417/06* | (2006.01) |
| *C07D 491/113* | (2006.01) |
| *A61K 31/4427* | (2006.01) |
| *A61K 31/444* | (2006.01) |
| *A61K 45/06* | (2006.01) |
| *C07D 211/86* | (2006.01) |

(52) U.S. Cl.
CPC .............. *C07D 211/96* (2013.01); *A61K 31/44* (2013.01); *A61K 31/444* (2013.01); *A61K 31/4412* (2013.01); *A61K 31/4427* (2013.01); *A61K 31/4439* (2013.01); *A61K 31/4545* (2013.01); *A61K 31/496* (2013.01); *A61K 31/501* (2013.01); *A61K 31/5377* (2013.01); *A61K 31/541* (2013.01); *A61K 31/55* (2013.01); *A61K 45/06* (2013.01); *C07D 211/86* (2013.01); *C07D 213/02* (2013.01); *C07D 213/69* (2013.01); *C07D 401/06* (2013.01); *C07D 401/14* (2013.01); *C07D 417/06* (2013.01); *C07D 491/113* (2013.01)

(58) Field of Classification Search
CPC ............ C07D 213/02; C07D 491/113; C07D 417/06; C07D 401/14; C07D 213/69; C07D 401/06; C07D 211/96; C07D 211/86; A61K 31/44; A61K 31/4439; A61K 31/496; A61K 31/4545; A61K 31/541; A61K 31/501; A61K 31/5377; A61K 31/4412; A61K 31/55; A61K 31/4427; A61K 31/444; A61K 45/06

See application file for complete search history.

(56) References Cited

U.S. PATENT DOCUMENTS

| | | | |
|---|---|---|---|
| 6,566,088 | B1 | 5/2003 | Knight et al. |
| 6,589,758 | B1 | 7/2003 | Zhu |
| 6,930,117 | B2 | 8/2005 | Warshakoon et al. |
| 6,946,479 | B2 | 9/2005 | Warshakoon et al. |
| 7,183,287 | B2 | 2/2007 | Durley |

(Continued)

FOREIGN PATENT DOCUMENTS

| | | | | |
|---|---|---|---|---|
| IN | WO2005/051933 | * | 6/2005 | ........... C07D 263/20 |
| WO | WO 96/22021 A1 | | 7/1996 | |

(Continued)

OTHER PUBLICATIONS

B. Zhou, et al, Therapeutic Neovascularization for Peripheral Arterial Diseases: Advances and Perspectives, 22 Histol. Histopathol. 677 (2007).*
Ardelt, et al. Estradiol regulates angiopoietin-1 mRNA expression through estrogen receptor-alpha in a rodent experimental stroke model. Stroke. Feb. 2005;36(2):337-41. Epub Jan. 6, 2005.
Balfour R., "Bacteria in Crohn's disease: mechanisms of inflammation and therapeutic implications," J. Clin. (2007) Jul:41(6);S37-S43.
Bento C.F., "Regulation of hypoxia-inducible factor 1 and the loss of the cellular response to hypoxia in diabetes," Diabetologia (2011) 54:1946-1956.

(Continued)

*Primary Examiner* — Sean Basquill
(74) *Attorney, Agent, or Firm* — Wilson Sonsini Goodrich & Rosati

(57) ABSTRACT

Disclosed herein are methods for controlling the activity of hypoxia-inducible transcription factor 1-alpha (HIF-1α) and diseases, conditions, or syndromes related thereto, inter alia, Peripheral Vascular Disease (PVD), Coronary Artery Disease (CAD), heart failure, ischemia, and anemia. Further disclosed are pharmaceutical compositions comprising HIF-1α prolyl hydroxylase inhibitors useful in treating diseases, conditions, and/or syndromes related thereto the activity of HIF-1α.

13 Claims, 11 Drawing Sheets

(56) References Cited

U.S. PATENT DOCUMENTS

| | | | |
|---|---|---|---|
| 7,247,632 B2 | 7/2007 | Warshokoon et al. | |
| 7,247,648 B2 | 7/2007 | Warshokoon et al. | |
| 7,790,748 B2 | 9/2010 | Warshakoon et al. | |
| 7,811,595 B2 | 10/2010 | Kawamoto et al. | |
| 8,133,894 B2 | 3/2012 | Warshakoon et al. | |
| 8,309,537 B2 | 11/2012 | Gardner et al. | |
| 2002/0192737 A1 | 12/2002 | Kaelin, Jr. et al. | |
| 2003/0176317 A1 | 9/2003 | Guenzler-Pukall et al. | |
| 2004/0097560 A1* | 5/2004 | Warshakoon | C07D 213/69 514/348 |
| 2004/0146964 A1 | 7/2004 | Maxwell et al. | |
| 2006/0276477 A1 | 12/2006 | Klaus et al. | |
| 2007/0154482 A1 | 7/2007 | Sukhatme et al. | |
| 2007/0213335 A1 | 9/2007 | Fitch et al. | |
| 2007/0249550 A1 | 10/2007 | Sitkovsky | |
| 2008/0213404 A1 | 9/2008 | Johnson et al. | |
| 2008/0300262 A1 | 12/2008 | Snutch | |
| 2009/0082357 A1 | 3/2009 | Fitch et al. | |
| 2009/0093483 A1 | 4/2009 | Allen et al. | |

FOREIGN PATENT DOCUMENTS

| | | |
|---|---|---|
| WO | WO 97/41103 A2 | 11/1997 |
| WO | WO 02/074980 A2 | 9/2002 |
| WO | WO 02/074981 A2 | 9/2002 |
| WO | WO 03/028663 A2 | 4/2003 |
| WO | WO 2004/035812 A2 | 4/2004 |
| WO | WO 2005/007192 A2 | 1/2005 |
| WO | WO 2005/051933 A1 | 6/2005 |
| WO | WO 2005/118836 A2 | 12/2005 |
| WO | WO 2006/114213 A1 | 11/2006 |
| WO | WO 2007/038571 A2 | 4/2007 |
| WO | WO 2007/047194 A2 | 4/2007 |
| WO | WO 2007/070359 A2 | 6/2007 |
| WO | WO 2007/082899 A1 | 7/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |
| WO | WO 2008/144266 A1 | 11/2008 |
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |
| WO | WO 2009/073497 A2 | 6/2009 |
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |

OTHER PUBLICATIONS

Folkman. Tumor angiogenesis. The Molecular Basis of Cancer (eds. Mendelsohn, J., Howley, P. M., Israel, M. A. & Liotta, L. A.) Ch. 10. 206-232 (1995).

Geronemus, et al. Wound healing. The effects of topical antimicrobial agents. Arch Dermatol. Nov. 1979;115(11):1311-4.

Gorres et al., "Prolyl 4-hydroxylase," Crit Rev Biochem Mol Biol. Apr. 2010; 45(2): 106-124.

Kaelin, "Proline Hydroxylation and Gene Expression," *Annu. Rev. Biochem.*, 74:115125 (2005).

Krantz, "Erythropoietin," *Blood*, 77:419-434 (1991).

Lee et al., "Structure of Human FIH-1 Reveals a Unique Active Site Pocket and Interaction Sites for HIF-1 and von Hippel Lindau," *JBC*, 278;7558-7563 (2003).

Lewis et al., "Macrophage responses to hypoxia: relevance to disease mechanisms," J. Leukocyte Biology, 66: (1999).

McDonough et al., "Cellular Oxygen Sensing: Crystal Structure of Hypoxia-Inducible Factor Prolyl Hydroxylase (PHD2)," *PNAS*, 103(26):9814-9819 (2006).

Murdoch et al., "Hypoxia Regulates Macrophage Functions in Inflammation," J. Immunology, 2005, 175: 6257-6263.

Notice of allowance dated Feb. 18, 2015 for U.S. Appl. No. 14/465,027.

Notice of allowance dated Apr. 10, 2015 for U.S. Appl. No. 13/768,308.

Office action dated Jan. 29, 2015 for U.S. Appl. No. 13/768,308.

Okumura Y.M. et al., "A new pharmacological agent (AKB-4924) stabilized hypoxia inducible factor-1 (HIF-1) and increases skin innate defenses against bacterial infection," J. Mo. Med.; Feb. 28, 2013.

Ostergaard et al., "Hypoxia Inducible Factor and Hypoxia-mediated Pulmonary Hypertension," PVRI Review; 3(1); 2011, 5-11.

Patani, et al. Bioisosterism: A Rational Approach in Drug Design. Chem Rev. Dec. 19, 1996;96(8):3147-3176.

Peyssonnaux, et al. HIF-1alpha expression regulates the bactericidal capacity of phagocytes. J Clin Invest. Jul. 2005;115(7):1806-15.

Schafer S.T. et al., "Hypoxia-inducible Factor and Target Gene Expression Are Decreased in Patients with Sepsis," Anesthesiology 2013; 118:1 1426-36.

Semenza et al., "Transcriptional Regulation of Genes Encoding Glycolytic Enzymes by Hypoxia-Inducible Factor 1," *J Biol. Chem.*, 269:23757-23763 (1994).

Semenza, "Regulation of Erythropoietin Porduction: New Insights into Molecular Mechanisms of Oxygen Homeostasis," *Hematol. Oncol. Clin. North Am.*, 8:863-884 (1994).

Semenza, "Signal Transduction to Hypoxia-inducible Factor 1," *Biochem. Pharmacol*, 64:993-998 (2002).

Stadelmann, et al. Impediments to wound healing. Am J Surg. Aug. 1998;176(2A.Suppl):39S-47S.

Vincent et al., "Angiogenesis is Induced in a Rabbit Model of Hindlimb Ischemia by Naked DNA Encoding an HIF-la/VP16 Hybrid Transcription Factor," *Circulation*, 102:2255-2261 (2000).

Wanner et al., "Epolones induce erythropoietin expression via hypoxia-inducible factor-1a activation," Blood, 96(4): 1558-1565 (2000).

Warnecke et al., "Activation of the Hypoxia-Inducible Factor Pathway and Stimulation of Angiogenesis by Application of Prolyl Hydroxylase Inhibitors," *FASEB Journal*, 17:1186-1188 (2003).

Wright, et al. Activation of the prolyl hydroxylase oxygen-sensor results in induction of GLUT1, heme oxygenase-1, and nitric-oxide synthase proteins and confers protection from metabolic inhibition to cardiomyocytes. J Biol Chem. May 30, 2003;278(22):20235-9. Epub Mar. 20, 2003.

Zhao S. et al., "Hypoxia Inducible Factor Stabilization As a Novel Strategy to Treat Anemia," Current Medicinal (2013), 20(1); pp. 1-15.

* cited by examiner

METHODS FOR INCREASING THE STABILIZATION OF HYPOXIA INDUCIBLE FACTOR-α

PRIORITY

This application is a Continuation application of U.S. application Ser. No. 14/465,027, filed Aug. 21, 2014, which is a Continuation Application of U.S. application Ser. No. 13/770,135, filed Feb. 19, 2013, now U.S. Pat. No. 8,883,774, issued Nov. 11, 2014, which is a Divisional Application of U.S. application Ser. No. 12/940,883, filed Nov. 5, 2010, now U.S. Pat. No. 8,778,142, issued Jul. 15, 2014, which claims the benefit of Provisional Application Ser. No. 61/258,914 and Provisional Application Ser. No. 61/258,918 that were both filed on Nov. 6, 2009, all of which Applications are incorporated herein by reference in their entirety.

FIELD OF THE DISCLOSURE

Disclosed herein are prolyl hydroxylase inhibitors that can stabilize hypoxia inducible factor-1 alpha (HIF-1α), as well as hypoxia inducible factor-2 alpha (HIF-2α). Also disclosed herein are pharmaceutical compositions comprising one or more of the disclosed compounds. Yet further disclosed are methods for stimulating the cellular immune response in a mammal such as increasing phagocytosis, for example, prolonging the life of phagocytes, inter alia, keratinocytes, neutrophils. As such the disclosed compounds provide methods for treating diseases that relate to the body's immune response.

SUMMARY

The disclosed compounds stabilize HIF-1α and HIF-2α, as well as other factors that are present in a compromised immune system or which are depleted or over taxed by the presence of a disease state and the manifestations of the disease state, inter alia, sepsis. The disclosed compounds can be used to treat cancer and can be co-administered with other cancer therapy drugs. In addition, the disclosed compounds can be used to boost the immune response by a mammal when co-administered with a vaccine, for example, flu vaccines, malarial vaccines, yellow fever vaccines, cancer vaccines, and the like.

BRIEF DESCRIPTION OF THE FIGURES

FIG. 15, depicts mice infected with Newman strain of *S. aureus* followed by treatment with 10 µM of a compound disclosed in Table VIII or DMSO (control) at 2 hours post-infection. The data show the statistically significant reduction in the size of skin lesions (wounds) for animals treated with compound a compound disclosed in Table VIII (solid circles (●)) or DMSO (solid squares (■)).

FIG. 16 depicts mice infected with Newman strain of *S. aureus* followed by treatment with 10 µM of a compound disclosed in Table VIII or no treatment at 2 hours post-infection. The data show the reduction in the size of skin lesions (wounds) for animals treated with compound a compound disclosed in Table VIII (solid circles (●)) or untreated (solid triangles (▲)).

DETAILED DISCLOSURE

Figure 1:
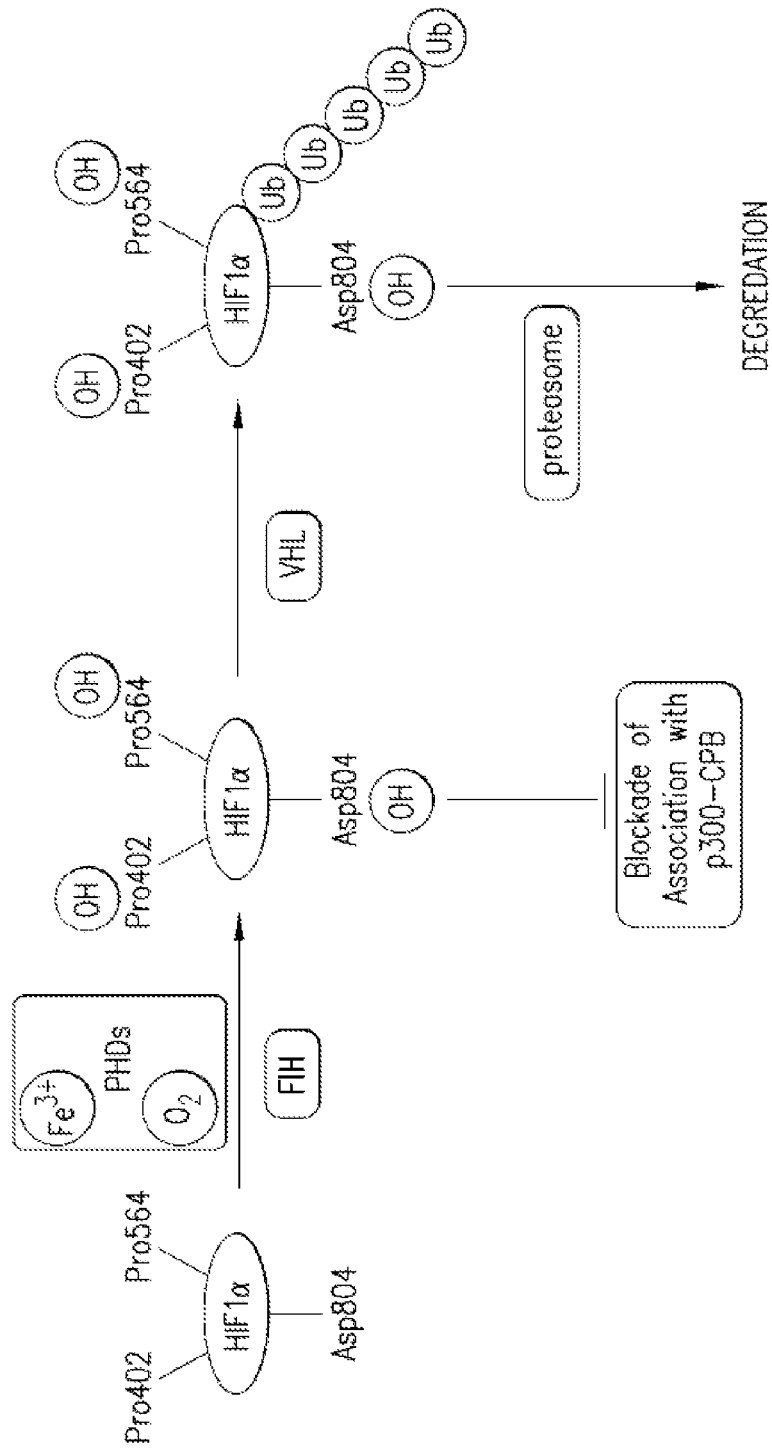
FIG. 1 depicts the normal metabolic pathway of HIF-1α during normoxia.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

"Optional" or "optionally" means that the subsequently described event or circumstance can or cannot occur, and that the description includes instances where the event or circumstance occurs and instances where it does not.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "effective amount" as used herein means "an amount of one or more of the disclosed HIF-1α prolyl hydroxylase inhibitors, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "Treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., infection caused by a microorganism). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. By "antimicrobial" is meant the ability to treat or control (e.g., reduce, prevent, inhibit, break-down, or eliminate) microorganism growth or survival at any concentration. Similarly, the terms "antibacterial," "antiviral," and "antifungal" respectively mean the ability to treat or control (e.g., reduce, prevent, inhibit, break-down, or eliminate) bacterial, viral, and fungal growth or survival at any concentration.

The term "anion" is a type of ion and is included within the meaning of the term "ion". An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion". A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

"Chemotherapeutic agent" is used herein to include any other pharmaceutically active compound that can be used in conjunction with the disclosed HIF-1α prolyl hydroxylase inhibitors, for example, cytotoxic drugs such as 6-hydroxymethylacylfulvene, cyclophosphamide, dacarbazine, carmustine, doxorubicin, and methotrexate. Other chemotherapeutic agents also include anti-inflammatory drugs, i.e., non-steroidal anti-inflammatory compounds such as aspirin.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The transcription factor Hypoxia-Inducible Factor 1 (HIF-1) is one of the key regulators of oxygen homeostasis. It regulates the physiological responses to low oxygen levels (hypoxia) and the pathophysiology of heart attack, cancer, stroke and chronic lung disease. HIF-1 is a heterodimeric protein that consists of two subunits, HIF-1α and HIF-1β. Whereas HIF-1β is constitutively expressed, the expression of HIF-1α is induced by oxygen concentrations below 6%. HIF-1 heterodimers bind to the hypoxia response element (HRE), a 5-RCGTG-3 consensus sequence. Several dozen HIF-1-regulated genes have been identified so far, including genes coding for proteins involved in angiogenesis, energy metabolism, erythropoiesis, cell proliferation and viability, vascular remodeling and vasomotor responses. Therefore, modulation of HIF activation in cells is critical to preventing, controlling, curing, or otherwise affecting a wide array of diseases, disease states, and conditions.

Hypoxia-inducible transcription factor 1-alpha (HIF-1α) plays a central role in cellular adaptation to reduced oxygen availability. Under hypoxic stress, activated HIF-1α strives for oxygen homeostasis by not only maintaining intracellular energy production via the induction of angiogenesis and glycolysis, but also limiting energy consumption by virtue of the inhibition of cell proliferation and DNA repair. In general, HIF-1α activates its target genes, inter alia, EPO, VEGF, and PGK1 through binding to the hypoxia-responsive element in the gene promoter (Wang, G. L. et al., *J Biol Chem* (1993); 268: 21513-21518).

HIF-1α under normal healthy conditions wherein the cells have a sufficient supply of oxygen is readily converted to a degraded form by one of several 4-prolyl hydroxylase enzymes, inter alia, EGLN1 (herein referred to as HIFPH2). As stated above, when cells undergo hypoxia, this enzymatic transformation is slow or entirely stopped and HIF-1α begins to build up in the cell. When this build up of HIF-1α occurs, this protein combines with HIF-1β to form the active transcription factor complex HIF-1. This transcription factor then activates several biological pathways which are present as a response to and a means for alleviating the body's state of hypoxia. These responses include, inter alia, angiogenic, erythropoietic (EPO), glucose metabolism (PGK), matrix alteration, and enhanced capacity of phagocytes to respond to pathogens.

FIG. 1 summaries the metabolism of HIF-1α during normal healthy conditions. The HIF α-subunits are unstable under normoxic conditions; cells continually synthesize and degrade these proteins. The short half-life of HIF-1α is the byproduct of a family of O$_2$— and iron-dependent prolyl hydroxylases (PH1-3), whose action directs HIF α-subunits for degradation by the ubiquitin-proteasome pathway in a process dependent upon interaction with von Hippel-Lindau tumor-suppressor protein (vHL). In FIG. 1, PDH's represents the prolyl hydroxylases that act in the presence of an asparaginyl hydroxylase to hydroxylate prolines 402 and 564, as well as asparagines 804. From this point, because the hydroxylated HIF-1α is also prevented from association with p300-CPB because of other factors, ubiquitin ligase begins to metabolize the hydroxylated HIF-1α via the vHL pathway.

In patients where there is a need for stimulating this response, for example, in patients in need of increased tissue oxygen due to peripheral vascular disease (PVD), inhibiting the HIF1 enzymes, for example, Egl nine homolog 1 (HIFPH2), will stimulate the body's own angiogenic response without the consequences of oxygen deficiency. In addition, in diseases of ischemia, inter alia, CAD and anemia, stimulation of angiogenic, erythropoietic, and metabolism adaption can provide therapeutic benefits. Up regulation of HIF-1α also provides a method for enhancing immunity, for example, by increasing the capacity of phagocytes.

There is therefore a long felt need for methods for controlling the activity of HIF-1α which can be effectively accomplished by compounds that inhibit the 4-prolyl hydroxylase enzymes that degrade HIF-1α. This inhibition of 4-prolyl hydroxylase enzymes, inter alia, HIFPH2 (also referred to herein as EGLN1 or PHD2) and HIFPH3 (also referred to herein as EGLN3 of PHD-3) thereby provide a method for increasing the concentration of HIF-1α in cells and thus providing methods for treating a variety of diseases or disease states.

Disclosed herein are methods for treating one or more diseases, conditions, syndromes, and the like that are affected by the level of hypoxia-inducible transcription factors. Regulation of these factors both during hypoxia and normoxia can provide methods for re-balancing or regulating one or more biological pathways associated with abnormal conditions, inter alia, invasion of the body by pathogens, inter alia, bacteria, fungi, viruses, and parasites, abnormal cellular regulation, i.e., cancer ischemia, and the side effects caused by vaccination.

Targeting HIF1 Stabilization in Cells

HIF-1α is targeted for destruction via prolyl hydroxylation, an oxygen-dependent modification that signals for recognition by the E3 ubiquitin ligase complex containing the von Hippel-Lindau tumor suppressor (VHL). Three prolyl hydroxylases formerly referred to in the literature as EGLN1, EGLN2, and EGLN3 (also know as, have been identified in mammals, among which, EGLN1 (also known as HIFPH2 or PHD2), and EGLN3 (also known as HIFPH3 or PHD3), are hypoxia-inducible at their mRNA levels in a HIF-1α dependent manner. HIF-1α levels are controlled by these prolyl-4-hydroxylases by hydroxylating the HIF-1α proline residues Pro-402 and Pro-564 in humans (Ivan, M. et al., (2001) "HIFα targeted for VHL-mediated destruction by proline hydroxylation: implications for O$_2$ sensing." *Science* 292, 464-468; Jaakkola, P. et al., (2001) "Targeting of HIF-1α to the von Hippel-Lindau ubiquitylation complex by O$_2$-regulated prolyl hydroxylation." *Science* 292, 468-472; and Masson, N. et al., (2001) "Independent function of two destruction domains in hypoxia-inducible factor-α chains activated by prolyl hydroxylation." *EMBO J.* 20, 5197-5206). Under hypoxia conditions, EGLN1 and EGLN3 activity is suppressed.

Stimulated by a build up of the cellular concentration of HIF-1α is the production of Phosphoglycerate Kinase (PGK) and Vascular Endothelial Growth Factor (VEGF). It has been shown that stimulation of VEGF induces the formation of functional neo-vessels in the mouse cornea and enhanced blood flow in a dog model of coronary artery disease. The HIF-1α prolyl hydroxylase inhibitors of the present disclosure provide enhancement in the expression of multiple hypoxia inducible genes including VEGF, GAPDH and erythropoietin (EPO). Additionally, the HIF-1α prolyl hydroxylase inhibitors of the present disclosure provide enhanced the accumulation of HIF1-α in the cytoplasm and nucleus. Transgenic mice expressing a constitutively active HIF-1α in the skin have increased dermal vascularity and had a 13-fold increase in VEGF levels Wounds Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

The present disclosure relates to methods for treating wounds and promoting wound healing in a subject comprising, administering to a subject in need of treatment an effective amount of one or more of the disclosed compounds.

The present disclosure relates to the use of one or more of the disclosed compounds for use in making a medicament for treating wounds and promoting wound healing.

Antimicrobial

The hypoxia-responsive transcription factor HIF-1α is essential for regulation of inflammation in vivo. As such, it has been discovered (Peyssonnaux C. et al., "HIF-1α expression regulates the bactericidal capacity of phagocytes" *J. Clinical Investigation* 115(7), pp 1808-1815 (2005)) that bacterial infection induces HIF-1α expression in myeloid cells even under normoxic conditions, and that HIF-1α regulates the generation of critical molecular effectors of immune defense including granule proteases, antimicrobial peptides, nitric oxide, and TNF-α. Bacterial infection induces a subset of HIF-1α target genes specifically related to microbial killing, thereby demonstrating that HIF-1α has an essential function in innate immunity distinct from hypoxic response. Therefore, HIF-1α function is critical for myeloid cell bactericidal activity and the ability of the host to limit systemic spread of infection from an initial tissue focus. Increased activity of the HIF-1α pathway through vHL deletion supports myeloid cell production of defense factors and improves bactericidal capacity. The disclosed compounds induce HIF-1α activity and can also boost bacterial killing and NO production in a HIF-1α-specific fashion. These discoveries provide methods for enhancing innate immune responses to microbial, for example, bacterial, infection.

Without wishing to be limited by theory, the disclosed compounds can increase the stabilization of HIF-1 protein by acting directly or indirectly on one or more cellular processes which act to destabilize or to metabolize cellular components that stabilize the presence of HIF-1 protein, protect it from inhibition, or to increase the activity of the protein. Alternatively, the disclosed compounds can increase the activity of the HIF-1 protein by inhibiting or otherwise blocking the activity of compounds that inhibit the activity of the HIF-1 protein. As such, disclosed herein is a method for improving the treatment of microbial infections by administering a substance that increases the activity or level of at least one HIF-1 protein in a subject suffering from the microbial infection or at increased risk of microbial infection.

In one aspect, disclosed herein are methods for modulating the activity of at least one HIF-1 protein. As such, the disclosed methods comprise contacting at least one HIF-1 protein or HIF-1 interacting protein with one or more of the disclosed compounds that modulate the activity of the HIF-1 protein, or causing contact between the protein and substance. In the embodiment, the contacting is accomplished in vitro. In another embodiment, the contacting is accomplished in vivo. In a further embodiment, the contacting is accomplished ex vivo.

In another aspect, disclosed herein is a method of treating a subject infected or at risk of infection by a microbial agent comprising administering to a subject a therapeutically effective amount of one or more of the disclosed compounds. In one embodiment, the compound increases the amount or activity of HIF-1. In another embodiment, the microbial agent is a pathogen. Iterations of this embodiment related to pathogens includes, bacteria, fungi, protozoa, viruses, yeasts, and the like. A yet further iteration of this aspect relates to a method for treating a subject infected by or at risk of infection by a microbial agent comprising, increasing the microbial pathogen-killing activity of the subject's immune cells.

One method for increasing the stabilization of HIF-1 is to inhibit the activity of 4-prolyl hydroxylase enzymes that begin the cellular break down of HIF-1α thereby preventing HIF-1α from combining with HIF-1β to form HIF-1. As such, disclosed herein are methods for increasing the cellular response to disease states such as infection, i.e., presence of a pathogen such as a bacterium, a virus, a parasite, a yeast, a fungus, and the like by increasing phagocytosis. Also disclosed herein are methods for treating cancer by increasing the cellular immune response, for example, by stabilizing HIF-1, thereby increasing the ability of the body to reduce tumor size. Further disclosed herein are methods for treating diseases wherein an immune response can be stimulated by vaccination.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (carbocyclic and aryl rings) or can comprise one or more heteroatoms in the ring (heterocyclic and heteroaryl). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and unsubstituted acyclic hydrocarbyl:
For the purposes of the present disclosure the term "substituted and unsubstituted acyclic hydrocarbyl" encompasses 3 categories of units:
1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and unsubstituted cyclic hydrocarbyl:
For the purposes of the present disclosure the term "substituted and unsubstituted cyclic hydrocarbyl" encompasses 5 categories of units:
1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
  i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
  ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decalinyl ($C_{10}$), decahydroazulenyl ($C_{10}$).
  iii) carbocyclic rings which are substituted or unsubstituted bicyclic hydrocarbon rings, non-limiting examples of which include, bicyclo-[2.1.1]hexanyl, bicyclo[2.2.1]

heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$).

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

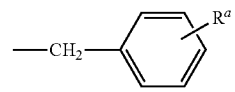

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

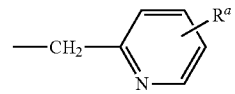

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan can have alternative characterizations. For example, 1,2,3,4-tetrahydroquinoline having the formula:

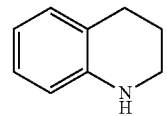

is, for the purposes of the present disclosure, considered a heterocyclic unit. 6,7-Dihydro-5H-cyclopentapyrimidine having the formula:

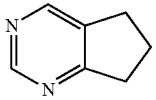

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the disclosure. For example, 1,2,3,4-tetrahydro-[1,8]naphthyridine having the formula:

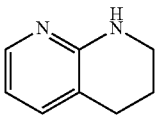

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms can be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) substituted or unsubstituted $C_1$-$C_{12}$ linear, $C_3$-$C_{12}$ branched, or $C_3$-$C_{12}$ cyclic alkyl; for example, methyl ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), isopropyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_2$ branched, or $C_3$-$C_2$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_2$ linear or $C_3$-$C_2$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;

iv) substituted or unsubstituted $C_6$ or $C_{10}$ aryl; for example, phenyl, 2-chlorophenyl, 3-hydroxyphenyl, 4-nitrophenyl, 2-fluoro-4-methylphenyl, 3,5-dinitrophenyl, 8-hydroxynaphth-1-yl, 6-sulfonylnapth-2-yl, and the like;

v) substituted or unsubstituted $C_1$-$C_9$ heterocyclic; for example, as defined further herein;

vi) substituted or unsubstituted $C_1$-$C_{11}$ heteroaryl; for example, as defined further herein;

vii) halogen; for example, fluoro, chloro, bromo, and iodo;

viii) —$[C(R^{23a})(R^{23b})]_xOR^{10}$;

$R^{10}$ is chosen from:

a) —H;

b) substituted or unsubstituted $C_1$-$C_{12}$ linear, $C_3$-$C_{12}$ branched, or $C_3$-$C_{12}$ cyclic alkyl;

c) $C_6$ or $C_{10}$ substituted or unsubstituted aryl or alkylenearyl;

d) $C_1$-$C_9$ substituted or unsubstituted heterocyclic;

e) $C_1$-$C_{11}$ substituted or unsubstituted heteroaryl;

ix) —$[C(R^{23a})(R^{23b})]_xN(R^{11a})(R^{11b})$;

$R^{11a}$ and $R^{11b}$ are each independently chosen from:

a) —H;

b) —$OR^{12}$;

$R^{12}$ is hydrogen or $C_1$-$C_4$ linear alkyl;

c) substituted or unsubstituted $C_1$-$C_{12}$ linear, $C_3$-$C_{12}$ branched, or $C_3$-$C_{12}$ cyclic alkyl;

d) $C_6$ or $C_{10}$ substituted or unsubstituted aryl;

e) $C_1$-$C_9$ substituted or unsubstituted heterocyclic;

f) $C_1$-$C_{11}$ substituted or unsubstituted heteroaryl; or g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;

x) —$[C(R^{23a})(R^{23b})]_xC(O)R^{13}$;

$R^{13}$ is:

a) substituted or unsubstituted $C_1$-$C_{12}$ linear, $C_3$-$C_{12}$ branched, or $C_3$-$C_{12}$ cyclic alkyl;

b) —$OR^{14}$;

$R^{14}$ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;

c) —$N(R^{15a})(R^{15b})$;

$R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

xi) —[C($R^{23a}$)($R^{23b}$)]$_x$OC(O)$R^{16}$;
$R^{16}$ is:
a) substituted or unsubstituted $C_1$-$C_{12}$ linear, $C_3$-$C_2$ branched, or $C_3$-$C_{12}$ cyclic alkyl;
b) —N($R^{17a}$)($R^{17b}$);
$R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —[C($R^{23a}$)($R^{23}$)]$_x$N$R^{18}$C(O)$R^{19}$;
$R^{18}$ is:
a) —H; or
b) substituted or unsubstituted $C_1$-$C_4$ linear, $C_3$-$C_4$ branched, or $C_3$-$C_4$ cyclic alkyl;
$R^{19}$ is:
a) substituted or unsubstituted $C_1$-$C_{12}$ linear, $C_3$-$C_{12}$ branched, or $C_3$-$C_{12}$ cyclic alkyl;
b) —N($R^{20a}$)($R^{20b}$);
$R^{20a}$ and $R^{20b}$ are each independently hydrogen, substituted or unsubstituted $C_1$-$C_{12}$ linear, $C_3$-$C_{12}$ branched, or $C_3$-$C_{12}$ cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

xiii) —[C($R^{23a}$)($R^{23b}$)]$_x$CN;
xiv) —[C($R^{23a}$)($R^{23b}$)]$_x$NO$_2$;
xv) —[C($R^{23a}$)($R^{23b}$)]$_x$$R^{21}$;
$R^{21}$ is $C_1$-$C_{10}$ linear, $C_3$-$C_{10}$ branched, or $C_3$-$C_{10}$ cyclic alkyl substituted by from 1 to 21 halogen atoms chosen from —F, —Cl, —Br, or —I;
xvi) —[C($R^{23a}$)($R^{23b}$)]$_x$SO$_2$$R^{22}$;
$R^{22}$ is hydrogen, hydroxyl, substituted or unsubstituted $C_1$-$C_4$ linear or $C_3$-$C_4$ branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl;
$R^{23a}$ and $R^{23b}$ are each independently hydrogen or $C_1$-$C_4$ alkyl; and
the index x is an integer from 0 to 5.

The compounds disclosed herein include all salt forms, for example, salts of both basic groups, inter alia, amines, as well as salts of acidic groups, inter alia, carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

For the purposes of the present disclosure the terms "compound," "analog," and "composition of matter" stand equally well for one another and include all enantiomeric forms, diastereomeric forms, salts, and the like, and the terms "compound," "analog," and "composition of matter."

HIF-1α Prolyl Hydroxylase Inhibitors

The disclosed compounds have the following formulae:

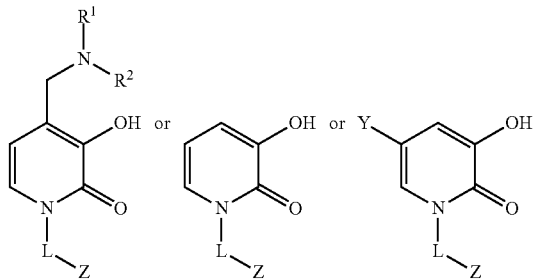

wherein L is chosen from CH$_2$ or SO$_2$, thereby providing for N-substituted benzyl or N-substituted sulfonylaryl-3-hydroxypyridin-2-(1H)-ones. Y, $R^1$ and $R^2$ are further defined herein below.

Disclosed herein are N-substituted benzyl and N-substituted sulfonylaryl-4-aminomethylene-3-hydroxypyridin-2-(1H)-ones that are HIF-1α prolyl hydroxylase inhibitors having the formula:

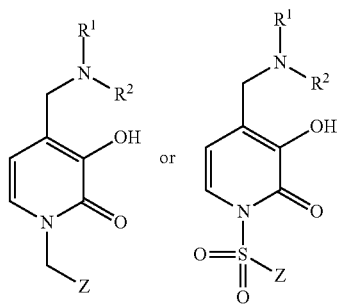

wherein $R^1$ and $R^2$ are further defined herein below.

Alkyl Piperizine-1-Carboxylates

One category of these compounds relates to $C_1$-$C_4$ linear or branched alkyl 4-{[(1-N-(chloro- or fluoro-substituted)-benzyl]-3-hydroxy-2-oxo-1,2-dihydropyridin-4-yl)methyl}piperazine-1-carboxylates having the formula:

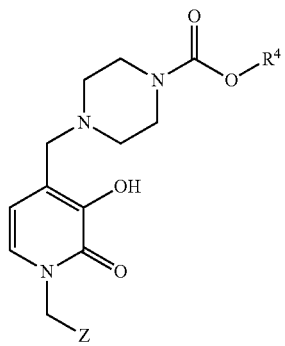

wherein Z is a phenyl group that is substituted with from 1 to 5 halogen atoms that are chosen from chloro and fluoro, and $R^1$ and $R^2$ are taken together to form a piperazine ring that is substituted with alkylcarboxy unit wherein $R^4$ is chosen from $C_1$-$C_4$ linear or $C_3$-$C_4$ branched alkyl, for example, ten butyl 4-{[1-(4chlorobenzyl)-3-hydroxy-2-oxo1,2-dihydropyridin-4-yl]methyl}piperazine-1-carboxylate having the formula:

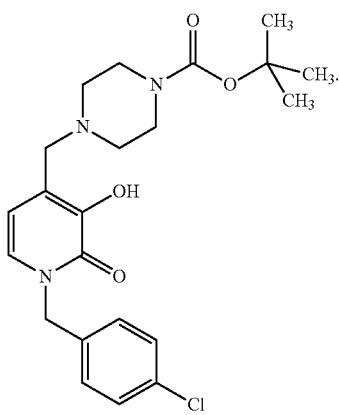 [SMILES: CC(C)(C)OC(=O)N1CCN(Cc2ccn(Cc3ccc(Cl)cc3)c(=O)c2O)CC1]

One aspect of $R^4$ units relates to compounds wherein $R^4$ is tert-butyl ($C_4$). Another aspect of $R^4$ units relates to compounds wherein $R^4$ is methyl ($C_1$). A further aspect of $R^4$ units relates to compounds wherein $R^4$ is ethyl ($C_2$). A still further aspect of $R^4$ units relates to compounds wherein $R^4$ is chosen from n-propyl ($C_3$), iso-propyl ($C_3$), n-butyl ($C_4$), sec-butyl ($C_4$), and iso-butyl ($C_4$). $R^4$ is not hydrogen, therefore, a carboxylate unit having the formula: —$CO_2H$ is expressly excluded from this category, but may be included in other categories as described herein below.

Z is phenyl substituted with from 1 to 5 halogens chosen from fluorine and chlorine. One aspect of Z units relates to compounds wherein Z is 4-chlorophenyl. Another aspect of Z units relates to compounds wherein Z is chosen from 2-chlorophenyl, 3-chlorophenyl, 2-fluorophenyl, 3-fluorophenyl, or 4-fluorophenyl. A further aspect of Z units relates to compounds wherein Z is chosen from 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, and 2,6-dichlorophenyl.

The following are non-limiting examples of compounds according to this category:

methyl 4-{[1-(4-chlorobenzyl)-3-hydroxy-2-oxo-1,2-dihydropyridin-4-yl]methyl}-piperazine-1-carboxylate having the formula:

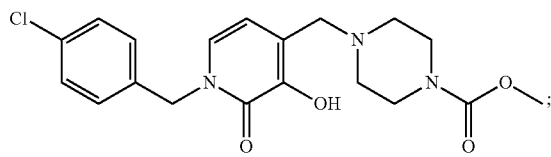 [SMILES: COC(=O)N1CCN(Cc2ccn(Cc3ccc(Cl)cc3)c(=O)c2O)CC1]

methyl 4-{[1-(3-chlorobenzyl)-3-hydroxy-2-oxo-1,2-dihydropyridin-4-yl]methyl}-piperazine-1-carboxylate having the formula:

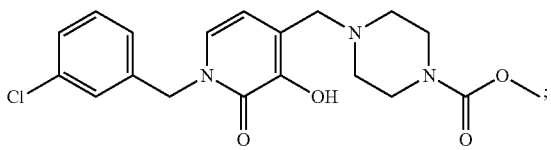 [SMILES: COC(=O)N1CCN(Cc2ccn(Cc3cccc(Cl)c3)c(=O)c2O)CC1]

methyl 4-{[1-(2-chlorobenzyl)-3-hydroxy-2-oxo-1,2-dihydropyridin-4-yl]methyl}-piperazine-1-carboxylate having the formula:

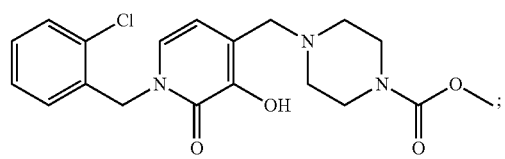

ethyl 4-{[1-(4-chlorobenzyl)-3-hydroxy-2-oxo-1,2-dihydropyridin-4-yl]methyl}-piperazine-1-carboxylate having the formula:

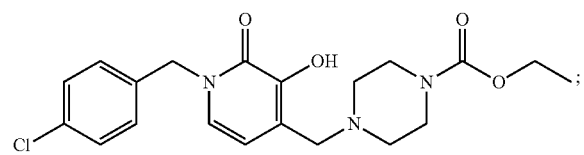 [SMILES: CCOC(=O)N1CCN(Cc2ccn(Cc3ccc(Cl)cc3)c(=O)c2O)CC1]

ethyl 4-{[1-(3-chlorobenzyl)-3-hydroxy-2-oxo-1,2-dihydropyridin-4-yl]methyl}-piperazine-1-carboxylate having the formula:

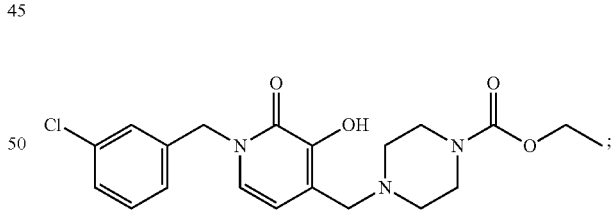

ethyl 4-{[1-(2-chlorobenzyl)-3-hydroxy-2-oxo-1,2-dihydropyridin-4-yl]methyl}-piperazine-1-carboxylate having the formula:

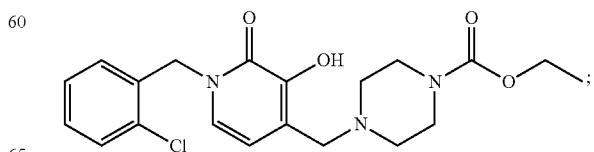

tert-butyl 4-{[1-(4-chlorobenzyl)-3-hydroxy-2-oxo-1,2-dihydropyridin-4-yl]methyl}-piperazine-1-carboxylate having the formula:

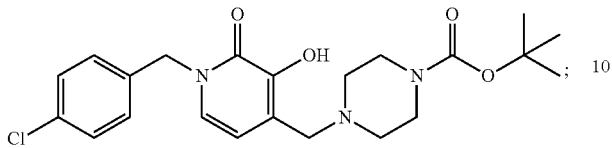

tert-butyl 4-{[1-(3-chlorobenzyl)-3-hydroxy-2-oxo-1,2-dihydropyridin-4-yl]methyl}-piperazine-1-carboxylate having the formula:

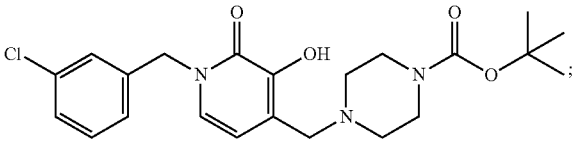 [SMILES: CC(C)(C)OC(=O)N1CCN(Cc2ccn(Cc3cccc(Cl)c3)c(=O)c2O)CC1]

tert-butyl 4-{[1-(2-chlorobenzyl)-3-hydroxy-2-oxo-1,2-dihydropyridin-4-yl]methyl}-piperazine-1-carboxylate having the formula:

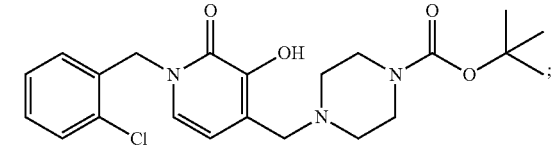 [SMILES: CC(C)(C)OC(=O)N1CCN(Cc2ccn(Cc3ccccc3Cl)c(=O)c2O)CC1]

methyl 4-{[1-(4-fluorobenzyl)-3-hydroxy-2-oxo-1,2-dihydropyridin-4-yl]methyl}-piperazine-1-carboxylate having the formula:

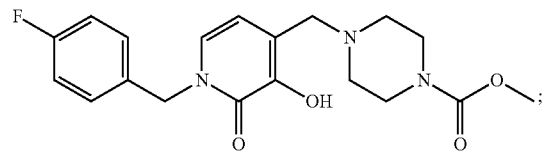 [SMILES: COC(=O)N1CCN(Cc2ccn(Cc3ccc(F)cc3)c(=O)c2O)CC1]

methyl 4-{[1-(3-fluorobenzyl)-3-hydroxy-2-oxo-1,2-dihydropyridin-4-yl]methyl}-piperazine-1-carboxylate having the formula:

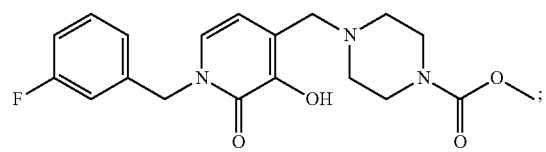 [SMILES: COC(=O)N1CCN(Cc2ccn(Cc3cccc(F)c3)c(=O)c2O)CC1]

methyl 4-{[1-(2-fluorobenzyl)-3-hydroxy-2-oxo-1,2-dihydropyridin-4-yl]methyl}-piperazine-1-carboxylate having the formula:

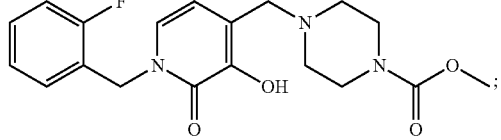

ethyl 4-{[1-(4-fluorobenzyl)-3-hydroxy-2-oxo-1,2-dihydropyridin-4-yl]methyl}-piperazine-1-carboxylate having the formula:

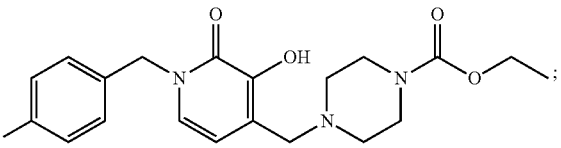

ethyl 4-{[1-(3-fluorobenzyl)-3-hydroxy-2-oxo-1,2-dihydropyridin-4-yl]methyl}-piperazine-1-carboxylate having the formula:

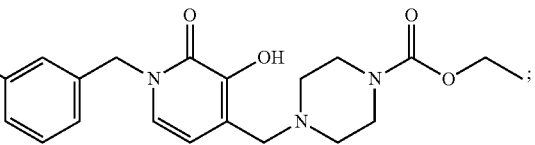

ethyl 4-{[1-(2-fluorobenzyl)-3-hydroxy-2-oxo-1,2-dihydropyridin-4-yl]methyl}-piperazine-1-carboxylate having the formula:

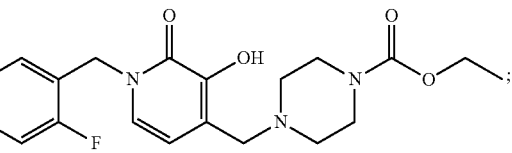

tert-butyl 4-{[1-(4-fluorobenzyl)-3-hydroxy-2-oxo-1,2-dihydropyridin-4-yl]methyl}-piperazine-1-carboxylate having the formula:

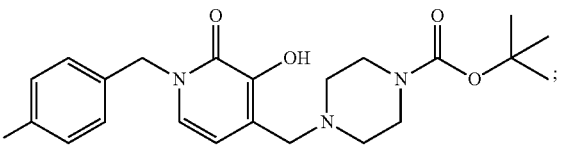

tert-Butyl 4-{[1-(3-fluorobenzyl)-3-hydroxy-2-oxo-1,2-dihydropyridin-4-yl]methyl}-piperazine-1-carboxylate having the formula:

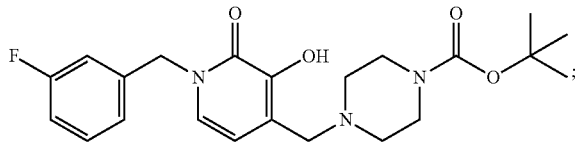 [SMILES: CC(C)(C)OC(=O)N1CCN(Cc2ccn(Cc3cccc(F)c3)c(=O)c2O)CC1]

and
tert-butyl 4-{[1-(2-fluorobenzyl)-3-hydroxy-2-oxo-1,2-dihydropyridin-4-yl]methyl}piperazine-1-carboxylate having the formula:

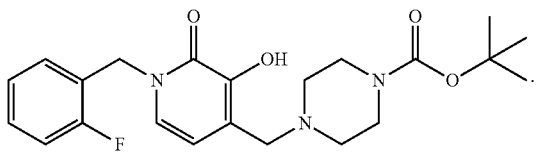

Another category of compounds relates to N-unsubstituted-benzyl-4-aminomethyl-3-hydroxypyridin-2-(1H)-ones, wherein Z is an unsubstituted phenyl group, having the formula:

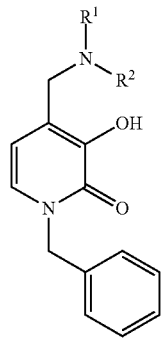

wherein $R^1$ and $R^2$ are are be taken together to form a substituted or unsubstituted heterocyclic or heteroaryl ring.

A first aspect of this category relates to compounds having the formula:

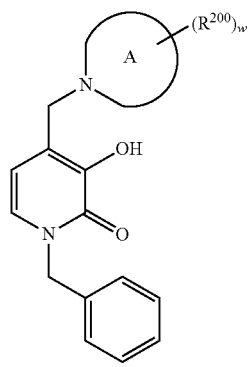

wherein $R^1$ and $R^2$ are be taken together to form a substituted or unsubstituted heterocyclic or heteroaryl ring represented by ring A having from 2 to 20 carbon atoms and from 1 to 7 heteroatoms, and $R^{200}$ represents from 0 to 40 substitutions form hydrogen. The index w is an integer from 0 to 40. Non-limiting examples of rings include diazirinyl ($C_1$), 1,2,3,4-tetrazolyl ($C_1$), aziridinyl ($C_2$), urazolyl ($C_2$), [1,2,3]triazolyl ($C_2$), [1,2,4]triazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), 1H-imidazolyl ($C_3$), pyrrolidinyl ($C_4$), morpholinyl ($C_4$), piperazinyl ($C_4$), piperidinyl ($C_4$), piperidin-2-onyl (valerolactam) ($C_5$), 7H-purinyl ($C_5$), 9H-purinyl ($C_5$), 6-amino-9H-purinyl ($C_5$), 2,3,4,5-tetrahydro-1H-azepinyl ($C_6$), 5H-pyrrolo[3,2-d]pyrimidinyl ($C_6$), 7H-pyrrolo[2,3-d]pyrimidinyl ($C_6$), and 1,2,3,4-tetrahydroquinoline ($C_9$).

Each $R^{200}$ unit is independently chosen from:
i) substituted or unsubstituted $C_1$-$C_{12}$ linear, $C_3$-$C_{12}$ branched, or $C_3$-$C_{12}$ cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;
ii) substituted or unsubstituted $C_2$-$C_{12}$ linear, $C_3$-$C_2$ branched, or $C_3$-$C_2$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;
iii) substituted or unsubstituted $C_1$-$C_{12}$ linear or $C_3$-$C_2$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;
iv) substituted or unsubstituted $C_6$ or $C_{10}$ aryl; for example, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-cyano-naphthylen-1-yl ($C_{10}$), and the like;
v) substituted or unsubstituted $C_1$-$C_9$ heterocyclic; for example, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydropyranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), and the like;
vi) substituted or unsubstituted $C_1$-$C_{11}$ heteroaryl; for example, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), pyridinyl ($C_5$), and the like;
vii) halogen; for example, —F, —Cl, —Br, or —I;

viii) —[C(R$^{37a}$)(R$^{37b}$)]$_y$OR$^{24}$;
R$^{24}$ is chosen from:
a) —H;
b) substituted or unsubstituted C$_2$-C$_{12}$ linear, C$_3$-C$_{12}$ branched, or C$_3$-C$_{12}$ cyclic alkyl;
c) substituted or unsubstituted C$_6$ or C$_{10}$ aryl or C$_7$ or C$_{10}$ alkylenearyl; for example, phenyl or benzyl
d) substituted or unsubstituted C$_1$-C$_9$ heterocyclic;
e) substituted or unsubstituted C$_1$-C$_{11}$ heteroaryl;
  for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

ix) —[C(R$^{37a}$)(R$^{37b}$)]$_y$N(R$^{25a}$)(R$^{25b}$);
R$^{25a}$ and R$^{25b}$ are each independently chosen from:
a) —H;
b) —OR$^{26}$;
  R$^{26}$ is hydrogen or C$_1$-C$_4$ linear alkyl;
c) substituted or unsubstituted C$_2$-C$_{12}$ linear, C$_3$-C$_{12}$ branched, or C$_3$-C$_{12}$ cyclic alkyl;
d) substituted or unsubstituted C$_6$ or C$_{10}$ aryl;
e) substituted or unsubstituted C$_1$-C$_9$ heterocyclic;
f) substituted or unsubstituted C$_1$-C$_{11}$ heteroaryl; or
g) R$^{25a}$ and R$^{25b}$ can be taken together to form a substituted or unsubstituted ring having from 3 to 10 carbon atoms and from 0 to 3 heteroatoms chosen from oxygen, nitrogen, and sulfur;
  for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;

x) —[C(R$^{37a}$)(R$^{37b}$)]$_y$C(O)R$^{27}$;
R$^{27}$ is:
a) substituted or unsubstituted C$_2$-C$_{12}$ linear, C$_3$-C$_{12}$ branched, or C$_3$-C$_{12}$ cyclic alkyl;
b) —OR$^{28}$;
  R$^{28}$ is hydrogen, substituted or unsubstituted C$_1$-C$_4$ linear alkyl, substituted or unsubstituted C$_6$ or C$_{10}$ aryl, substituted or unsubstituted C$_1$-C$_9$ heterocyclic, substituted or unsubstituted C$_1$-C$_{11}$ heteroaryl;
c) —N(R$^{29a}$)(R$^{29b}$);
  R$^{29a}$ and R$^{29b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; or R$^{29a}$ and R$^{29b}$ can be taken together to form a substituted or unsubstituted ring having from 3 to 10 carbon atoms and from 0 to 3 heteroatoms chosen from oxygen, nitrogen, and sulfur;
  for example, —COCH$_3$, —CH$_2$COCH$_3$, —OCH$_2$CH$_3$, —CH$_2$COCH$_2$CH$_3$, —COCH$_2$CH$_3$, —CH$_2$COCH$_2$CH$_2$CH$_3$, and the like;

xi) —[C(R$^{37a}$)(R$^{37b}$)]$_y$OC(O)R$^{30}$;
R$^{30}$ is:
a) C$_1$-C$_{12}$ substituted or unsubstituted linear, branched, or cyclic alkyl;
b) —N(R$^{31a}$)(R$^{31b}$);
  R$^{31a}$ and R$^{31b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; or R$^{31a}$ and R$^{31b}$ can be taken together to form a substituted or unsubstituted ring having from 3 to 10 carbon atoms and from 0 to 3 heteroatoms chosen from oxygen, nitrogen, and sulfur;
  for example, —OC(O)CH$_3$, —CH$_2$OC(O)CH$_3$, —OC(O)NH$_2$, —CH$_2$OC(O)NH$_2$, —OC(O)NHCH$_3$, —CH$_2$OC(O)NHCH$_3$, —OC(O)N(CH$_3$)$_2$, —CH$_2$OC(O)N(CH$_3$)$_2$, and the like;

xii) —[C(R$^{37a}$)(R$^{37b)}$]$_y$NR$^{32}$C(O)R$^{33}$;
R$^{32}$ is:
a) —H; or
b) substituted or unsubstituted C$_1$-C$_4$ linear, C$_3$-C$_4$ branched, or C$_3$-C$_4$ cyclic alkyl;
R$^{33}$ is:
a) substituted or unsubstituted C$_2$-C$_{12}$ linear, C$_3$-C$_{12}$ branched, or C$_3$-C$_{12}$ cyclic alkyl;
b) —N(R$^{34a}$)(R$^{34b}$);
  R$^{34a}$ and R$^{34b}$ are each independently hydrogen, substituted or unsubstituted C$_2$-C$_{12}$ linear, C$_3$-C$_{12}$ branched, or C$_3$-C$_{12}$ cyclic alkyl; substituted or unsubstituted C$_6$ or C$_{10}$ aryl, substituted or unsubstituted C$_1$-C$_9$ heterocyclic, substituted or unsubstituted C$_1$-C$_{11}$ heteroaryl; C$_1$-C$_{11}$ substituted or unsubstituted heteroaryl; or R$^{34a}$ and R$^{34b}$ can be taken together to form a substituted or unsubstituted ring having from 3 to 10 carbon atoms and from 0 to 3 heteroatoms chosen from oxygen, nitrogen, and sulfur;
  for example, —NHC(O)CH$_3$, —CH$_2$NHC(O)CH$_3$, —NHC(O)NH$_2$, —CH$_2$NHC(O)NH$_2$, —NHC(O)NHCH$_3$, —CH$_2$NHC(O)NHCH$_3$, —OC(O)N(CH$_3$)$_2$, —CH$_2$NHC(O)N(CH$_3$)$_2$, and the like;

xiii) —[C(R$^{37a}$)(R$^{37b}$)]$_y$CN; for example; —CN, —CH$_2$CN, and —CH$_2$CH$_2$CN;

xiv) —[C(R$^{37a}$)(R$^{37b}$)]$_y$NO$_2$; for example; —NO$_2$, —CH$_2$NO$_2$, and —CH$_2$CH$_2$NO$_2$;

xv) —[C(R$^{37a}$)(R$^{37b}$)]$_y$R$^{35}$; for example, —CH$_2$F, —CHF$_2$, —CF$_3$, —CCl$_3$, or —CBr$_3$;
R$^{35}$ is C$_1$-C$_{10}$ linear, C$_3$-C$_{10}$ branched, or C$_3$-C$_{10}$ cyclic alkyl substituted by from 1 to 21 halogen atoms chosen from —F, —Cl, —Br, or —I;

xvi) —[C(R$^{37a}$)(R$^{37b}$)]$_y$SO$_2$R$^{36}$;
R$^{36}$ is hydrogen, hydroxyl, substituted or unsubstituted C$_1$-C$_4$ linear or C$_3$-C$_4$ branched alkyl; substituted or unsubstituted C$_6$, C$_{10}$, or C$_{14}$ aryl; C$_7$-C$_{15}$ alkylenearyl; substituted or unsubstituted C$_1$-C$_9$ heterocyclic; or substituted or unsubstituted C$_1$-C$_{11}$ heteroaryl;
  for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xv) two hydrogen atoms on a ring carbon atom can be substituted to form a =O, =S, or =NH unit;

R$^{37a}$ and R$^{37b}$ are each independently hydrogen or C$_1$-C$_4$ alkyl; and the index y is an integer from 0 to 5.

A first embodiment of this aspect relates to compounds wherein R$^1$ and R$^2$ are taken together to form a 5-member substituted or unsubstituted C$_1$-C$_4$ heterocyclic or a substituted or unsubstituted $C_1$-$C_4$ heteroaryl ring, non-limiting examples of which include a ring chosen from:

i) 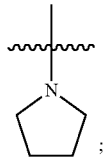

ii) 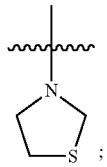

iii) 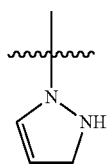

iv) 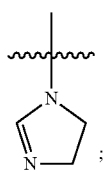

v) 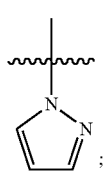

vi) 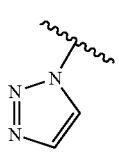

vii) 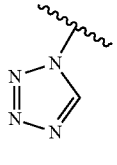

viii) 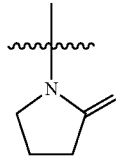

A first iteration of this embodiment relates to HIF-1α prolyl hydroxylase inhibitors having the formula:

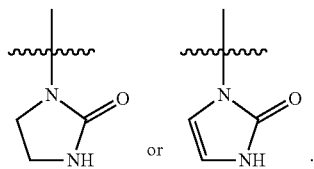

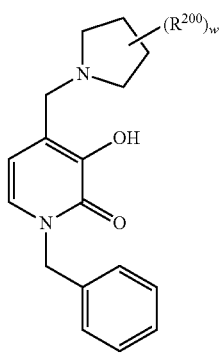

$R^{200}$ represents from 0 to 2 substitutions for a ring hydrogen, wherein the substitutions for hydrogen are independently chosen from:
  i) $C_1$-$C_4$ linear or $C_3$-$C_4$ branched alkyl;
  ii) $C_1$-$C_4$ linear or $C_3$-$C_4$ branched alkoxy;
  iii) hydroxyl;
  iv) cyano;
  v) nitro;
  vi) amino, methylamino, or dimethylamino;
  vii) carboxy, methyl carboxy; or ethyl carboxy;
  viii) formyl, acetyl, or propionyl;
  ix) amido, methyl amido, or dimethyl amido;
  x) halogen;
  xi) heterocyclic; or
  xii) heteroaryl.

Non-limiting examples of this iteration include HIF-1α prolyl hydroxylase inhibitors having the formula:

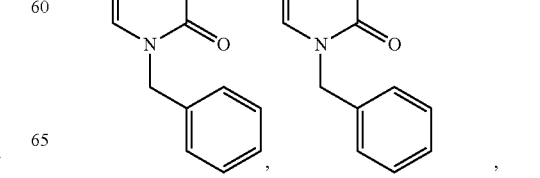

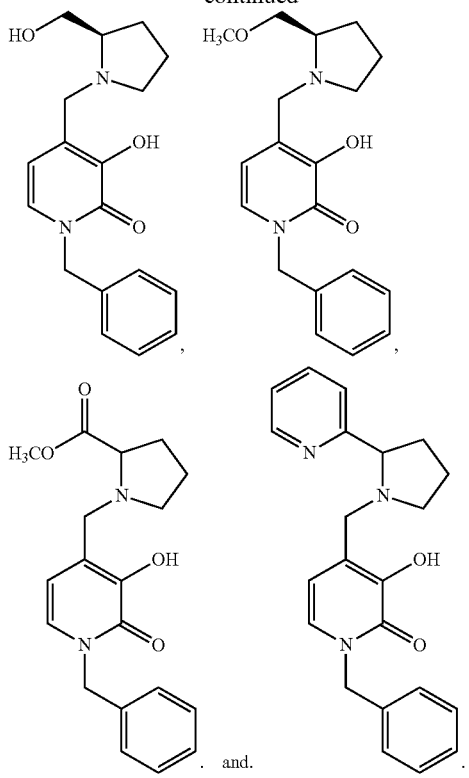

A further iteration of this embodiment relates to HIF-1α prolyl hydroxylase inhibitors wherein $R^1$ and $R^2$ are taken together to form a 5-member substituted or unsubstituted heterocyclic or heteroaryl ring having more than one heteroatom in the ring. Non-limiting examples include:

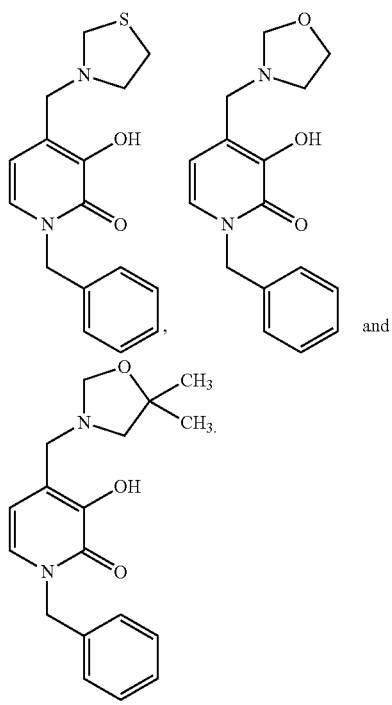

Another embodiment of this aspect relates to HIF-1α prolyl hydroxylase inhibitors wherein $R^1$ and $R^2$ are taken together to form a substituted or unsubstituted $C_4$-$C_{11}$ heterocyclic or a substituted or unsubstituted $C_4$-$C_{11}$ heteroaryl ring, non-limiting examples of which are chosen from:

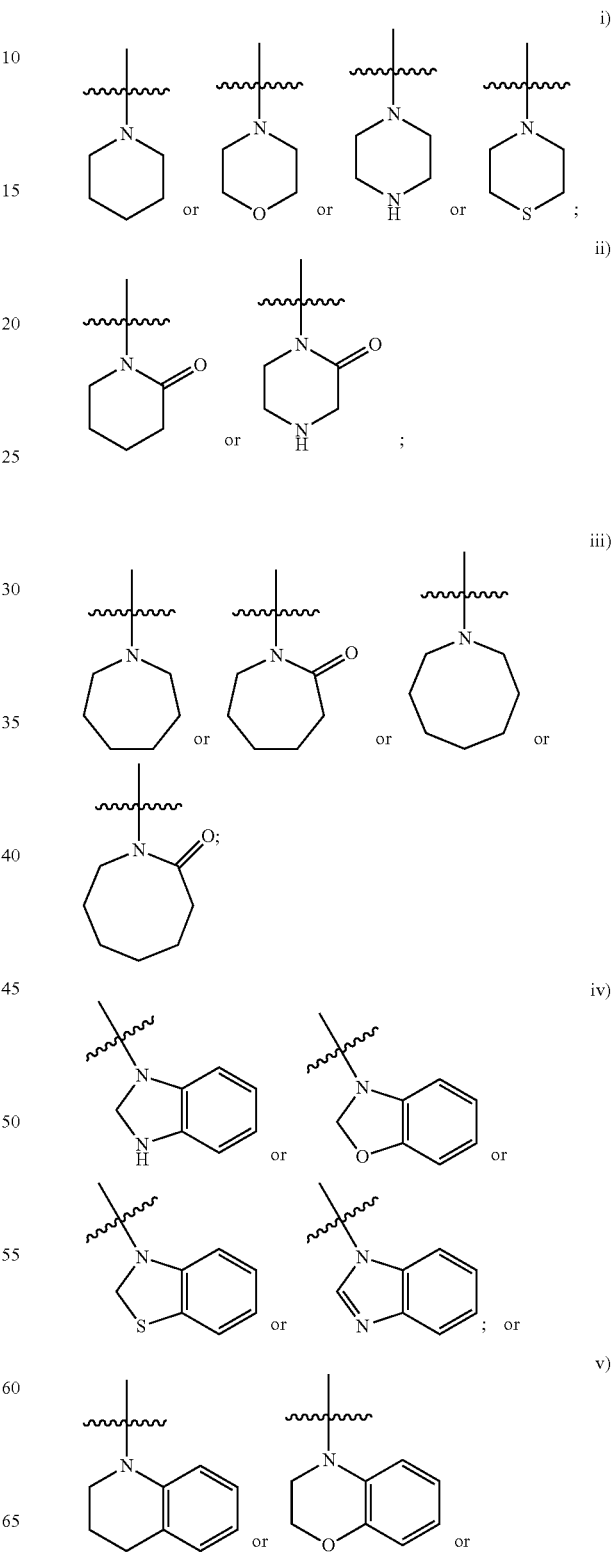

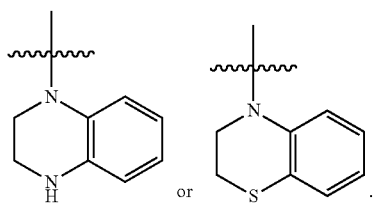
Non-limiting examples of this embodiment include:
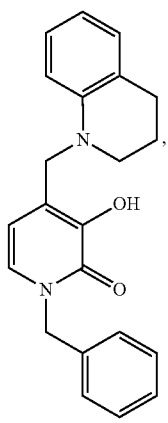
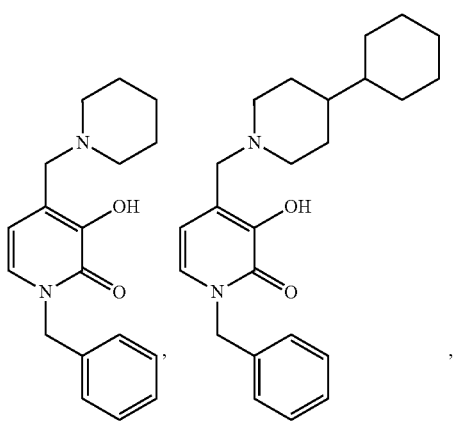
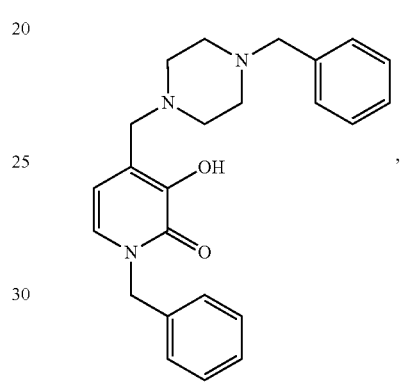
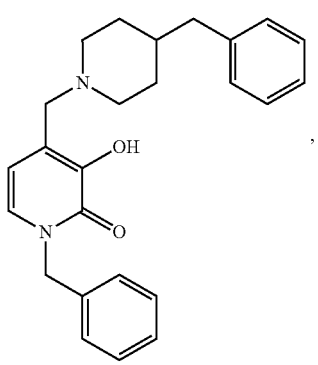
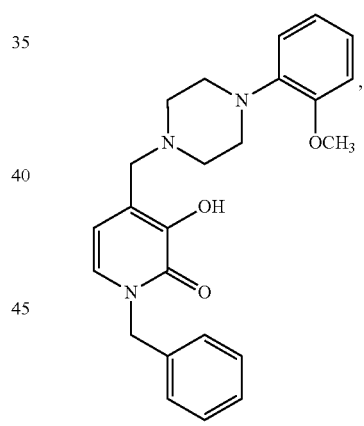
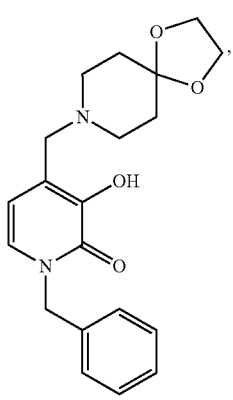
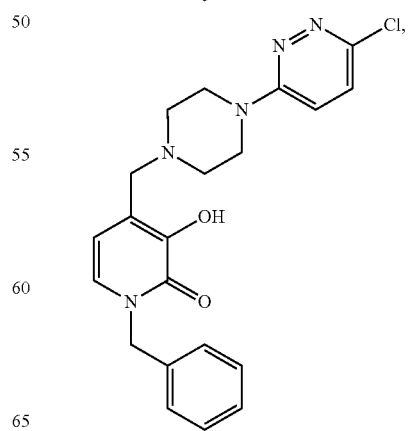

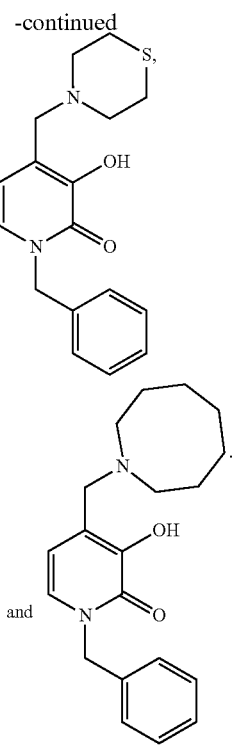

Another category of compounds has the formula:

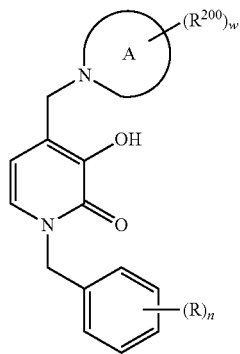

wherein $R^{200}$ and the index w are the same as defined herein above. R represents from 0 to 5 substitutions for hydrogen, wherein each R is independently chosen from:

i) $C_1$-$C_{12}$ substituted or unsubstituted linear, branched, or cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) $C_2$-$C_{12}$ substituted or unsubstituted linear, branched, or cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) $C_2$-$C_{12}$ substituted or unsubstituted linear or branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like;

iv) $C_6$ or $C_{10}$ substituted or unsubstituted aryl; for example, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-cyano-naphthylen-1-yl ($C_{10}$), and the like;

v) $C_1$-$C_9$ substituted or unsubstituted heterocyclic; for example, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydropyranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), and the like;

vi) $C_1$-$C_{11}$ substituted or unsubstituted heteroaryl; for example, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), pyridinyl ($C_5$), and the like;

vii) halogen; for example, —F, —Cl, —Br, or —I;

viii) —[C($R^{23a}$)($R^{23b}$)]$_x$O$R^{10}$;

$R^{10}$ is chosen from:
a) —H;
b) $C_1$-$C_{12}$ substituted or unsubstituted linear, branched, or cyclic alkyl;
c) $C_6$ or $C_{10}$ substituted or unsubstituted aryl or alkylenearyl;
d) $C_1$-$C_9$ substituted or unsubstituted heterocyclic;
e) $C_1$-$C_{11}$ substituted or unsubstituted heteroaryl;
for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

ix) —[C($R^{23a}$)($R^{23b}$)]$_x$N($R^{11a}$)($R^{11b}$);

$R^{11a}$ and $R^{11b}$ are each independently chosen from:
a) —H;
b) —O$R^{12}$;
$R^{12}$ is hydrogen or $C_1$-$C_4$ linear alkyl;
c) $C_1$-$C_{12}$ substituted or unsubstituted linear, branched, or cyclic alkyl;
d) $C_6$ or $C_{10}$ substituted or unsubstituted aryl;
e) $C_1$-$C_9$ substituted or unsubstituted heterocyclic;
f) $C_1$-$C_{11}$ substituted or unsubstituted heteroaryl; or
g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;
for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;

x) [C($R^{23a}$)($R^{23b}$)]$_x$C(O)$R^{13}$;

R¹³ is:
a) $C_1$-$C_{12}$ substituted or unsubstituted linear, branched, or cyclic alkyl;
b) —OR¹⁴;
R¹⁴ is hydrogen, substituted or unsubstituted $C_1$-$C_4$ linear alkyl, $C_6$ or $C_{10}$ substituted or unsubstituted aryl, $C_1$-$C_9$ substituted or unsubstituted heterocyclic, $C_1$-$C_{11}$ substituted or unsubstituted heteroaryl;
c) —N(R¹⁵ᵃ)(R¹⁵ᵇ);
R¹⁵ᵃ and R¹⁵ᵇ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or R¹⁵ᵃ and R¹⁵ᵇ can be taken together to form a substituted or unsubstituted ring having from 3 to 10 carbon atoms and from 0 to 3 heteroatoms chosen from oxygen, nitrogen, and sulfur;
for example, —COCH₃, —CH₂COCH₃, —OCH₂CH₃, —CH₂COCH₂CH₃, —COCH₂CH₂CH₃, —CH₂COCH₂CH₂CH₃, and the like;
xi) —[C(R²³ᵃ)(R²³ᵇ)]ₓOC(O)R¹⁶;
R¹⁶ is:
a) $C_1$-$C_{12}$ substituted or unsubstituted linear, branched, or cyclic alkyl;
b) —N(R¹⁷ᵃ)(R¹⁷ᵇ);
R¹⁷ᵃ and R¹⁷ᵇ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or R¹⁷ᵃ and R¹⁷ᵇ can be taken together to form a substituted or unsubstituted ring having from 3 to 10 carbon atoms and from 0 to 3 heteroatoms chosen from oxygen, nitrogen, and sulfur;
xii) —[C(R²³ᵃ)(R²³ᵇ)]ₓNR¹⁸C(O)R¹⁹;
R¹⁸ is:
a) —H; or
b) $C_1$-$C_4$ substituted or unsubstituted linear, branched, or cyclic alkyl;
R¹⁹ is:
a) $C_1$-$C_{12}$ substituted or unsubstituted linear, branched, or cyclic alkyl;
b) —N(R²⁰ᵃ)(R²⁰ᵇ);
R²⁰ᵃ and R²⁰ᵇ are each independently hydrogen, $C_1$-$C_{12}$ substituted or unsubstituted linear, branched, or cyclic alkyl; $C_6$ or $C_{10}$ substituted or unsubstituted aryl; $C_1$-$C_9$ substituted or unsubstituted heterocyclic; $C_1$-$C_{11}$ substituted or unsubstituted heteroaryl; or R²⁰ᵃ and R²⁰ᵇ can be taken together to form a substituted or unsubstituted ring having from 3 to 10 carbon atoms and from 0 to 3 heteroatoms chosen from oxygen, nitrogen, and sulfur;
for example, —NHC(O)CH₃, —CH₂NHC(O)CH₃, —NHC(O)NH₂, —CH₂NHC(O)NH₂, —NHC(O)NHCH₃, —CH₂NHC(O)NHCH₃, —OC(O)N(CH₃)₂, —CH₂NHC(O)N(CH₃)₂, and the like;
xiii) —[C(R²³ᵃ)(R²³ᵇ)]ₓCN; for example; —CN, —CH₂CN, and —CH₂CH₂CN;
xiv) —[C(R²³ᵃ)(R²³ᵇ)]ₓNO₂; for example; —NO₂, —CH₂NO₂, and —CH₂CH₂NO₂;
xv) —[C(R²³ᵃ)(R²³ᵇ)]ₓR²¹; for example, —CH₂F, —CHF₂, —CF₃, —CCl₃, or —CBr₃;
R²¹ is $C_1$-$C_{10}$ linear, branched, or cyclic alkyl substituted by from 1 to 21 halogen atoms chosen from —F, —Cl, —Br, or —I;
xvi) —[C(R²³ᵃ)(R²³ᵇ)]ₓSO₂R²²;

R²² is hydrogen, hydroxyl, substituted or unsubstituted $C_1$-$C_4$ linear or branched alkyl; substituted or unsubstituted $C_6$, $C_{10}$, or $C_{14}$ aryl; $C_7$-$C_{15}$ alkylenearyl; $C_1$-$C_9$ substituted or unsubstituted heterocyclic; or $C_1$-$C_{11}$ substituted or unsubstituted heteroaryl; for example, —SO₂H, —CH₂SO₂H, —SO₂CH₃, —CH₂SO₂CH₃, —SO₂C₆H₅, and —CH₂SO₂C₆H₅;
R²³ᵃ and R²³ᵇ are each independently hydrogen or $C_1$-$C_4$ alkyl; and
the index x is an integer from 0 to 5.

Non-limiting examples of this category include compounds having the formula:

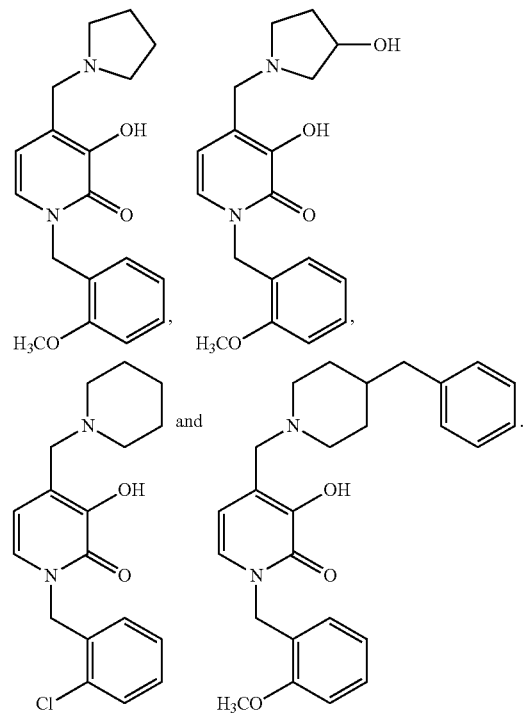

A further category of compounds relates to unsubstituted N-benzyl-4-aminomethyl-3-hydroxypyridin-2-(1H)-ones having the formula:

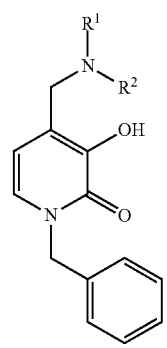

wherein R¹ and R² are each independently chosen from:
i) hydrogen;
ii) substituted or unsubstituted $C_1$-$C_{10}$ linear, branched, or cyclic alkyl;
iii) substituted or unsubstituted $C_2$-$C_{10}$ linear, branched, or cyclic alkenyl;

iv) substituted or unsubstituted $C_2$-$C_{10}$ linear or branched alkynyl;
v) substituted or unsubstituted $C_6$ or $C_{10}$ aryl;
vi) substituted or unsubstituted $C_1$-$C_9$ heterocyclic; or
vii) substituted or unsubstituted $C_1$-$C_9$ heteroaryl.

The first aspect of this category relates to HIF-1α prolyl hydroxylase inhibitors wherein $R^2$ is hydrogen and $R^1$ is substituted or unsubstituted $C_1$-$C_9$ heterocyclic or $C_1$-$C_9$ heteroaryl. In a first embodiment, $R^1$ is a substituted heterocyclic group, non-limiting examples of which include aziridinyl ($C_2$), azetidinyl ($C_3$), pyrrolidinyl ($C_4$), morpholinyl ($C_4$), piperazinyl ($C_4$), piperidinyl ($C_4$), piperidin-2-onyl (valerolactam) ($C_5$), and azepan-2-onyl (caprolactam) ($C_6$), wherein the $R^1$ unit can be bonded to the nitrogen atom at any position in the ring. In addition, the $C_1$-$C_9$ heterocyclic or $C_1$-$C_9$ heteroaryl ring can be substituted at any position whether a ring carbon or a ring heteroatom, for example, a ring nitrogen. Non-limiting examples of this embodiment include:

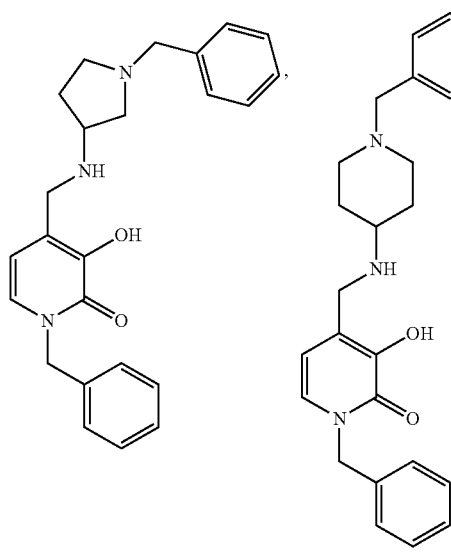

In another embodiment, $R^2$ is hydrogen and $R^1$ is substituted or unsubstituted $C_3$-$C_{12}$ cycloalkyl wherein the cycloalkyl ring can be substituted at any ring position. Non-limiting examples of this embodiment include:

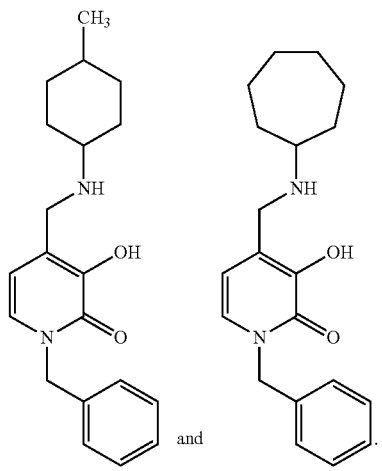 [SMILES: CC1CCC(NCc2ccn(Cc3ccccc3)c(=O)c2O)CC1 ; O=c1c(O)c(CNC2CCCCCC2)ccn1Cc1ccccc1]

A yet further category of compounds relates to unsubstituted N-benzyl-4-aminomethyl-3-hydroxypyridin-2-(1H)-ones having the formula:

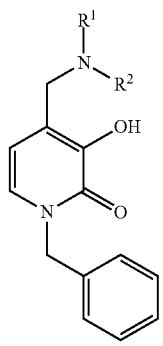

$R^1$ and $R^2$ are each independently hydrogen or substituted or unsubstituted $C_1$-$C_{10}$ linear or branched alkyl, wherein the alkyl unit can be substituted by one or more units independently chosen from:
i) $C_1$-$C_8$ linear, branched, or cyclic alkoxy;
ii) hydroxy;
iii) halogen;
iv) cyano;
v) amino, $C_1$-$C_8$ mono-alkylamino, $C_1$-$C_8$ di-alkylamino;
vi) —$SR^{40}$; $R^{40}$ is hydrogen or $C_1$-$C_4$ linear or branched alkyl;
vii) substituted or unsubstituted $C_6$ of $C_{10}$ aryl;
viii) substituted or unsubstituted $C_1$-$C_9$ heterocyclic; or
ix) substituted or unsubstituted $C_1$-$C_9$ heteroaryl.
Non-limiting examples of this category include:

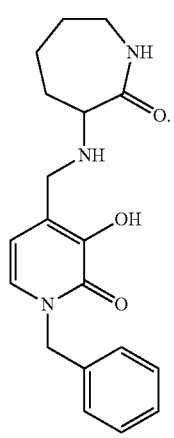

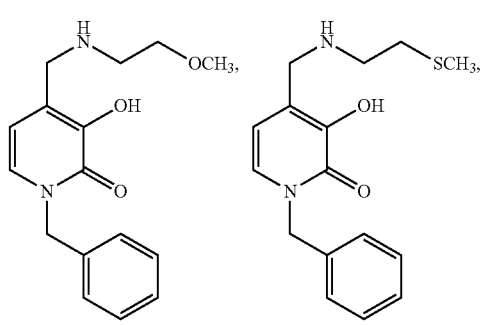

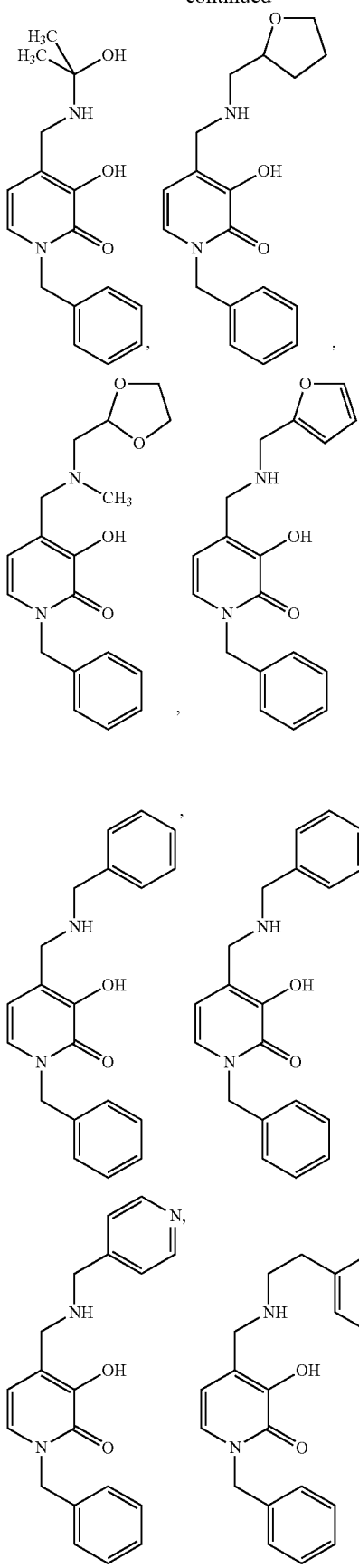

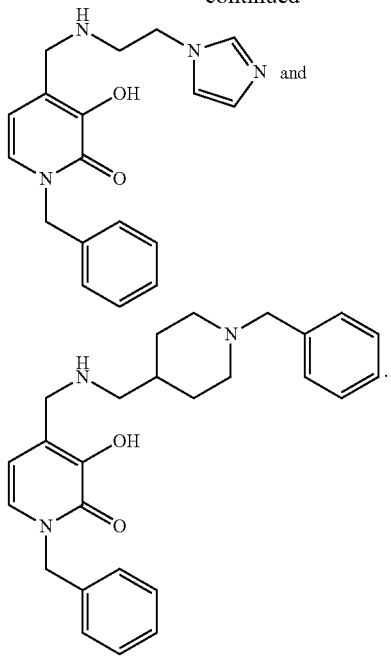

A still further category of the disclosed compounds has the formula:

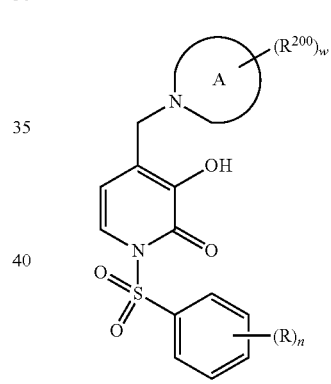

wherein $R^{200}$ and the index w are the same as defined herein above. R represents from 0 to 5 substitutions for hydrogen, wherein each R is independently chosen from:

i) substituted or unsubstituted $C_1$-$C_{12}$ linear, $C_3$-$C_{12}$ branched, or $C_3$-$C_{12}$ cyclic alkyl; for example, methyl ($C_1$), ($C_1$), chloromethyl ($C_1$), trifluoromethyl ($C_1$), aminomethyl ($C_1$), ethyl ($C_2$), hydroxymethyl 1-chloroethyl ($C_2$), 2-hydroxyethyl ($C_2$), 1,2-difluoroethyl ($C_2$), n-propyl ($C_3$), iso-propyl ($C_3$), 3-carboxypropyl ($C_3$), cyclopropyl ($C_3$), 2-methyl-cyclopropyl ($C_3$), n-butyl ($C_4$), sec-butyl ($C_4$), iso-butyl ($C_4$), tert-butyl ($C_4$), cyclobutyl ($C_4$), 2,3-dihydroxycyclobutyl ($C_4$), pentyl ($C_5$), cyclopentyl ($C_5$), hexyl ($C_6$), and cyclohexyl ($C_6$), and the like;

ii) substituted or unsubstituted $C_2$-$C_{12}$ linear, $C_3$-$C_{12}$ branched, or $C_3$-$C_{12}$ cyclic alkenyl; for example, ethenyl ($C_2$), 2-chloroethenyl (also 2-chlorovinyl) ($C_2$), 3-propenyl ($C_3$), 1-propenyl (also 2-methylethenyl) ($C_3$), isopropenyl (also 2-methylethen-2-yl) ($C_3$), buten-4-yl ($C_4$), 4-hydroxybuten-1-yl ($C_4$), cyclobutenyl ($C_4$), cyclopentenyl ($C_5$), cyclopentadienyl ($C_5$), cyclohexenyl ($C_6$), 7-hydroxy-7-methyloct-4-en-2-yl ($C_9$), and 7-hydroxy-7-methyloct-3,5-dien-2-yl ($C_9$), and the like;

iii) substituted or unsubstituted $C_2$-$C_{12}$ linear or $C_3$-$C_{12}$ branched alkynyl; for example, ethynyl ($C_2$), prop-2-ynyl (also propargyl) ($C_3$), propyn-1-yl ($C_3$), 2-methyl-hex-4-yn-1-yl ($C_7$); 5-hydroxy-5-methylhex-3-ynyl ($C_7$), 6-hydroxy-6-methylhept-3-yn-2-yl ($C_8$), 5-hydroxy-5-ethyl-hept-3-ynyl ($C_9$), and the like;

iv) substituted or unsubstituted $C_6$ or $C_{10}$ aryl; for example, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), 6-cyano-naphthylen-1-yl ($C_{10}$), and the like;

v) substituted or unsubstituted $C_1$-$C_9$ heterocyclic; for example, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydropyranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), and the like;

vi) substituted or unsubstituted $C_1$-$C_{11}$ heteroaryl; for example, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), pyridinyl ($C_5$), and the like;

vii) halogen; for example, —F, —Cl, —Br, or —I;

viii) —[C($R^{23a}$)($R^{23b}$)]$_x$O$R^{10}$;

$R^{10}$ is chosen from:
a) —H;
b) substituted or unsubstituted $C_1$-$C_{12}$ linear, $C_3$-$C_{12}$ branched, or $C_3$-$C_{12}$ cyclic alkyl;
c) substituted or unsubstituted $C_6$ or $C_{10}$ aryl or $C_7$ or $C_{10}$ alkylenearyl;
d) substituted or unsubstituted $C_1$-$C_9$ heterocyclic;
e) substituted or unsubstituted $C_1$-$C_{11}$ heteroaryl;
for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

ix) —[C($R^{23a}$)($R^{23b}$)]$_x$N($R^{11a}$)($R^{11b}$);

$R^{11a}$ and $R^{11b}$ are each independently chosen from:
a) —H;
b) —O$R^{12}$;
  $R^{12}$ is hydrogen or $C_1$-$C_4$ linear alkyl;
c) substituted or unsubstituted $C_1$-$C_{12}$ linear, $C_3$-$C_{12}$ branched, or $C_3$-$C_{12}$ cyclic alkyl;
d) substituted or unsubstituted $C_6$ or $C_{10}$ aryl;
e) substituted or unsubstituted $C_1$-$C_9$ heterocyclic;
f) substituted or unsubstituted $C_1$-$C_{11}$ heteroaryl; or
g) $R^{11a}$ and $R^{11b}$ can be taken together to form a substituted or unsubstituted ring having from 3 to 10 carbon atoms and from 0 to 3 heteroatoms chosen from oxygen, nitrogen, and sulfur;
for example, —NH$_2$, —CH$_2$NH$_2$, —NHCH$_3$, —N(CH$_3$)$_2$, —NHOH, —NHOCH$_3$, —NH(CH$_2$CH$_3$), —CH$_2$NHCH$_3$, —CH$_2$N(CH$_3$)$_2$, —CH$_2$NH(CH$_2$CH$_3$), and the like;

x) —[C($R^{23a}$)($R^{23b}$)]$_x$C(O)$R^{13}$;

$R^{13}$ is:
a) substituted or unsubstituted $C_1$-$C_{12}$ linear, $C_3$-$C_{12}$ branched, or $C_3$-$C_{12}$ cyclic alkyl;
b) —O$R^{14}$;

$R^{14}$ is hydrogen, substituted or unsubstituted $C_1$-$C_4$ linear alkyl, substituted or unsubstituted $C_6$ or $C_{10}$ aryl, substituted or unsubstituted $C_1$-$C_9$ heterocyclic, substituted or unsubstituted $C_1$-$C_{11}$ heteroaryl;

c) —N($R^{15a}$)($R^{15b}$);

$R^{15a}$ and $R^{15b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{15a}$ and $R^{15b}$ can be taken together to form a substituted or unsubstituted ring having from 3 to 10 carbon atoms and from 0 to 3 heteroatoms chosen from oxygen, nitrogen, and sulfur;

for example, —COCH$_3$, —CH$_2$COCH$_3$, —OCH$_2$CH$_3$, —CH$_2$COCH$_2$CH$_3$, —COCH$_2$CH$_3$, —CH$_2$COCH$_2$CH$_2$CH$_3$, and the like;

xi) —[C($R^{23a}$)($R^{23b}$)]$_x$OC(O)$R^{16}$;

$R^{16}$ is:
a) substituted or unsubstituted $C_1$-$C_{12}$ linear, $C_3$-$C_{12}$ branched, or $C_3$-$C_{12}$ cyclic alkyl;
b) —N($R^{17a}$)($R^{17b}$);

$R^{17a}$ and $R^{17b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{17a}$ and $R^{17b}$ can be taken together to form a substituted or unsubstituted ring having from 3 to 10 carbon atoms and from 0 to 3 heteroatoms chosen from oxygen, nitrogen, and sulfur;

xii) —[C($R^{23a}$)($R^{23b}$)]$_x$N$R^{18}$C(O)$R^{19}$;

$R^{18}$ is:
a) —H; or
b) substituted or unsubstituted $C_1$-$C_4$ linear, $C_3$-$C_4$ branched, or $C_3$-$C_4$ cyclic alkyl;

$R^{19}$ is:
a) substituted or unsubstituted $C_1$-$C_{12}$ linear, $C_3$-$C_4$ cyclic alkyl;
b) —N($R^{20a}$)($R^{20b}$);

$R^{20a}$ and $R^{20b}$ are each independently hydrogen, substituted or unsubstituted $C_1$-$C_{12}$ linear, $C_3$-$C_{12}$ branched, or $C_3$-$C_{12}$ cyclic alkyl; substituted or unsubstituted $C_6$ or $C_{10}$ aryl; substituted or unsubstituted $C_1$-$C_9$ heterocyclic; substituted or unsubstituted $C_1$-$C_{11}$ heteroaryl; or $R^{20a}$ and $R^{20b}$ can be taken together to form a substituted or unsubstituted ring having from 3 to 10 carbon atoms and from 0 to 3 heteroatoms chosen from oxygen, nitrogen, and sulfur;

for example, —NHC(O)CH$_3$, —CH$_2$NHC(O)CH$_3$, —NHC(O)NH$_2$, —CH$_2$NHC(O)NH$_2$, —NHC(O)NHCH$_3$, —CH$_2$NHC(O)NHCH$_3$, —OC(O)N(CH$_3$)$_2$, —CH$_2$NHC(O)N(CH$_3$)$_2$, and the like;

xiii) —[C($R^{23a}$)($R^{23b}$)]$_x$CN; for example; —CN, —CH$_2$CN, and —CH$_2$CH$_2$CN;

xiv) —[C($R^{23a}$)($R^{23b}$)]$_x$NO$_2$; for example; —NO$_2$, —CH$_2$NO$_2$, and —CH$_2$CH$_2$NO$_2$;

xv) —[(R$^{23a}$)(R$^{23b}$)]$_x$R$^{21}$; for example, —CH$_2$F, —CHF$_2$, —CF$_3$, —CCl3, or —CBr$_3$;

$R^{21}$ is $C_1$-$C_{10}$ linear, branched, or cyclic alkyl substituted by from 1 to 21 halogen atoms chosen from —F, —Cl, —Br, or —I;

xvi) —[C($R^{23a}$)($R^{23b}$)]$_x$SO$_2$$R^{22}$;

$R^{22}$ is hydrogen, hydroxyl, substituted or unsubstituted $C_1$-$C_4$ linear or $C_3$-$C_4$ branched alkyl; substituted or unsubstituted $C_6$, $C_{10}$, or $C_{14}$ aryl; $C_7$-$C_{15}$ alkylenearyl; substituted or unsubstituted $C_1$-$C_9$ heterocyclic; or substituted or unsubstituted $C_1$-$C_{11}$ heteroaryl; for example, —$SO_2H$, —$CH_2SO_2H$, —$SO_2CH_3$, —$CH_2SO_2CH_3$, —$SO_2C_6H_5$, and —$CH_2SO_2C_6H_5$;

$R^{23a}$ and $R^{23b}$ are each independently hydrogen or $C_1$-$C_4$ alkyl; and the index x is an integer from 0 to 5.

One aspect embodiment of this category relates to HIF-1α prolyl hydroxylase inhibitors wherein $R^1$ and $R^2$ are taken together to form a 5-member substituted or unsubstituted $C_1$-$C_4$ heterocyclic or a substituted or unsubstituted $C_1$-$C_4$ heteroaryl ring, non-limiting examples of which include a ring chosen from:

i)
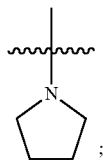
;

ii)
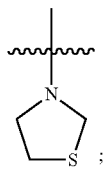
;

iii)
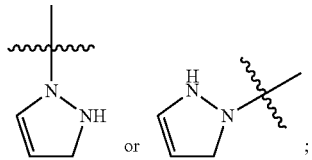
;

iv)
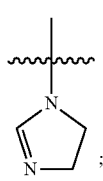
;

v)
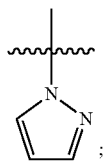
;

vi)
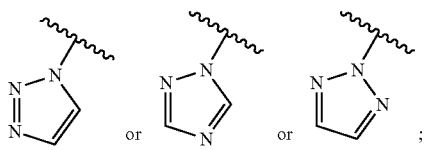
;

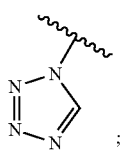
;

vii)
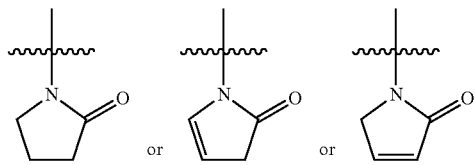
; or viii)
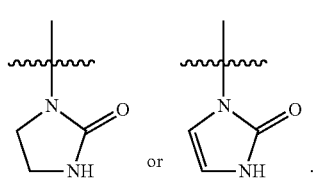
.

Another aspect of this category relates to HIF-1α prolyl hydroxylase inhibitors wherein $R^1$ and $R^2$ are taken together to form a substituted or unsubstituted $C_4$-$C_{11}$ heterocyclic or a substituted or unsubstituted $C_4$-$C_{11}$ heteroaryl ring, non-limiting examples of which are chosen from:

i)
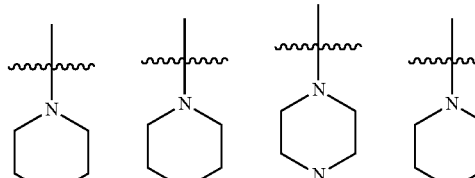
;

ii)
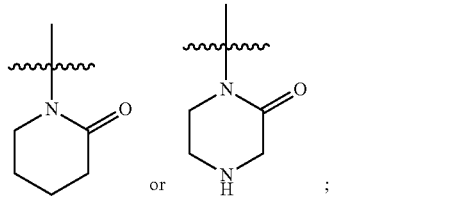
;

iii)
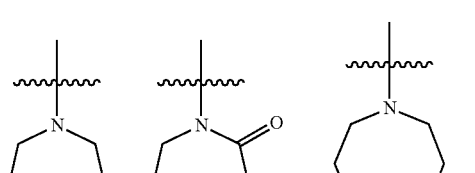
;

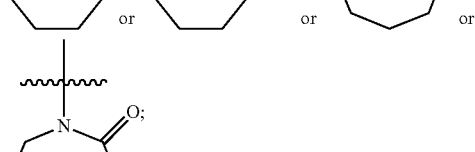
;

iv)
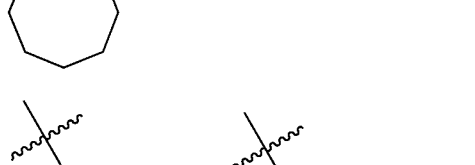
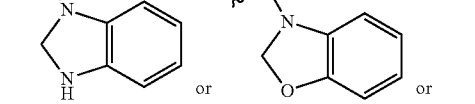
or

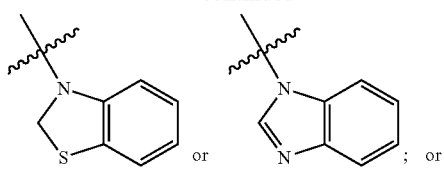
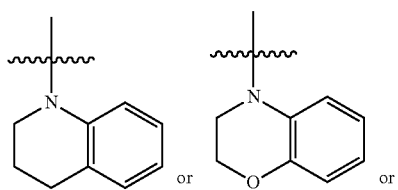
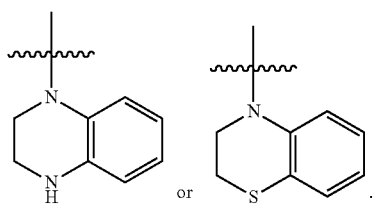
Non-limiting examples of this category include compounds having the formula:
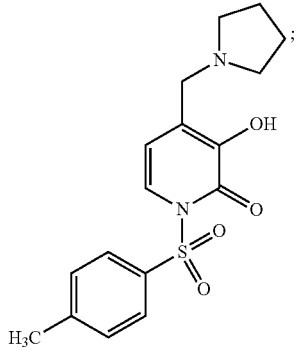
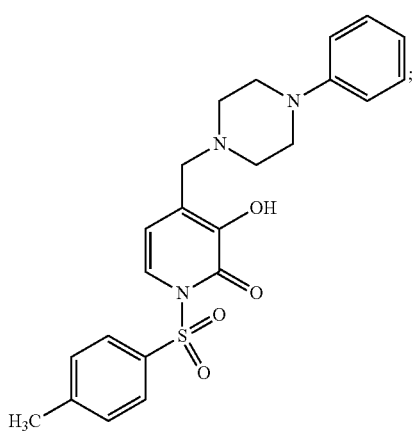
v)
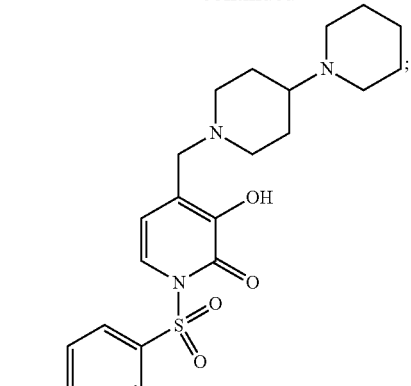
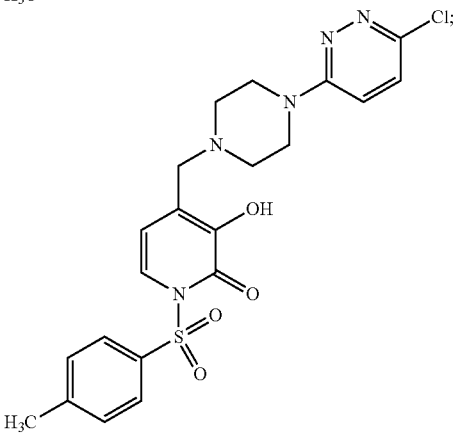
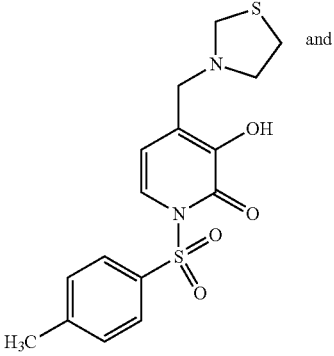
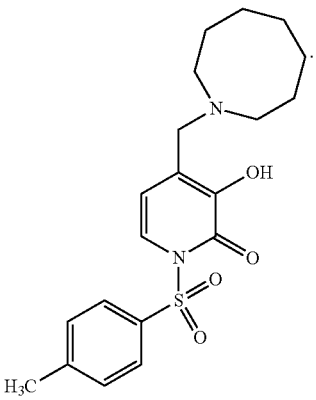

A further category of the disclosed compounds has the formula:

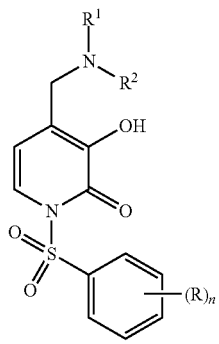

wherein R represents from 1 to 5 optional substitutions for a phenyl ring hydrogen atom, $R^1$ and $R^2$ are each independently hydrogen or substituted or unsubstituted $C_1$-$C_{10}$ linear or branched alkyl, wherein the alkyl unit can be substituted by one or more units independently chosen from:
  i) $C_1$-$C_8$ linear, $C_3$-$C_8$ branched, or $C_3$-$C_8$ cyclic alkoxy;
  ii) hydroxy;
  iii) halogen;
  iv) cyano;
  v) amino, $C_1$-$C_8$ mono-alkylamino, $C_1$-$C_8$ di-alkylamino;
  vi) —$SR^{40}$; $R^{40}$ is hydrogen or $C_1$-$C_4$ linear or branched alkyl;
  vii) substituted or unsubstituted $C_6$ of $C_{10}$ aryl;
  viii) substituted or unsubstituted $C_1$-$C_9$ heterocyclic; or
  ix) substituted or unsubstituted $C_1$-$C_9$ heteroaryl.

Non-limiting examples of this category include:

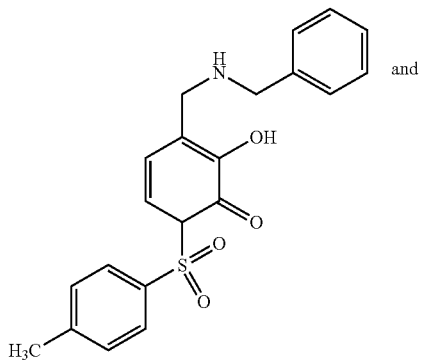
and

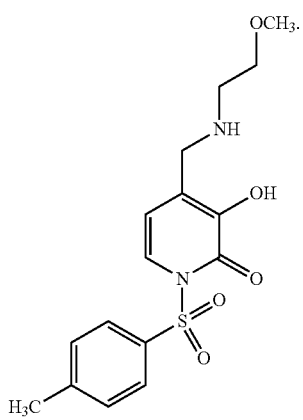

A still yet further category of the disclosed HIF-1α prolyl hydroxylase inhibitors relates to compounds having the formula:

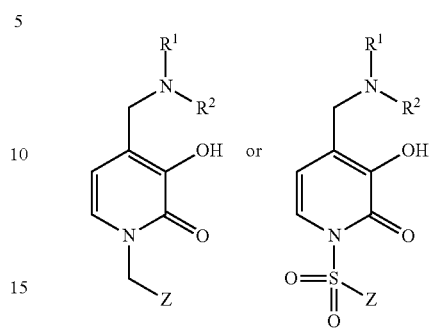

wherein $R^1$ and $R^2$ are taken together to form a substituted or unsubstituted piperazine ring, the substitutions on the ring as defined for $R^{200}$ herein above.

A yet still further category of the disclosed HIF-1α prolyl hydroxylase inhibitors have the formula:

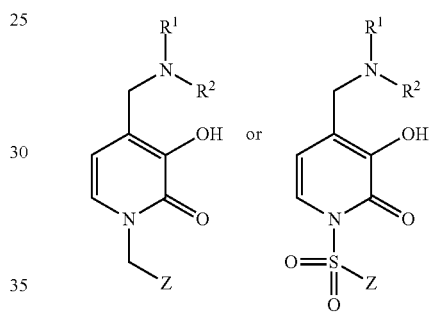

wherein $R^1$ and $R^2$ can be taken together to form a substituted or unsubstituted heterocyclic or heteroaryl ring having from 2 to 20 carbon atoms and from 1 to 7 heteroatoms wherein the rings formed exclude a piperazine ring.

Also disclosed herein are N-substituted benzyl or N-substituted sulfonylaryl-3-hydroxypyridin-2-(1H)-ones having the formula:

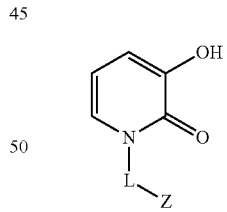

that can be used to stimulate the cellular immune response in a subject. For these compounds, Z and L are the same as disclosed herein above. Non-limiting examples of these compounds include:

1-(4-chlorobenzyl)-3-hydroxypyridin-2(1H)-one having the formula:

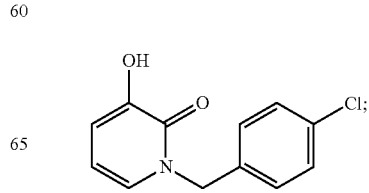

1-(3-chlorobenzyl)-3-hydroxypyridin-2(1H)-one having the formula:

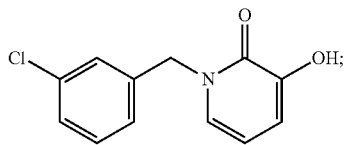 [SMILES: O=c1c(O)cccn1Cc1cccc(Cl)c1]

and 1-(2-chlorobenzyl)-3-hydroxypyridin-2(1H)-one having the formula:

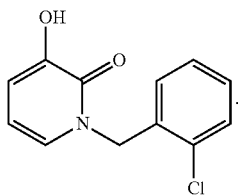 [SMILES: O=c1c(O)cccn1Cc1ccccc1Cl]

Further disclosed herein are N-substituted benzyl or N-substituted sulfonylaryl-5-substituted-3-hydroxypyridin-2-(1H)-ones having the formula:

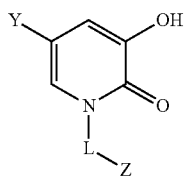

wherein Y is substituted or unsubstituted phenyl, Z and L are the same as defined herein above.

One aspect of Y relates to a phenyl group that is substituted with from 1 to 5 halogen atoms, for example, Y is chosen from 2-chlorophenyl, 3-chlorophenyl, 2-fluorophenyl, 3-fluorophenyl, or 4-fluorophenyl. A further aspect of Y units relates to compounds wherein Y is chosen from 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, and 2,6-dichlorophenyl.

A non-limiting example of compounds according to this category include 1-(4-chlorobenzyl)-5-(4-chlorophenyl)-3-hydroxypyridin-2(1H)-one having the formula:

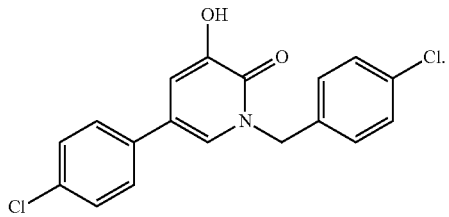 [SMILES: O=c1c(O)cc(-c2ccc(Cl)cc2)cn1Cc1ccc(Cl)cc1]

Further non-limiting examples include:
1-(2-chlorobenzyl)-5-(2-chlorophenyl)-3-hydroxypyridin-2 (1H)-one;
1-(2-chlorobenzyl)-5-(3-chlorophenyl)-3-hydroxypyridin-2 (1H)-one;
1-(2-chlorobenzyl)-5-(4-chlorophenyl)-3-hydroxypyridin-2 (1H)-one;
1-(3-chlorobenzyl)-5-(2-chlorophenyl)-3-hydroxypyridin-2 (1H)-one;
1-(3-chlorobenzyl)-5-(3-chlorophenyl)-3-hydroxypyridin-2 (1H)-one;
1-(3-chlorobenzyl)-5-(4-chlorophenyl)-3-hydroxypyridin-2 (1H)-one;
1-(4-chlorobenzyl)-5-(2-chlorophenyl)-3-hydroxypyridin-2 (1H)-one;
1-(4-chlorobenzyl)-5-(3-chlorophenyl)-3-hydroxypyridin-2 (1H)-one;
1-(2-fluorobenzyl)-5-(2-chlorophenyl)-3-hydroxypyridin-2 (1H)-one;
1-(2-fluorobenzyl)-5-(3-chlorophenyl)-3-hydroxypyridin-2 (1H)-one;
1-(2-fluorobenzyl)-5-(4-chlorophenyl)-3-hydroxypyridin-2 (1H)-one;
1-(3-fluorobenzyl)-5-(2-chlorophenyl)-3-hydroxypyridin-2 (1H)-one;
1-(3-fluorobenzyl)-5-(3-chlorophenyl)-3-hydroxypyridin-2 (1H)-one;
1-(3-fluorobenzyl)-5-(4-chlorophenyl)-3-hydroxypyridin-2 (1H)-one;
1-(4-fluorobenzyl)-5-(2-chlorophenyl)-3-hydroxypyridin-2 (1H)-one;
1-(4-fluorobenzyl)-5-(3-chlorophenyl)-3-hydroxypyridin-2 (1H)-one
1-(4-fluorobenzyl)-5-(4-chlorophenyl)-3-hydroxypyridin-2 (1H)-one
1-(2-chlorobenzyl)-5-(2-fluorophenyl)-3-hydroxypyridin-2 (1H)-one;
1-(2-chlorobenzyl)-5-(3-fluorophenyl)-3-hydroxypyridin-2 (1H)-one;
1-(2-chlorobenzyl)-5-(4-fluorophenyl)-3-hydroxypyridin-2 (1H)-one;
1-(3-chlorobenzyl)-5-(2-fluorophenyl)-3-hydroxypyridin-2 (1H)-one;
1-(3-chlorobenzyl)-5-(3-fluorophenyl)-3-hydroxypyridin-2 (1H)-one;
1-(3-chlorobenzyl)-5-(4-fluorophenyl)-3-hydroxypyridin-2 (1H)-one;
1-(4-chlorobenzyl)-5-(2-fluorophenyl)-3-hydroxypyridin-2 (1H)-one;
1-(4-chlorobenzyl)-5-(3-fluorophenyl)-3-hydroxypyridin-2 (1H)-one;
1-(4-chlorobenzyl)-5-(3-fluorophenyl)-3-hydroxypyridin-2 (1H)-one
1-(2-fluorobenzyl)-5-(2-fluorophenyl)-3-hydroxypyridin-2 (1H)-one;
1-(2-fluorobenzyl)-5-(3-fluorophenyl)-3-hydroxypyridin-2 (1H)-one;
1-(2-fluorobenzyl)-5-(4-fluorophenyl)-3-hydroxypyridin-2 (1H)-one;
1-(3-fluorobenzyl)-5-(2-fluorophenyl)-3-hydroxypyridin-2 (1H)-one;
1-(3-fluorobenzyl)-5-(3-fluorophenyl)-3-hydroxypyridin-2 (1H)-one;
1-(3-fluorobenzyl)-5-(4-fluorophenyl)-3-hydroxypyridin-2 (1H)-one;
1-(4-fluorobenzyl)-5-(2-fluorophenyl)-3-hydroxypyridin-2 (1H)-one;
1-(4-fluorobenzyl)-5-(3-fluorophenyl)-3-hydroxypyridin-2 (1H)-one; and
1-(4-fluorobenzyl)-5-(3-fluorophenyl)-3-hydroxypyridin-2 (1H)-one.

The disclosed compounds are organized into several categories for the strictly non-limiting purpose of describing alternatives for synthetic strategies for the preparation of subgenera of compounds within the scope of the disclosed compounds that are not expressly exemplified herein. This mental organization into categories does not imply anything with respect to increased or decreased biological efficacy with respect to any of the compounds or compositions of matter described herein.

Category I of the disclosed HIF-1α prolyl hydroxylase inhibitors relates to compounds having the formula:

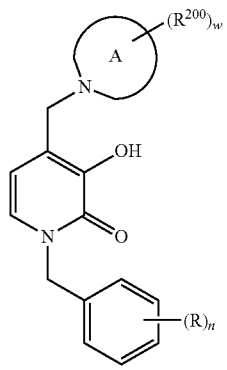

wherein A is a substituted or unsubstituted heterocyclic or heteroaryl ring having from 2 to 20 carbon atoms and from 1 to 7 heteroatoms, $R^{200}$ represents from 0 to 40 substitutions form hydrogen, R represents from 1 to 5 substitutions for hydrogen as defined herein above, and the index n is from 1 to 5. Table I provides representative examples of compounds according to this category.

TABLE I

| No. | R | A ring |
|---|---|---|
| A1 | 3-methoxy | pyrrolidin-1-yl |
| A2 | 3-methoxy | 3-hydroxypyrrolidin-1-yl |
| A3 | 3-methoxy | 2-(pyrdin-2-yl)pyrrolidin-1-yl |
| A4 | 3-methoxy | 2-methylcarboxypyrrolidin-1-yl |
| A5 | 3-methoxy | 2-(methoxymethyl)pyrrolidin-1-yl |
| A6 | 3-methoxy | thiazolidin-3-yl |
| A7 | 3-methoxy | 1H-imidazol-1-yl |
| A8 | 3-methoxy | piperidin-1-yl |
| A9 | 3-methoxy | 4-benzylpiperidin-1-yl |
| A10 | 3-methoxy | 1,4'-bipiperidinyl-1'-yl |
| A11 | 3-methoxy | piperazin-1-yl |
| A12 | 3-methoxy | 4-benzylpiperazin-1-yl |
| A13 | 3-methoxy | 4-(2-methoxyphenyl)piperazin-1-ylmethyl |
| A14 | 3-methoxy | 4-(6-chloropyridazin-3-yl)piperazin-1-yl |
| A15 | 3-methoxy | 1,4-dioxa-8-azaspiro[4,5]dec-8-yl |
| A16 | 3-methoxy | morpholin-4-yl |
| A17 | 3-methoxy | thiomorpholin-4-yl |
| A18 | 3-methoxy | azepan-l-yl |
| A19 | 3-methoxy | azocan-1-yl |
| A20 | 3-methoxy | 3,4-dihydroquinolin-1(2H)-yl |
| A21 | 4-chloro | pyrrolidin-1-yl |
| A22 | 4-chloro | 3-hydroxypyrrolidin-1-yl |
| A23 | 4-chloro | 2-(pyrdin-2-yl)pyrrolidin-1-yl |
| A24 | 4-chloro | 2-methylcarboxypyrrolidin-1-yl |
| A25 | 4-chloro | 2-(methoxymethyl)pyrrolidin-1-yl |
| A26 | 4-chloro | thiazolidin-3-yl |
| A27 | 4-chloro | 1H-imidazol-1-yl |
| A28 | 4-chloro | piperidin-1-yl |
| A29 | 4-chloro | 4-benzylpiperidin-1-yl |
| A30 | 4-chloro | 1,4'-bipiperidinyl-1'-yl |
| A31 | 4-chloro | piperazin-1-yl |
| A32 | 4-chloro | 4-benzylpiperazin-1-yl |
| A33 | 4-chloro | 4-(2-methoxyphenyl)piperazin-1-ylmethyl |

TABLE I-continued

| No. | R | A ring |
|---|---|---|
| A34 | 4-chloro | 4-(6-chloropyridazin-3-yl)piperazin-1-yl |
| A35 | 4-chloro | 1,4-dioxB-8-azaspiro[4,5]dec-8-yl |
| A36 | 4-chloro | morpholin-4-yl |
| A37 | 4-chloro | thiomorpholin-4-yl |
| A38 | 4-chloro | azepan-1-yl |
| A39 | 4-chloro | azocan-1-yl |
| A40 | 4-chloro | 3,4-dihydroquinolin-1(2H)-yl |
| A41 | 4-chloro | 4-tert-butoxycarbonylpiperazin-1-yl |

The disclosed compounds of this category can be prepared by the procedure outlined herein below in Scheme I and described in Example 1.

Scheme I

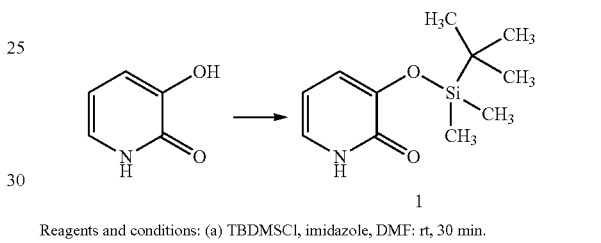

Reagents and conditions: (a) TBDMSCl, imidazole, DMF: rt, 30 min.

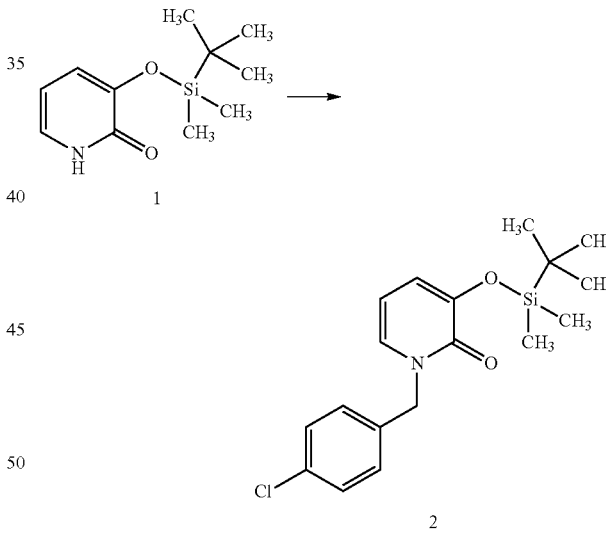

Reagents and conditions: (b) (4-chloro)benzyl chloride, Cs₂CO3, THF; rt.

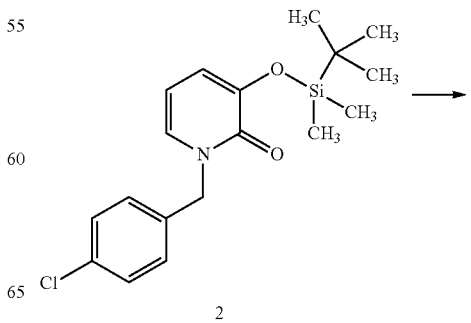

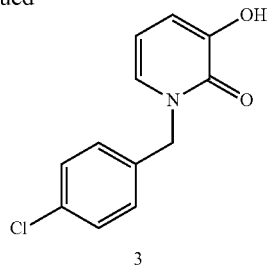

Reagents and conditions: (c) 5M HCl, EtOH; 30 min.

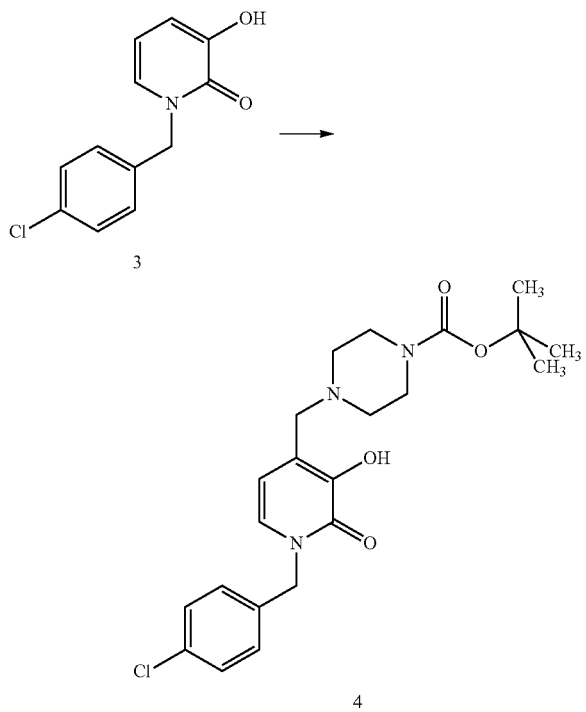

Reagents and conditions: (d)(i) H₂CHO, AcOH, t-Boc-piperazine, EtOH; 3 days.

EXAMPLE 1 tert-Butyl-{[1-(4-chlorobenzyl)-3-hydroxy-2-oxo-1, 2-dihydropyridin-4-yl]methyl}piperazine-1-carboxylate (4)

Preparation of 3-(tert-butyldimethylsilanyloxy)-1H-pyridin-2-one (1): 3-Hydroxypyridin-2(1H)-one (15 g, 135 mmol) and imidazole (23 g, 338 mmol) were suspended in dimethylformamide (200 mL) under inert atmosphere. A solution of tert-butyldimethylsilyl chloride (20.5 g, 136 mmol) in dimethylformamide (200 mL) is added dropwise at room temperature over 30 minutes. The reaction was then allowed to stir overnight. The resulting solution was then poured into water (300 mL) and the mixture extracted with tert-butyl methyl ether (3×500 mL). The combined organic layer was washed with water (300 mL), brine (300 mL) then dried over Na₂SO₄. The solvent is removed under reduced pressure and the crude product crystallized from heptanes to afford 16.3 g (53% yield) of the desired product. ¹H NMR (250 MHz, CDCl₃) δ ppm 12.98 (1H, m); 6.91 (1H, dd, J=1. Hz, J=6.8 Hz); 6.81 (1H, dd, J=1.8 Hz, J=7.2 Hz); 6.02-6.007 (1H, m); 0.90 (9H, s), and 0.17 (6H, s).

Preparation of 3-(tert-butyldimethylsilanyloxy)-1-(3-chlorobenzyl)-1H-prydin-2-one (2): At 0° C. under an inert atmosphere, a solution of 4-chlorobenzyl chloride (4.44 mmol) in THF (10 mL) was added dropwise to a solution of 3-(tert-butyldimethylsilanyloxy)-1H-pyridin-2-one, 1, (1 g, 4.44 mmol) and CsCO₃ (2.17 g, 6.66 mmol) in THF (10 mL). The reaction solution was allowed to warm to room temperature and stirring was continued overnight. The resulting solution was diluted with water (40 mL) and then extracted with EtOAc (3×30 mL). The combined organic layer was washed with brine (30 mL) then dried over Na₂SO₄. The solvent is removed under reduced pressure and the crude product purified over silica (EtOAc:heptane 4:1) to afford the desired product as a white solid.

Preparation of 1-(4-chlorobenzyl)-3-hydroxypyridin-2 (1H)-one (3): To a solution of 3-(tert-butyldimethylsilanyloxy)-1-(3-chlorobenzyl)-1H-prydin-2-one, 2, (2.36 g, 10 mmol) in EtOAc (25 mL) as added 5 M HCl (25 mL) with vigorous stirring at room temperature. The reaction was monitored by TLC for the disappearance of starting material and was complete within 30 minutes. The organic layer was decanted and the aqueous phase extracted with dichloromethane (2×50 mL). The combined organic layers were dried over Na₂SO₄ and the solvent removed under reduced pressure. The crude product was recrystallized from dichloromethane. The yield was nearly quantitative. ¹H NMR (360 MHz, DMSO-d₆) δ ppm 5.12 (2H, s); 6.13 (1H, t, J=7.04); 6.71 (1H, dd, J=7.04, 1.59); 7.23-7.28 (2H, m); 7.36-7.43 (2H, m); 9.10 (1H, br. s).

Preparation of tert-butyl-{[1-(4-chlorobenzyl)-3-hydroxy-2-oxo-1,2-dihydro-pyridin-4-yl]methyl}piperazine-1-carboxylate (4): tert-Butyl piperazine-1-carboxylate (97.6 mmol), formaldehyde (8 mL of a 37% soln., 97.6 mmol) and acetic acid (8 mL) were dissolved in ethanol (350 mL) and the solution stirred for 1 hour at room temperature. A solution of 1-(4-chlorobenzyl)-3-hydroxypyridin-2(1H)-one, 3, (48.8 mmol) in ethanol (350 mL) was added dropwise over 30 minutes. After 3 days of stirring, formaldehyde (3 mL) was added and the reaction heated to 50° C. after which the reaction solution was concentrated under reduced pressure to approximately 500 mL. The desired product is obtained by crystallization from ethanol. ¹H NMR (250 MHz, CDCl₃) d ppm 1.46 (s, 9H); 2.38-2.57 (m, 4H); 3.40-3.49 (m, 4H); 3.51 (s, 2H); 5.13 (s, 2H); 6.13 (d, J=7.16 Hz), 1H); 6.79 (d, J=7.16 Hz, 1H); 7.20-7.41 (m, 4H); 8.33-8.85 (m, 1H).

Category II of the disclosed prolyl hydroxylase inhibitors relates to compounds having the formula:

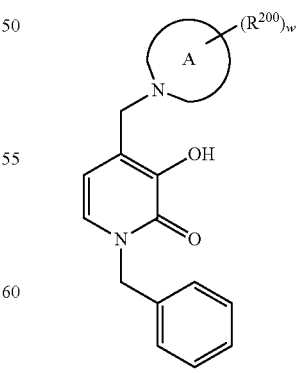

wherein A is a substituted or unsubstituted heterocyclic or heteroaryl ring having from 2 to 20 carbon atoms and from 1 to 7 heteroatoms, and R²⁰⁰ represents from 0 to 40 substitutions form hydrogen. Table II provides representative examples of compounds according to this category.

TABLE II

| No. | A ring |
|---|---|
| B1 | pyrrolidin-1-yl |
| B2 | 3-hydroxypyrrolidin-1-yl |
| B3 | 2-(pyrdin-2-yl)pyrrolidin-1-yl |
| B4 | 2-methylcarboxypyrrolidin-1-yl |
| B5 | 2-(methoxymethyl)pyrrolidin-1-yl |
| B6 | thiazolidin-3-yl |
| B7 | 1H-imidazol-1-yl |
| B8 | piperidin-1-yl |
| B9 | 4-benzylpiperidin-1-yl |
| B10 | 1,4'-bipiperidinyl-1'-yl |
| B11 | piperazin-1-yl |
| B12 | 4-benzylpiperazin-1-yl |
| B13 | 4-(2-methoxyphenyl)piperazin-1-ylmethyl |
| B14 | 4-(6-chloropyridazin-3-yl)piperazin-1-yl |
| B15 | 1,4-dioxa-8-azaspiro[4,5]dec-8-yl |
| B16 | morpholin-4-yl |
| B17 | thiomorpholin-4-yl |
| B18 | azepan-1-yl |
| B19 | azocan-1-yl |
| B20 | 3,4-dihydroquinolin-1(2H)-yl |

The compounds according to Category II can be prepared according to the procedure outlined in Scheme I and disclosed in Example 1. The following are further examples of inhibitors according to Category II.

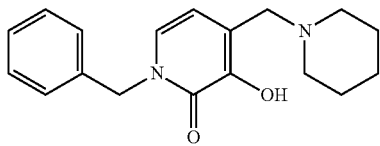 [SMILES: O=c1c(O)c(CN2CCCCC2)ccn1Cc1ccccc1]

1-Benzyl-3-hydroxy-4-(piperidin-1-ylmethyl)pyridin-2 (1H)-one: $^1$H NMR (300 MHz, CD$_3$OD) δ 1.81 (m, 6H), 3.07 (m, 2H), 3.51 (m, 2H), 4.23 (s, 2H), 5.24 (s, 2H), 6.31 (d, J=6.9 Hz, 1H), 7.35 (m, 6H); $^{19}$F NMR (252 MHz, CD$_3$OD) δ 85.5; 13C NMR (75 MHz, DMSO) δ 21.3, 22.7, 51.8, 52.5, 53.1, 106.4, 117.4, 127.7, 128.0, 128.2, 128.9, 137.3, 147.4, 158.0; ES MS(M+1) 299.12; HRMS Calcd. For C$_{18}$H$_{22}$N$_2$O$_2$, 298.38. Found (M+1) 299.17.

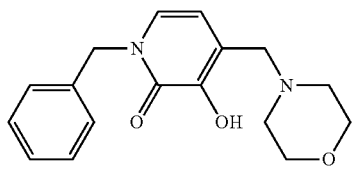

1-Benzyl-3-hydroxy-4-(morpholin-4-ylmethyl)pyridin-2 (1H)-one: $^1$H NMR (300 MHz, DMSO) δ 3.25 (m, 4H), 3.81 (m, 4H), 4.18 (s, 2H), 5.17 (s, 2H), 6.31 (d, J=6.9 Hz, 1H), 7.35 (m, 6H); $^{19}$FNMR (300 MHz, DMSO) δ 88.5; $^{13}$C NMR (300 MHz, DMSO) δ 51.6, 51.8, 53.4, 63.5, 107.9, 119.1, 127.8, 128.0, 128.2, 128.9, 137.3, 147.5, 158.3; ES MS(M+1) 301.12; HRMS Calcd. For C$_{17}$H$_{20}$N$_2$O$_3$, 300.35.

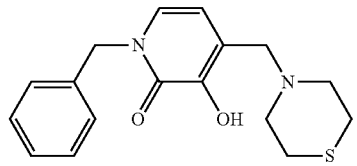 [SMILES: O=c1c(O)c(CN2CCSCC2)ccn1Cc1ccccc1]

1-Benzyl-3-hydroxy-4-(thiomorpholin-4-ylmethyl)pyridin-2(1H)-one: $^1$HNMR (300 MHz, DMSO) δ 2.92 (m, 4H), 3.38 (m, 4H), 4.17 (s, 2H), 5.16 (s, 2H), 6.29 (d, J=7.5 Hz, 1H), 7.34 (m, 6H), 9.97 (s, 1H); $^{19}$F NMR (300 MHz, DMSO) δ 88.4; $^{13}$C NMR (75 MHz, DMSO) δ 24.3, 51.9, 53.4, 53.7, 107.9, 110.9, 127.8, 128.0, 128.2, 128.8, 137.2, 147.6, 157.6; ES MS (M+1) 317.14; HRMS Calcd. For C$_{17}$H$_{20}$N$_2$O$_2$S, 316.42. Found: (M+1) 317.13.

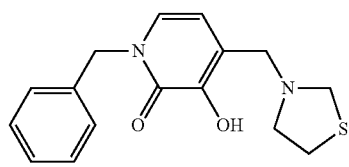 [SMILES: O=c1c(O)c(CN2CCSC2)ccn1Cc1ccccc1]

1-Benzyl-3-hydroxy-4-(thiazolidin-3-ylmethyl)pyridin-2 (1H)-one: $^1$HNMR (300 MHz, DMSO) δ 3.09 (t, J=6.3 Hz, 2H), 3.42 (t, J=6.3 Hz, 2H), 4.03 (s, 2H), 4.29 (s, 2H), 5.16 (s, 2H), 6.34 (d, J=7.2 Hz, 1H), 7.34 (m, 6H), 10.48 (broad s, 1H); $^{19}$FNMR (300 MHz, DMSO) δ 87.9; $^{13}$CNMR (75 MHz, DMSO) δ 28.3, 48.3, 50.1, 56.3, 57.0, 107.4, 122.1, 127.8, 128.2, 128.8, 137.4, 146.3, 157.6; ES MS (M+1) 303.08; Anal. Calcd for C$_{18}$H$_{19}$N$_2$O$_4$SF, C, 51.92; H, 4.60; N, 6.73; S, 7.70. Found: C, 51.67; H, 4.48; N, 6.69; S, 7.65.

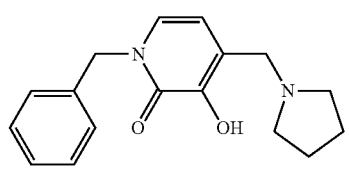 [SMILES: O=c1c(O)c(CN2CCCC2)ccn1Cc1ccccc1]

1-Benzyl-3-hydroxy-4-(pyrrolidin-1-ylmethyl)pyridin-2 (1H)-one: $^1$H NMR (300 MHz, DMSO) δ 1.96 (s, 4H), 3.16 (s, 2H), 3.43 (s, 2H), 4.23 (s, 4H), 5.17 (s, 2H), 6.34 (d, J=7.2 Hz, 1H), 7.34 (m, 6H); $^{19}$F NMR (252 MHz, DMSO) δ 88.7; $^{13}$C NMR (75 MHz, DMSO) δ 22.8, 50.9, 51.8, 53.7, 107.3, 118.0, 128.0, 128.2, 128.9, 137.3, 146.7, 157.6; ES MS (M+1) 285.13; Anal. Calcd. For C$_{19}$H$_{21}$F$_3$N$_2$O$_4$, C, 57.28; H, 5.31; N, 7.03. Found: C, 57.10; H, 5.11; N, 7.02.

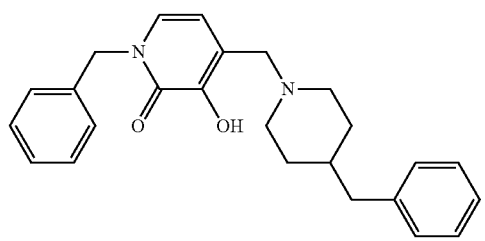 [SMILES: O=c1c(O)c(CN2CCC(Cc3ccccc3)CC2)ccn1Cc1ccccc1]

1-Benzyl-3-hydroxy-4-(4-benzylpiperidin-1-ylmethyl) pyridin-2(1H)-one: $^1$H NMR (DMSO) δ 1.43 (m, 2H), 1.72

(m, 4H), 2.96 (m, 2H), 3.41 (m, 3H), 4.09 (s, 2H), 5.16 (s, 2H), 6.34 (d, J=7.2 Hz, 1H), 7.35 (m, 11H); $^{19}$F NMR (252 MHz, DMSO) δ 88.8; $^{13}$C NMR (75 MHz, DMSO) δ; ES MS(M+1) 389.21; HRMS Calcd. For $C_{25}H_{28}N_2O_2$, 388.50. Found (M+1) 389.22.

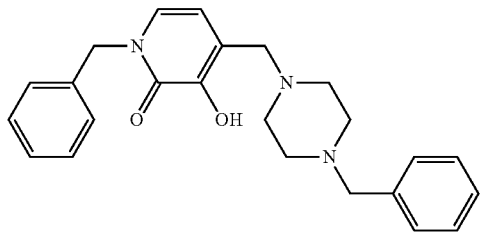 [SMILES: O=c1c(O)c(CN2CCN(Cc3ccccc3)CC2)ccn1Cc1ccccc1]

1-Benzyl-3-hydroxy-4-(4-benzylpiperazin-1-ylmethyl)pyridin-2(1H)-one: $^1$H NMR (300 MHz, DMSO) δ 3.11 (broad s, 4H), 3.81 (s, 2H), 4.18 (s, 2H), 5.15 (s, 2H), 6.24 (d, J=7.2 Hz, 1H), 7.34 (m, 6H), 7.46 (m, 5H); $^{19}$F NMR (252 MHz, DMSO) δ 88.2; 13C (75 MHz, DMSO) δ; ES MS(M+1) 390.21; HRMS Calcd. For $C_{24}H_{27}N_3O_2$, 389.49. Found (M+1) 390.21.

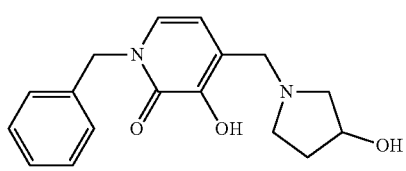 [SMILES: O=c1c(O)c(CN2CCC(O)C2)ccn1Cc1ccccc1]

1-Benzyl-3-hydroxy-4-[(3-hydroxypyrrolidin-1-yl)methyl]pyridin-2(1H)-one: $^1$HNMR (300 MHz, DMSO) δ 1.90 (m, 1H), 3.18 (m, 2H), 3.47 (m, 3H), 4.24 (s, 2H), 4.43 (s, 1H), 5.17 (s, 2H), 6.34 (d, J=7.2 Hz, 1H), 7.34 (m, 6H); $^{19}$F NMR (252 MHz, DMSO) δ 89.0; $^{13}$C NMR (75 MHz, DMSO) δ 51.8, 52.6, 61.3, 68.6, 107.4, 117.9, 128.0, 128.2, 128.9, 137.3, 146.7, 157.6; ES MS(M+1) 301.13; HRMS Calcd. For $C_{17}H_{20}N_2O_3$, 300.35. Found: (M+1) 301.15.

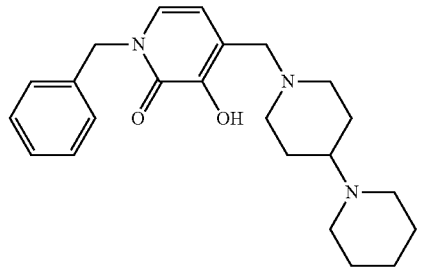

1-Benzyl-3-hydroxy-4-(1,4-dioxa-8-azaspiro[4,5]dec-8-ylmethyl)pyridin-2(1H)-one: $^1$H NMR (300 MHz, DMSO) δ 1.90 (m, 4H), 3.11 (m, 2H), 3.43 (m, 2H), 3.93 (s, 4H), 4.19 (s, 2H), 5.16 (s, 2H), 6.34 (d, J=7.2 Hz, 1H), 7.34 (m, 6H), 10.01 (broad s, 1H); $^{19}$F NMR (252 MHz, DMSO) δ 88.3; $^{13}$C NMR (75 MHz, DMSO) δ 31.7, 50.7, 51.9, 52.5, 64.5, 101.1, 108.0, 116.5, 127.8, 128.0, 128.3, 128.9, 137.3, 147.5 157.6; ES MS(M+1) 357.19; HRMS Calcd. For $C_{20}H_{24}N_4O_2$, 356.42. Found (M+1) 357.18.

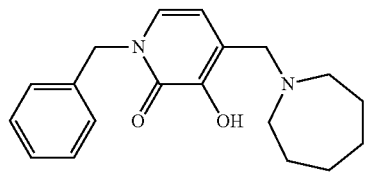 [SMILES: O=c1c(O)c(CN2CCCCCC2)ccn1Cc1ccccc1]

1-Benzyl-3-hydroxy-4-azepan-1-ylmethylpyridin-2(1H)-one: $^1$H NMR (300 MHz, DMSO) δ 1.61 (m, 4H), 1.80 (m, 4H), 3.20 (m, 4H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ 22.8, 26.4, 51.8, 53.4, 54.4, 107.6, 117.2, 127.9, 128.0, 18.2, 128.9, 137.3, 147.2, 157.6; ES MS(M+1) 313.18; HRMS Calcd. For $C_{19}H_{24}N_2O_4$, 312.41. Found (M+1) 313.19.

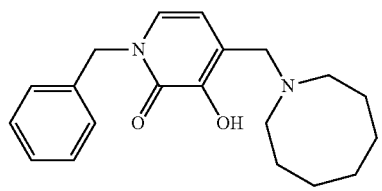 [SMILES: O=c1c(O)c(CN2CCCCCCC2)ccn1Cc1ccccc1]

1-Benzyl-3-hydroxy-4-(azocan-1-ylmethyl)pyridin-2(1H)-one: $^1$H NMR (300 MHz, DMSO) δ 1.59 (m, 10H), 3.18 (m, 2H), 3.38 (m, 2H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ; ES MS(M+1) 327.2; HRMS Calcd. For $C_{20}H_{26}N_2O_2$, 326.43. Found (M+1) 327.20.

1-Benzyl-3-hydroxy-(1,4'-bipiperidinyl-1'-ylmethyl)pyridin-2(1H)-one: $^1$H NMR (300 MHz, DMSO) δ 1.43-1.98 (m, 10H), 2.21 (m, 2H), 3.01 (m, 4H), 3.43 (m, 3H), 4.12 (s, 2H), 5.16 (s, 2H), 6.34 (d, J=7.2 Hz, 1H), 7.34 (m, 6H), 9.85 (broad s, 1H); $^{19}$F NMR (252 MHz, DMSO) δ 88.7; $^{13}$C NMR (75 MHz, DMSO) δ 21.6, 22.9, 23.8, 49.6, 50.5, 51.8, 53.0, 59.5, 108.0, 127.8, 128.0, 128.2, 128.9, 137.3, 147.5, 157.6; ES MS(M+1) 382.4; HRMS Calcd. For $C_{23}H_{31}N_3O_2$, 383.51. Found (M+1) 382.25.

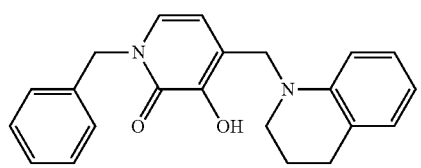 [SMILES: O=c1c(O)c(CN2CCCc3ccccc32)ccn1Cc1ccccc1]

1-Benzyl-3-hydroxy-4-[(3,4-dihydroquinolin-1(2H)-yl)methyl]pyridin-2(1H)-one: $^1$H NMR (300 MHz, DMSO) δ 3.13 (t, J=6.3 Hz, 2H), 3.52 (m, 2H), 4.28 (s, 2H), 4.41 (s, 2H), 5.18 (s, 2H), 6.34 (d, J=7.2 Hz, 1H), 7.23-7.41 (m, 10H), 10.15 (broad s, 1H); $^{19}$F NMR (252 MHz, DMSO) δ 88.9; $^{13}$C NMR (75 MHz, DMSO) δ 25.4; 49.3, 51.8, 52.7, 52.9, 107.6, 11.6, 116.8, 126.9, 127.0, 127.9, 128.0, 128.1, 128.2, 128.8, 128.9, 131.7, 137.3, 147.3, 157.6; ES MS(M+1) 347.40; HRMS Calcd. For $C_{22}H_{22}N_2O_2$, 346.42. Found (M+1) 347.17.

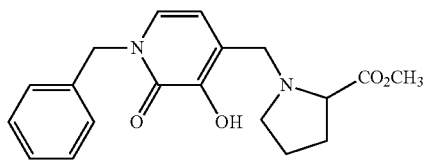 [SMILES: COC(=O)C1CCCN1Cc1ccn(Cc2ccccc2)c(=O)c1O]

Methyl 1-[(1-benzyl-3-hydroxy-2-oxo-1,2-dihydropyridin-4-yl)methyl]pyrrolidine-2-carboxylate: $^1$H NMR (300 MHz, DMSO) δ 2.01 (m, 3H), 2.45 (m, 1H), 3.26 (m, 1H), 3.53 (m, 1H), 3.69 (s, 3H), 4.30 (m, 3H), 5.17 (s, 2H), 6.27 (d, 6.9 Hz, 1H), 7.35 (m, 6H), $^{19}$F NMR (252 MHz, DMSO) δ 88.3; 13C NMR (75 MHz, DMSO) α; ES MS(M+1) 343.20; HRMS Calcd. For $C_{19}H_{22}N_2O_4$, 342.39. Found (M+1).

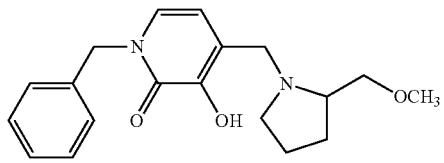 [SMILES: COCC1CCCN1Cc1ccn(Cc2ccccc2)c(=O)c1O]

1-benzyl-3-hydroxy-4-{[2-(methoxymethyl)pyrrolidin-1-yl]methyl}pyridin-2(1H)-one: $^1$H NMR (300 MHz, DMSO) δ 1.71 (m, 1H), 1.84 (m, 1H), 1.99 (m, 1H), 2.15 (m, 1H), 3.19 (m, 1H), 3.30 (s, 3H), 3.41 (m, 1H), 3.62 (m, 2H), 3.77 (m, 1H), 4.15 (m, 1H), 4.39 (m, 1H), 5.17 (s, 2H), 6.34 (d, J=7.2 Hz, 1H), 7.34 (m, 6H); 9.60 (broad s, 1H); $^{19}$F NMR (252 MHz, DMSO) δ 88.3; $^{13}$C NMR (75 MHz, DMSO) δ; ES MS(M+1) 329.2; HRMS Calcd. For $C_{19}H_{24}N_2O_3$, 328.41. Found (M+1).

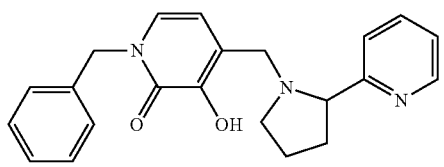 [SMILES: O=c1c(O)c(CN2CCCC2c2ccccn2)ccn1Cc1ccccc1]

1-Benzyl-3-hydroxy-4-{[2-(pyrdin-2-yl)pyrrolidin-1-yl]methyl}pyridin-2(1H)-one: $^1$H NMR (300 MHz, DMSO) δ 2.12 (m, 4H), 3.39 (m, 1H), 3.63 (m, 1H), 4.07 (m, 2H), 4.60 (m, 1H), 5.10 (m, 2H), 6.15 (d, J=6.9 Hz, 1H), 7.33 (m, 6H), 7.44 (m, 1H), 8.05 (d, J=8.1 Hz, 1H), 8.59 (d, J=4.8 Hz, 1H), 8.74 (s, 1H); $^{19}$F NMR (252 MHz, DMSO) δ 88.0; ES MS(M+1) 362.22; HRMS Calcd. For $C_{22}H_{23}N_3O_2$, 361.44. Found (M+1).

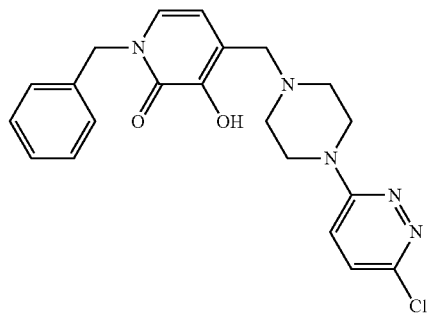 [SMILES: O=c1c(O)c(CN2CCN(c3ccc(Cl)nn3)CC2)ccn1Cc1ccccc1]

1-Benzyl-3-hydroxy-4-[4-(6-chloropyridazin-3-yl)piperazin-1-ylmethyl]pyridin-2(1H)-one: $^1$H NMR (300 MHz, DMSO) δ 3.18 (m, 2H), 3.48 (m, 4H), 4.19 (s, 2H), 4.46 (m, 2H), 5.16 (s, 2H), 6.62 (d, J=7.2 Hz, 1H), 7.35 (m, 6H), 7.48 (m, 1H), 7.68 (m, 1H), 11.5 (broad s, 1H); $^{13}$C NMR (75 MHz, DMSO) δ 42.1, 50.3, 51.9, 52.5, 108.2, 116.2; 118.0, 128.0, 128.2, 128.9, 129.8, 137.3, 147.4, 157.6, 158.8; ES MS(M+1) 476.09. HRMS Calcd. For $C_{21}H_{22}ClN_5N_3O_2$, 411.88. Found (M+1) 412.76.

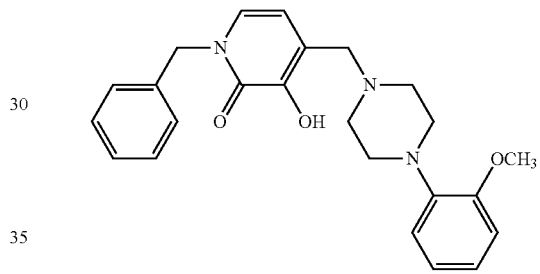

1-Benzyl-3-hydroxy-4-[4-(2-methoxyphenyl)piperazin-1-ylmethyl]pyridin-2(1H)-one: $^1$H NMR (300 MHz, DMSO) δ 2.95 (m, 2H), 3.30 (m, 2H), 3.48 (m, 4H), 3.80 (s, 3H), 4.25 (s, 2H), 5.18 (s, 2H), 6.34 (d, J=7.2 Hz, 1H), 6.93 (m, 2H), 7.01 (m, 2H), 7.34 (m, 6H); $^{19}$F NMR (252 MHz, DMSO) δ 88.5; 13C NMR (75 MHz, DMSO) δ 47.2, 51.8, 53.0, 55.3, 108.1, 112.2, 114.8, 116.2, 118.6, 121.2, 123.8, 127.8, 128.0, 128.9, 137.3, 139.6, 147.5, 152.2, 157.6; ES MS(M+1) 405.82; HRMS Calcd. For $C_{24}H_{27}N_3O_3$, 405.49. Found (M+1) 406.21.

Category III of the disclosed prolyl hydroxylase inhibitors relates to compounds having the formula:

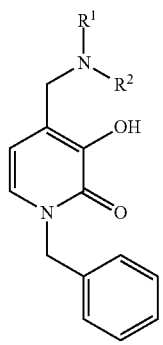

$R^1$ and $R^2$ are each independently hydrogen or substituted or unsubstituted $C_1$-$C_{10}$ linear or branched alkyl, wherein the alkyl unit can be substituted by one or more units independently chosen from:

i) $C_1$-$C_8$ linear, $C_3$-$C_8$ branched, or $C_3$-$C_8$ cyclic alkoxy;

ii) hydroxy;

iii) halogen;

iv) cyano;

v) amino, $C_1$-$C_8$ mono-alkylamino, $C_1$-$C_8$ di-alkylamino;

vi) —$SR^{40}$; $R^{40}$ is hydrogen or $C_1$-$C_4$ linear or $C_3$-$C_4$ branched alkyl;

vii) substituted or unsubstituted $C_6$ of $C_{10}$ aryl;

viii) substituted or unsubstituted $C_1$-$C_9$ heterocyclic; or ix) substituted or unsubstituted $C_1$-$C_9$ heteroaryl.

Table III herein below provides non-limiting examples of compounds encompassed by this category.

TABLE III

| No. | $R^1$ | $R^2$ |
|---|---|---|
| C1 | benzyl | hydrogen |
| C2 | 4-methoxybenzyl | hydrogen |
| C3 | 4-fluorobenzyl | hydrogen |
| C4 | 4-chlorobenzyl | hydrogen |
| C5 | 4-methylbenzyl | hydrogen |
| C6 | 2-(pyridin-2-yl)ethyl | hydrogen |
| C7 | [1,3]dioxolan-2-ylmethyl | hydrogen |
| C8 | tetrahydrofuran-2-ylmethyl | hydrogen |
| C9 | 2-methoxyethyl | hydrogen |
| C10 | 1-hydroxy-2-methylpropan-2-yl | hydrogen |
| C11 | pyridin-4-ylmethyl | hydrogen |
| C12 | furan-2-ylmethyl | hydrogen |
| C13 | 2-(methylthio)ethyl | hydrogen |
| C14 | 1-phenylethyl | hydrogen |
| C15 | 3-imidazol-1-ylpropyl | hydrogen |
| C16 | cycloheptyl | hydrogen |
| C17 | 4-methylcyclohexyl | hydrogen |
| C18 | 1-benzylpiperidin-4-yl | hydrogen |
| C19 | azepan-2-on-3-yl | hydrogen |
| C20 | 1-benzylpyrrolidin-3-yl | hydrogen |
| C21 | benzyl | methyl |
| C22 | 4-methoxybenzyl | methyl |
| C23 | 4-fluorobenzyl | methyl |
| C24 | 4-chlorobenzyl | methyl |
| C25 | 4-methylbenzyl | methyl |
| C26 | 2-(pyridin-2-yl)ethyl | methyl |
| C27 | [1,3]dioxolan-2-ylmethyl | methyl |
| C28 | tetrahydrofuran-2-ylmethyl | methyl |
| C29 | 2-methoxyethyl | methyl |
| C30 | 1-hydroxy-2-methylpropan-2-yl | methyl |
| C31 | pyridin-4-ylmethyl | methyl |
| C32 | furan-2-ylmethyl | methyl |
| C33 | 2-(methylthio)ethyl | methyl |
| C34 | 1-phenylethyl | methyl |
| C35 | 3-(1H-imidazol-1-yl)propyl | methyl |
| C36 | cycloheptyl | methyl |
| C37 | 4-methylcyclohexyl | methyl |
| C38 | 1-benzylpiperidin-4-yl | methyl |
| C39 | azepan-2-on-3-yl | methyl |
| C40 | 1-benzylpyrrolidin-3-yl | methyl |

The disclosed compounds of this category can be prepared by the procedure outlined herein below in Scheme II and described in Example 2.

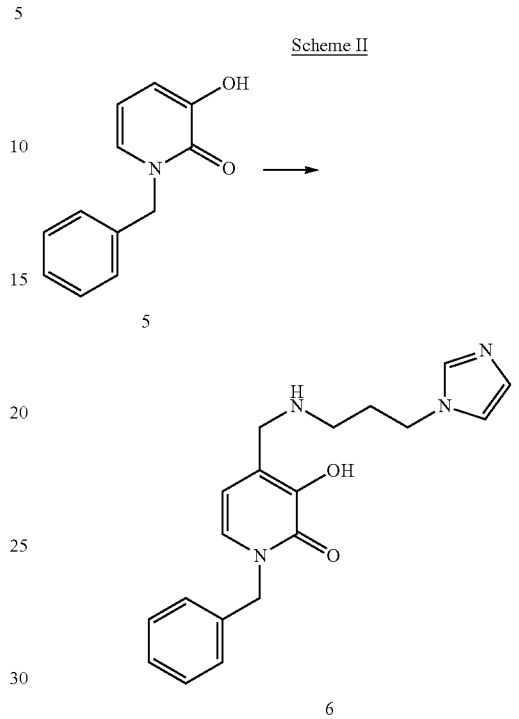

Scheme II

Reagants and conditions: (a)(i) HCHO, EtOH; 0.5 hr (ii) 3-(1-H-imidazol-1-yl) propan-1-amine; 2 hr.

EXAMPLE 2

1-Benzyl-3-hydroxy-4-{[3-(1-H-imidazol-1-yl)propylamino]methyl}-pyridin-2(1H)-one (6)

N-Benzyl-3-hydroxypyridin-2(1H)-one (5) can be prepared according to Example 1 by substituting benzyl bromide or benzyl chloride into step (b) for (4-chloro)benzyl chloride.

1-Benzyl-3-hydroxy-4-{[3-(1-H-imidazol-1-yl)propylamino]methyl}pyridin-2(1H)-one (6): N-Benzyl-3-hydroxypyridin-2(1H)-one (5) (250 mg, 1.23 mmol) and formaldehyde (200 mg, 273 eq.) are combined in aqueous ethanol (10 mL) and stirred for 30 minutes. 3-(1-H-Imidazol-1-yl) propan-1-amine (340 mg, 2.7 mmol) is then added and the reaction stirred for 12 hours. The solvent is removed by evaporation and the residue dissolved in methanol (2 mL) and purified via prep HPLC eluting with water/acetonitrile to afford the desired product as the trifluoroacetate salt. $^1$H NMR (300 MHz, DMSO) δ 2.19 (m, 2H), 2.97 (m, 2H), 4.02 (s, 2H), 4.30 (t, J=6.6 Hz, 2H); 5.17 (s, 2H), 6.30 (d, J=6.9 Hz, 1H), 7.36 (m, 6H), 7.26 (s, 1H), 7.76 (s, 1H), 9.03 (s, 1H), 9.11 (s, 1H); $^{19}$F NMR (252 MHz, DMSO) δ 88.5; $^{13}$C NMR (75 MHz, DMSO) δ 26.5, 44.0, 46.0, 51.8, 106.8, 118.7, 120.5, 122.2, 127.9, 128.2, 128.9, 135.8, 137.4, 146.0, 158.2; ES MS(M+1) 339.05; HRMS Calcd. For $C_{19}H_{22}N_4O_2$, 338.44. Found (M+1) 339.18.

The following are further non-limiting examples of this aspect of the disclosed HIF-1α prolyl hydroxylase inhibitors.

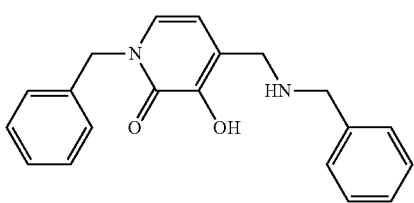 [SMILES: O=c1c(O)c(CNCc2ccccc2)ccn1Cc1ccccc1]

1-Benzyl-3-hydroxy-4-(benzylaminomethyl)pyridin-2(1H)-one: $^1$HNMR (300 MHz, DMSO) δ 4.01 (s, 2H), 4.20 (s, 2H), 5.16 (s, 2H), 6.34 (d, J=7.2 Hz, 1H), 7.36 (m, 11H), 9.16 (broad s, 1H); $^{19}$FNMR (252 MHz, DMSO) δ 88.6; $^{13}$C NMR (75 MHz, DMSO) α; ES MS(M+1) 321.16; Anal. Calcd. For $C_{22}H_{21}F_3N_2O_4$, C, 60.83; H, 4.87; N, 6.45. Found: C, 60.75; H, 4.56; N, 6.34.

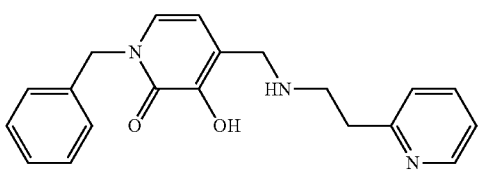 [SMILES: O=c1c(O)c(CNCCc2ccccn2)ccn1Cc1ccccc1]

1-Benzyl-3-hydroxy-4-{[(2-(pyridin-2-yl)ethylamino]methyl}pyridin-2(1H)-one: $^1$H NMR (300 MHz, DMSO) δ 3.26 (m, 2H), 3.37 (m, 2H), 4.08 (s, 2H), 5.17 (s, 2H); 6.34 (d, J=7.2 Hz, 1H), 7.38 (m, 6H), 7.86 (d, J=5.7 Hz, 2H), 8.84 (m, 2H), 9.32 (broad s, 1H); $^{19}$FNMR (252 MHz, DMSO) δ 88.6; $^{13}$C NMR (75 MHz, DMSO) δ 31.5, 44.1, 46.3, 51.8, 106.9, 114.8, 127.1, 128.1, 128.8, 137.4, 143.8, 146.1, 155.3, 157.5, 158.4; ES MS (M+1) 336.18; HRMS Calcd For $C_{20}H_{21}N_3O_2$, 335.40. Found: 336.16.

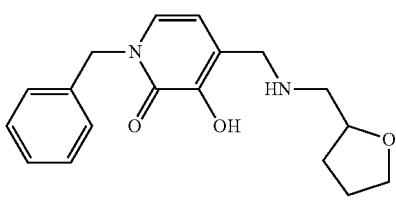 [SMILES: O=c1c(O)c(CNCC2CCCO2)ccn1Cc1ccccc1]

1-Benzyl-3-hydroxy-4-{[(tetrahydrofuran-2-ylmethyl)amino]methyl}pyridin-2(1H)-one: $^1$H NMR (300 MHz, DMSO) δ 1.56 (m, 1H), 1.86 (m, 2H), 1.99 (m, 1H), 2.92 (m, 1H), 3.05 (m, 1H), 3.80 (m, 2H), 4.09 (m, 3H), 5.16 (s, 2H), 6.34 (d, J=7.2 Hz, 1H), 7.34 (m, 6H); 8.91 (broad s, 1H); $^{19}$F NMR (252 MHz, DMSO) δ 88.5; $^{13}$C NMR (75 MHz, DMSO) δ; ES MS(M+1) 315.16; HRMS. Calcd. For $C_{18}H_{22}N_2O_3$, 314.38. Found (M+1) 315.16.

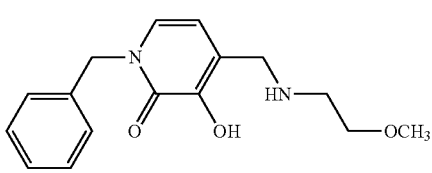

1-Benzyl-3-hydroxy-4-[(2-methoxyethylamino)methyl]pyridin-2(1H)-one: $^1$H NMR (300 MHz, DMSO) δ 3.13 (broad s, 2H), 3.30 (s, 3H), 3.59 (t, J=5.4 Hz, 2H), 4.02 (s, 2H), 5.16 (s, 2H), 6.34 (d, J=7.2 Hz, 1H), 7.34 (m, 6H), 8.91 (broad s, 1H); $^{19}$F NMR (252 MHz, DMSO) δ 88.4; $^{13}$C NMR (252 MHz, DMSO) δ; ES MS(M+1) 289.13; HRMS Calcd. For $C_{16}H_{20}N_2O_3$, 288.34. Found (M+1) 289.15.

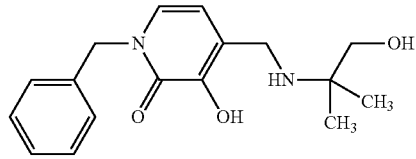 [SMILES: CC(C)(CO)NCc1ccn(Cc2ccccc2)c(=O)c1O]

1-Benzyl-3-hydroxy-4-[(1-hydroxy-2-methylpropan-2-ylamino)methyl]pyridin-2(1H)-one: $^1$H NMR (300 MHz, DMSO) δ 1.27 (s, 6H), 3.49 (s, 2H), 3.95 (s, 2H), 5.17 (s, 2H), 6.34 (d, J=7.2 Hz, 1H), 7.34 (m, 6H), 8.47 (broad s, 2H), 9.94 (broad s, 1H); $^{19}$F NMR (252 MHz, DMSO) δ 88.7; 13C NMR (75 MHz, DMSO) δ; ES MS(M+1) 303.19; HRMS Calcd. For $C_{17}H_{22}N_2O_3$, 302.37. Found (M+1) 303.17.

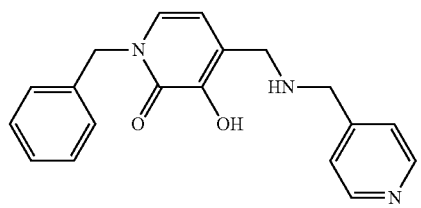 [SMILES: O=c1c(O)c(CNCc2ccncc2)ccn1Cc1ccccc1]

1-Benzyl-3-hydroxy-4-[(pyridin-4-ylmethylamino)methyl]pyridin-2(1H)-one: $^1$H NMR (300 MHz, DMSO) δ 4.07 (s, 2H), 4.32 (s, 2H), 5.16 (s, 2H), 6.34 (d, J=7.2 Hz, 1H), 7.34 (m, 6H); 7.62 (d, J=5.7 Hz, 2H), 8.71 (d, J=4.5 Hz, 2H); $^{19}$F NMR (252 MHz, DMSO) δ 88.0; $^{13}$C NMR (75 MHz, DMSO) δ; ES MS(M+1) 322.17; HRMS Calcd. For $C_{19}H_{19}N_3O_2$, 321.37. Found (M+1) 322.15.

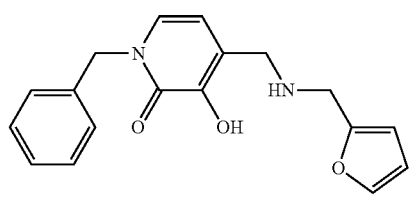 [SMILES: O=c1c(O)c(CNCc2ccco2)ccn1Cc1ccccc1]

1-Benzyl-3-hydroxy 4-{[(furan-2-ylmethyl)amino]methyl}pyridin-2(1H)-one: $^1$H NMR (300 MHz, DMSO) δ 4.00 (s, 2H), 4.28 (s, 2H), 5.16 (s, 2H), 6.27 (d, J=6.9 Hz, 1H), 6.54 (m, 1H), 6.65 (m, 1H), 7.34 (m, 6H), 7.80 (m, 1H), 9.27 (broad s, 1H); $^{19}$F NMR (252 MHz, DMSO) δ 88.3; $^{13}$C NMR (75 MHz, DMSO) δ; ES MS(M+1) 323.15; HRMS Calcd. For $C_{18}H_{18}N_2O_3$, 310.35. Found (M+1).

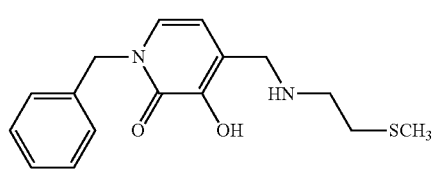

1-Benzyl-3-hydroxy-4-{[2-(methylthio)ethylamino]methyl}pyridin-2(1H)-one: $^1$H NMR (300 MHz, DMSO) δ

2.10 (s, 3H), 2.74 (t, J=6.9 Hz, 2H), 3.16 (t, J=8.1 Hz, 2H), 4.05 (s, 2H), 5.17 (s, 2H), 6.34 (d, J=7.2 Hz, 1H), 7.34 (m, 6H), $^{19}$F NMR (252 MHz, DMSO) δ 89.0; ES MS(M+1) 305.14, HRMS Calcd. For $C_{16}H_{20}N_2O_2S$, 304.41. Found (M+1).

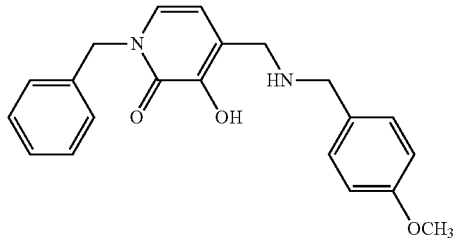 [SMILES: COc1ccc(CNCc2ccn(Cc3ccccc3)c(=O)c2O)cc1]

1-Benzyl-3-hydroxy-4-[(4-methoxybenzylamino)methyl]pyridin-2(1H)-one: $^1$H NMR (300 MHz, DMSO) δ 3.70 (s, 3H), 3.98 (s, 2H), 4.13 (s, 2H), 5.16 (s, 2H), 6.28 (d, J=7.5 Hz, 1H), 7.00 (d, J=9.0 Hz, 4H), 7.34 (m, 6H); 9.07 (broad s, 1H); $^{19}$F NMR (252 MHz, DMSO) δ 89.0; ES MS(M+1) 351.10; HRMS Calcd. For $C_{21}H_{22}N_2O_3$, 350.41. Found (M+1) 351.17.

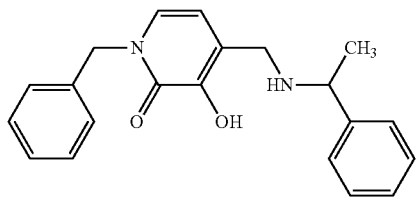 [SMILES: CC(NCc1ccn(Cc2ccccc2)c(=O)c1O)c1ccccc1]

1-Benzyl-3-hydroxy-4-[(1-phenylethylamino)methyl]pyridin-2(1H)-one: $^1$H NMR (300 MHz, DMSO) δ 1.59 (d, J=7.2 Hz, 3H), 3.71-3.93 (m, 2H), 4.45 (m, 1H), 5.15 (s, 2H), 6.28 (d, J=7.5 Hz, 1H), 7.34 (m, 11H); $^{19}$F NMR (252 MHz, DMSO) δ 88.9; $^{13}$C NMR (75 MHz, DMSO) δ 19.6, 42.5, 51.7, 58.0, 106.8, 119.3, 128.0, 128.1, 128.2, 128.9, 129.3, 129.4, 137.3, 145.9, 158.3; ES MS(M+1) 335.13; HRMS Calcd. For $C_{21}H_{22}N_2O_2$, 334.41. Found (M+1) 335.17.

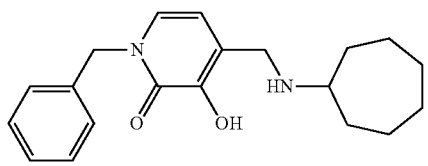

1-Benzyl-3-hydroxy-4-(cycloheptylaminomethyl)pyridin-2(1H)-one: $^1$H NMR (300 MHz, DMSO) δ 1.55 (m, 10H), 2.03 (m, 2H), 3.18 (s, 1H), 3.99 (m, 2H), 5.17 (s, 2H), 6.32 (d, J=6.9 Hz, 1H), 7.35 (m, 6H), 8.65 (broad s, 2H), 9.98 (broad s, 1H); $^{19}$F NMR (252 MHz, DMSO) δ 88.6; $^{13}$C NMR (75 MHz, DMSO) δ 23.0, 27.2, 30.4, 41.6, 51.7, 58.9, 107.0, 111.7, 127.9, 128.0, 128.2, 128.8, 137.4, 146.0, 157.5; ES MS(M+1) 327.13; HRMS Calcd. For $C_{20}H_{26}N_2O_2$, 326.43. Found (M+1) 327.20.

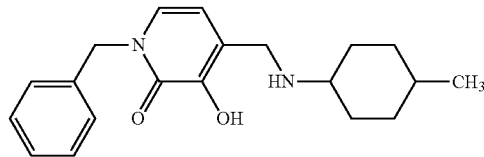 [SMILES: CC1CCC(NCc2ccn(Cc3ccccc3)c(=O)c2O)CC1]

1-Benzyl-3-hydroxy-4-[(4-methylcyclohexylamino)methyl]pyridin-2(1H)-one: $^1$H NMR (300 MHz, DMSO) δ 0.93 (d, J=6.9 Hz, 3H), 1.38 (m, 4H), 1.74 (m, 4H), 2.05 (m, 1H), 3.10 (m, 1H), 4.01 (s, 2H), 5.17 (s, 2H), 6.31 (m, 1H), 7.34 (m, 6H), 8.05 (broad s, 2H), 9.98 (broad s, 1H); $^{19}$F NMR (252 MHz, DMSO) δ 88.9; ES MS(M+1) 327.14; HRMS Calcd. For $C_{20}H_{26}N_2O_2$, 326.43; Found (M+1) 372.20.

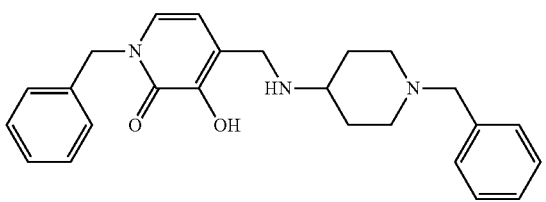 [SMILES: O=c1c(O)c(CNC2CCN(Cc3ccccc3)CC2)ccn1Cc1ccccc1]

1-Benzyl-3-hydroxy-4-[(1-benzylpiperidin-4-ylamino)methyl]pyridin-2(1H)-one: $^1$H NMR (300 MHz, DMSO) δ 1.77 (m, 2H), 2.31 (m, 2H), 2.98 (m, 2H), 3.30 (m, 3H), 3.46 (m, 2H), 4.03 (s, 2H), 0.29 (s, 2H), 5.16 (s, 2H), 6.30 (d, J=7.5 Hz, 1H), 7.34 (m, 6H), 7.49 (s, 5H), 9.12 (broad s, 1H), 10.05 (broad s, 1H); $^{19}$F NMR (252 MHz, DMSO) δ 88.8; $^{13}$C NMR (75 MHz, DMSO) δ 27.1, 43.4, 51.8, 52.1, 54.2, 54.7, 57.6, 106.9, 118.5, 128.0, 128.1, 128.8, 129.3, 129.8, 130.7, 131.3, 137.3, 146.2, 157.4; ES MS(M+1) 404.56; HRMS Calcd. For $C_{25}H_{28}N_3O_2$, 403.52. Found (M+1) 404.23.

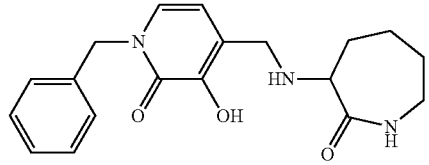 [SMILES: O=C1NCCCCC1NCc1ccn(Cc2ccccc2)c(=O)c1O]

3-[(1-Benzyl-3-hydroxy-2-oxo-1,2-dihydropyridin-4-yl)methylamino]azepan-2-one: $^1$H NMR (300 MHz, DMSO) δ 1.25 (m, 1H), 1.59 (m, 2H), 1.74 (m, 1H), 1.92 (m, 1H), 2.10 (m, 1H), 3.18 (m, 3H), 4.03 (s, 2H), 4.2 (m, 1H), 5.17 (s, 2H), 6.33 (d, J=7.5 Hz, 1H), 7.34 (m, 6H), 8.31 (t, J=5.4 Hz, 1H), 9.07 (broad s, 2H), 9.90 (broad s, 1H); $^{19}$F NMR (252 MHz, DMSO) δ 88.4; $^{13}$C NMR (75 MHz, DMSO) δ 27.0, 27.2, 28.4, 43.4, 51.7, 59.3, 107.1, 118.9, 127.8, 127.9, 128.1, 128.9, 137.4, 146.0, 157.5, 166.3; ES MS(M+1) 342.01; HRMS Calcd. For $C_{19}H_{23}N_3O_3$, 341.40. Found (M+1) 342.18.

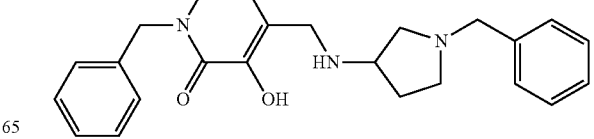

1-Benzyl-3-hydroxy-4-[(1-benzylpyrrolidin-3-ylamino)methyl]pyridin-2(1H)-one: $^1$H NMR (300 MHz, DMSO) δ 2.22 (m, 2H), 2.42 (m, 1H), 3.39 (m, 3H), 3.68 (m, 1H), 4.06 (s, 2H), 4.39 (s, 2H), 5.17 (s, 2H), 6.33 (d, J=7.5 Hz, 1H), 7.30-7.52 (m, 11H); $^{19}$F NMR (252 MHz, DMSO) δ 88.5; $^{13}$C NMR (75 MHz, DMSO) δ 27.1, 43.4, 51.8, 52.1, 54.2, 54.7, 57.5, 106.9, 118.5, 128.0, 128.8, 129.3, 129.8, 130.7, 131.3, 137.3, 146.2, 157.5; ES MS(M+1) 390.14; HRMS Calcd. For $C_{24}H_{27}N_3O_2$, 389.49. Found (M+1) 390.21.

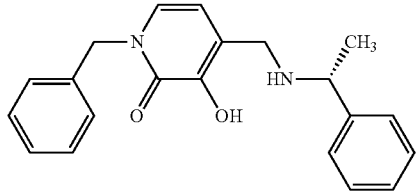 [SMILES: C[C@@H](NCc1ccn(Cc2ccccc2)c(=O)c1O)c1ccccc1]

(R)-1-Benzyl-3-hydroxy-4-[(1-phenylethylamino)methyl]pyridin-2(1H)-one: $^1$H NMR (300 MHz, DMSO) δ 1.58 (d, J=6.9 Hz, 3H), 3.74 (m, 2H), 4.44 (m, 1H), 5.14 (s, 2H), 6.23 (d, J=7.2 Hz, 1H), 7.35 (m, 6H); $^{19}$F NMR (252 MHz, DMSO) δ 89.4; $^{13}$C NMR (75 MHz, DMSO) δ 19.6, 42.6, 51.7, 58.0, 106.9, 18.7, 128.0, 128.1, 128.8, 129.3, 129.4, 137.2, 137.4, 145.9, 157.5; ES MS(M+1) 335.13; Anal. Calcd. For $C_{21}H_{22}N_2O_2$, 334.41. Found (M+1) 335.31.

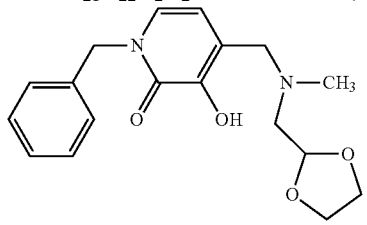

1-Benzyl-3-hydroxy-4-[([1,3]dioxolan-2-ylmethylmethylamino)methyl]pyridin-2(1H)-one: $^1$H NMR (300 MHz, DMSO) δ 2.81 (s, 3H), 3.35 (d, J=3.9 Hz, 2H), 3.89 (m, 2H), 4.01 (m, 2H), 4.21 (m, 2H), 5.17 (s, 2H); 5.27 (t, J=3.9 Hz, 1H), 6.34 (d, J=7.2 Hz, 1H), 7.35 (m, 6H); $^{19}$F NMR (252 MHz, DMSO) δ 88.5; $^{13}$C NMR (75 MHz, DMSO) δ; ES MS(M+1) 331.18; HRMS Calcd. For $C_{18}H_{22}N_2O_4$, 330.38. Found (M+1) 331.16.

Category IV of the disclosed prolyl hydroxylase inhibitors relates to compounds having the formula:

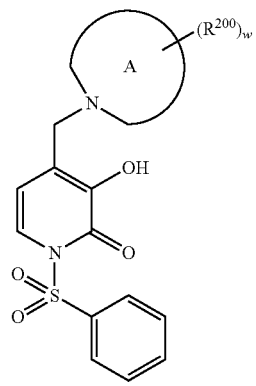

wherein A represents a ring optionally substituted by one or more $R^{200}$ units. Table IV provides non-limiting examples of this category.

TABLE IV

| No. | A ring |
|---|---|
| D1 | pyrrolidin-1-yl |
| D2 | 3-hydroxypyrrolidin-1-yl |
| D3 | 2-(pyrdin-2-yl)pyrrolidin-1-yl |
| D4 | 2-methylcarboxypyrrolidin-1-yl |
| D5 | 2-(methoxymethyl)pyrrolidin-1-yl |
| D6 | thiazolidin-3-yl |
| D7 | 1H-imidazol-1-yl |
| D8 | piperidin-1-yl |
| D9 | 4-benzylpiperidin-1-yl |
| D10 | 1,4'-bipiperidinyl-1'-yl |
| D11 | piperazin-1-yl |
| D12 | 4-benzylpiperazin-1-yl |
| D13 | 4-(2-methoxyphenyl)piperazin-1-ylmethyl |
| D14 | 4-(6-chloropyridazin-3-yl)piperazin-1-yl |
| D15 | 1,4-dioxa-8-azaspiro[4,5]dec-8-yl |
| D16 | morpholin-4-yl |
| D17 | thiomorpholin-4-yl |
| D18 | azepan-1-yl |
| D19 | azocan-1-yl |
| D20 | 3,4-dihydroquinolin-1(2H)-yl |

The disclosed compounds of this category can be prepared by the procedure outlined herein below in Scheme III and described in Example 3.

Scheme III

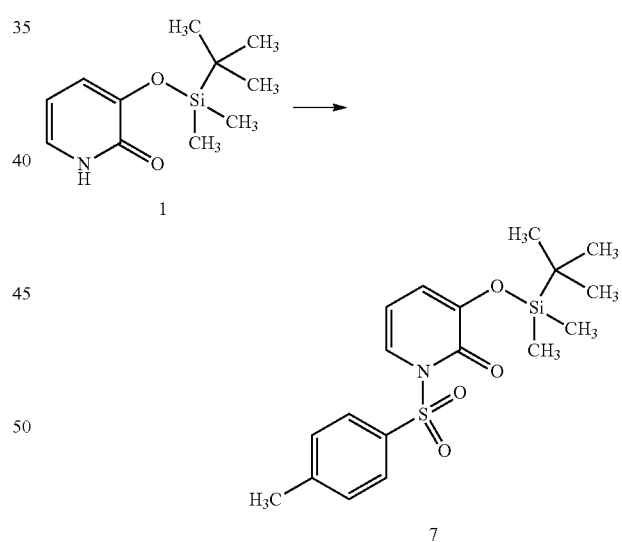

Reagents and conditions: (a) (i) n-BuLi, TsCl, THF; -78° C. to rt, 1 hr; (ii) HCl, MeOH; rt, 1 hr.

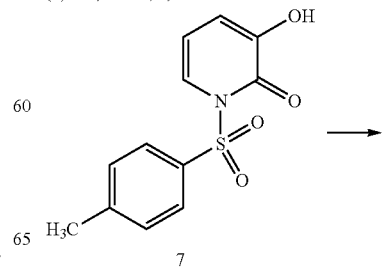

-continued

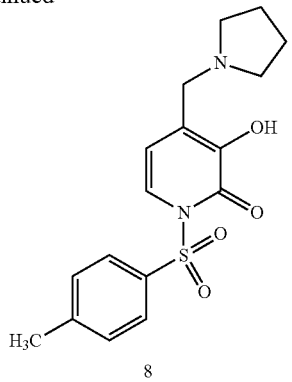

Reagents and conditions: (b) pyrrolidine, HCHO, H₂O/EtOH; rt, 12 hr.

EXAMPLE 3

1-(4'-Methylbenzenesulfonyl)-3-hydroxy-4-(pyrrolidin-1-ylmethyl)pyridin-2(1H)-one (8)

1-(4'-Methylbenzenesulfonyl)-3-hydroxypyridin-2(1H)-one (7): To stirred solution of 3-[(tert-butyldimethylsilyl)oxy]pyridin-2(1H)-one (1) (4.66 g, 20.7 mmol) in dry THF (150 mL), maintained at −78° C. under a dry nitrogen atmosphere is added n-butyl lithium (1.6 M solution in hexane, 21.0 mmol). After 20 minutes, 4-methyl-benzenesulfonyl chloride (3.95 g, 20.7 mmol) is added as a THF solution. The solution is allowed to warm to room temperature over one hour, the water (10 mL) is added and the contents of the reaction vessel is extracted with EtOAc (3×), washed with brine (1×), dried over Na₂SO₄ and concentrated. The combined organic layers are dried over Na₂SO₄ and concentrated. The residue is taken up in ethanol (10 mL) and treated with conc. HCl (2 mL). The mixture is allowed to stir for 1 hour and the solvent is removed under reduced pressure to afford the desired compound as a white solid. $^1$H NMR (300 MHz, DMSO) δ 2.43 (s, 3H), 6.14 (t, J=6.9 Hz, 1H), 6.76 (dd, J=7.65 Hz, 1.5 Hz, 1H), 7.18 (dd, J=6.6 Hz, 1.8 Hz, 1H), 7.32 (d, J=7.3 Hz, 2H), 7.98 (d, J=7.9 Hz, 2H).

1-(4'-Methylbenzenesulfonyl)-3-hydroxy-4-(pyrrolidin-1-ylmethyl)pyridin-2(1H)-one (8): 1-(4'-Methylbenzenesulfonyl)-3-hydroxypyridin-2(1H)-one (7) (250 mg, 0.94 mmol) and formaldehyde (200 mg, 2.07 mmol) are combined in aqueous ethanol (10 mL) and stirred for 30 minutes. Pyrrolidine (149 mg, 2.07 mmol) is then added and the reaction stirred for 12 hours. The solvent is removed by evaporation and the residue dissolved in methanol (5 mL) and purified via prep HPLC eluting with water/acetonitrile to afford the desired product. $^1$H NMR (300 MHz, DMSO) δ 1.87 (m, 2H), 1.99 (m, 2H), 2.44 (s, 3H), 3.09 (m, 2H), 3.40 (m, 2H), 4.19 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz, 1H), 9.93 (broad s, 1H); $^{19}$F NMR (252 MHz, DMSO) δ 88.4; 13C NMR (75 MHz, DMSO) δ 21.5, 22.7, 50.5, 53.7, 108.7, 118.6, 119.4, 128.4, 129.7, 130.1, 133.1, 146.8, 147.7, 156.2; ES MS(M+1) 349.25; HRMS Calcd. For $C_{12}H_{20}N_2O_4S$, 348.42. Found (M+1) 349.42.

The following are further non-limiting examples of prolyl hydroxylase inhibitors according to this category.

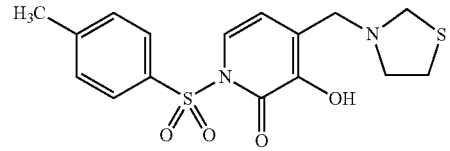 [SMILES: Cc1ccc(S(=O)(=O)n2ccc(CN3CCSC3)c(O)c2=O)cc1]

1-(4'-Methylbenzenesulfonyl)-3-hydroxy-4-thiazolidin-3-ylmethylpyridin-2(1H)-one: $^1$H NMR (300 MHz, DMSO) δ 2.43 (s, 3H), 2.94 (t, J=6.6 MHz, 2H), 3.18 (t, J=6.0 Hz, 2H), 3.66 (s, 2H), 4.12 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz, 1H), $^{19}$F NMR (252 MHz, DMSO) δ 87.9; $^{13}$C NMR (75 MHz, DMSO) δ 21.5, 21.9, 24.6, 25.8, 50.3, 51.6, 108.7, 118.6, 120.8, 129.7, 130.1, 133.1, 146.9, 148.1, 156.1, 158.4, 158.8; ES MS(M+1) 367.18; HRMS Calcd. For $C_{16}H_{18}N_2O_4S_2$, 366.46. Found (M+1) 367.43.

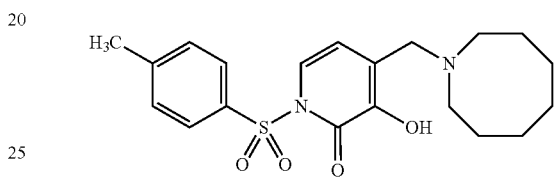

1-(4'-Methylbenzenesulfonyl)-3-hydroxy-4-azocan-1yl-methylpyridin-2(1H)-one: $^1$H NMR (300 MHz, DMSO) δ 1.59 (m, 10H), 2.44 (s, 3H), 3.17 (m, 2H), 3.32 (m, 2H), 4.15 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz); $^{19}$F NMR (252 MHz, DMSO) δ 88.7; $^{13}$C NMR (75 MHz, DMSO) δ 21.5, 21.9, 23.7, 24.6, 25.8, 50.3, 51.6, 108.7, 118.9, 120.8, 129.8, 130.1, 133.1, 146.9, 148.2, 156.1; ES MS(M+1) 391.18; HRMS Calcd. For $C_{20}H_{26}N_2O_4S$, 390.18. Found (M+1) 391.23.

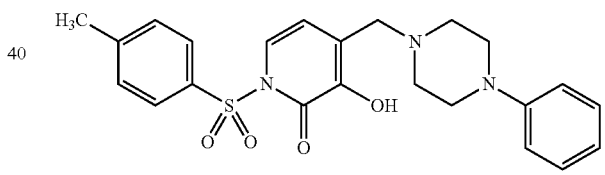

1-(4'-Methylbenzenesulfonyl)-3-hydroxy-4-(4-phenylpiperazin-1-ylmethyl)-pyridin-2(1H)-one: $^1$H NMR (300 MHz, DMSO) δ 2.43 (s, 3H), 3.13 (m, 8H), 3.43 (s, 2H), 6.47 (d, J=7.5 Hz, 1H), 6.78 (t, J=7.2 Hz, 1H), 7.21 9 m, 2H), 7.50 (d, J=8.1 Hz, 2H), 7.67 (d, J=7.8 Hz, 1H), 7.97 (d, J=8.4 Hz, 2H); $^{13}$C NMR (75 MHz, DMSO) δ 21.5, 42.6, 45.6, 46.2, 50.8, 51.9, 109.6, 116.4, 116.8, 117.7, 120.6, 121.1, 129.5, 129.6, 129.8, 130.1, 133.2, 146.8, 149.5, 156.1; ES MS(M+1) 440.15; HRMS Calcd. For $C_{23}H_{25}N_3O_5S$, 439.53. Found (M+1) 440.16.

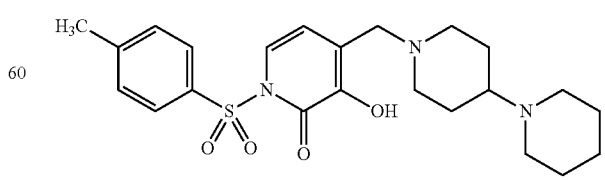

1-(4'-Methylbenzenesulfonyl)-3-hydroxy-4-[1,4']Bipiperidinyl-1'-ylmethylpyridin-2(1H)-one: $^1$H NMR (300 MHz, DMSO) δ 1.43 (m, 1h), 1.67 (m, 2H), 1.82 (m, 4H), 2.19 (m, 2H), 2.44 (s, 3H), 2.94 (m, 4H), 3.39 (m, 2H), 3.54 (m, 3H), 4.06 (s, 2H), 6.47 (d, J=8.1 Hz, 1H), 7.51 (d, J=8.1 Hz, 2H), 7.73 (d, 7.8 Hz, 1H), 7.99 (d, J=8.4 Hz, 2H); $^{19}$F NMR (252 MHz, DMSO) δ 88.7; $^{13}$C NMR (75 MHz, DMSO) δ 21.4, 22.9, 23.6, 48.4, 49.5, 59.4, 109.3, 114.8, 117.6, 120.5, 122.7, 129.7, 130.1, 133.1, 146.9, 148.6, 156.2; ES MS(M+1) 446.19; HRMS Calcd. For $C_{23}H_{31}N_3O_4S$, 445.58. Found (M+1) 446.21.

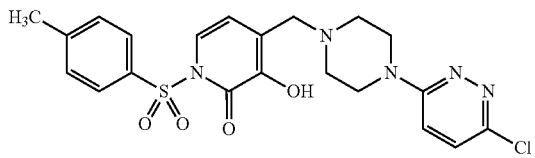 [SMILES: Cc1ccc(S(=O)(=O)n2ccc(CN3CCN(c4ccc(Cl)nn4)CC3)c(O)c2=O)cc1]

1-(4'-Methylbenzenesulfonyl)-3-hydroxy-4-[4-(6-chloro-pyridazin-3-yl)piperazin-1-ylmethyl]pyridin-2(1H)-one: $^1$H NMR (300 MHz, DMSO) δ 2.44 (s, 3H), 3.17 (m, 2H), 3.46 (m, 4H), 4.17 (s, 2H), 4.45 (m, 2H), 6.77 (d, J=7.8 Hz, 1H), 7.04 (m, 1H), 7.53 (m 2H), 7.68 (m, 2H), 7.98 (m, 2H), 11.3 (broad s, 1H), ES MS(M+1) 476.92. HRMS Calcd. For $C_{21}H_{25}ClN_5O_4S$, 475.95. Found (M+1) 476.11.

Category V of HIF-1α prolyl hydroxylase inhibitors relates to compounds having the formula:

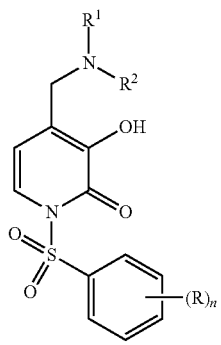

R represents from 1 to 5 optional substitutions for a phenyl ring hydrogen atom, $R^1$ and $R^2$ are each independently hydrogen or substituted or unsubstituted $C_1$-$C_{10}$ linear or branched alkyl, wherein the alkyl unit can be substituted by one or more units independently chosen from:

i) $C_1$-$C_8$ linear, $C_3$-$C_8$ branched, or $C_3$-$C_8$ cyclic alkoxy;

ii) hydroxy;

iii) halogen;

iv) cyano;

v) amino, $C_1$-$C_8$ mono-alkylamino, $C_1$-$C_8$ di-alkylamino;

vi) —$SR^{40}$; $R^{40}$ is hydrogen or $C_1$-$C_4$ linear or $C_3$-$C_4$ branched alkyl;

vii) substituted or unsubstituted $C_6$ of $C_{10}$ aryl;

viii) substituted or unsubstituted $C_1$-$C_9$ heterocyclic; or ix) substituted or unsubstituted $C_1$-$C_9$ heteroaryl.

Table V provides non-limiting examples of this category of HIF-1α prolyl hydroxylase inhibitors.

TABLE V

| No. | R | $R^1$ | $R^2$ |
|---|---|---|---|
| E1 | 4-methyl | benzyl | hydrogen |
| E2 | 4-methyl | 4-methoxybenzyl | hydrogen |
| E3 | 4-methyl | 4-fluorobenzyl | hydrogen |
| E4 | 4-methyl | 4-chlorobenzyl | hydrogen |
| E5 | 4-methyl | 4-methylbenzyl | hydrogen |
| E6 | 4-methyl | 2-(pyridin-2-yl)ethyl | hydrogen |
| E7 | 4-methyl | [1,3]dioxolan-2-ylmethyl | hydrogen |
| E8 | 4-methyl | tetrahydrofuran-2-ylmethyl | hydrogen |
| E9 | 4-methyl | 2-methoxyethyl | hydrogen |
| E10 | 4-methyl | 1-hydroxy-2-methylpropan-2-yl | hydrogen |
| E11 | 4-methyl | pyridin-4-ylmethyl | hydrogen |
| E12 | 4-methyl | furan-2-ylmethyl | hydrogen |
| E13 | 4-methyl | 2-(methylthio)ethyl | hydrogen |
| E14 | 4-methyl | 1-phenylethyl | hydrogen |
| E15 | 4-methyl | 3-imidazol-1-ylpropyl | hydrogen |
| E16 | 4-methyl | cycloheptyl | hydrogen |
| E17 | 4-methyl | 4-methylcyclohexyl | hydrogen |
| E18 | 4-methyl | 1-benzylpiperidin-4-yl | hydrogen |
| E19 | 4-methyl | azepan-2-on-3-yl | hydrogen |
| E20 | 4-methyl | 1-benzylpyrrolidin-3-yl | hydrogen |
| E21 | 4-methyl | benzyl | methyl |
| E22 | 4-methyl | 4-methoxybenzyl | methyl |
| E23 | 4-methyl | 4-fluorobenzyl | methyl |
| E24 | 4-methyl | 4-chlorobenzyl | methyl |
| E25 | 4-methyl | 4-methylbenzyl | methyl |
| E26 | 4-methyl | 2-(pyridin-2-yl)ethyl | methyl |
| E27 | 4-methyl | [1,3]dioxolan-2-ylmethyl | methyl |
| E28 | 4-methyl | tetrahydrofuran-2-ylmethyl | methyl |
| E29 | 4-methyl | 2-methoxyethyl | methyl |
| E30 | 4-methyl | 1-hydroxy-2-methylpropan-2-yl | methyl |
| E31 | 4-methyl | pyridin-4-ylmethyl | methyl |
| E32 | 4-methyl | furan-2-ylmethyl | methyl |
| E33 | 4-methyl | carboxymethyl | methyl |
| E34 | 4-methyl | 2-(methylthio)ethyl | methyl |
| E35 | 4-methyl | 1-phenylethyl | methyl |
| E36 | 4-methyl | 3-imidazol-1-ylpropyl | methyl |
| E37 | 4-methyl | cycloheptyl | methyl |
| E38 | 4-methyl | 4-methylcyclohexyl | methyl |
| E39 | 4-methyl | 1-benzylpiperidin-4-yl | methyl |
| E40 | 4-methyl | azepan-2-on-3-yl | methyl |
| E41 | 4-methyl | 1-benzylpyrrolidin-3-yl | methyl |

The disclosed compounds of this category can be prepared by the procedure outlined herein below in Scheme IV and described in Examples 4.

Scheme IV

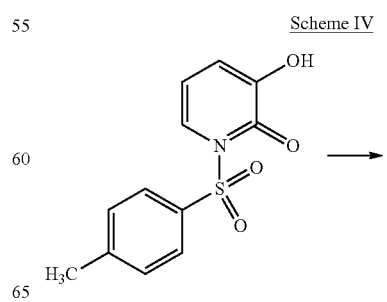

7

-continued

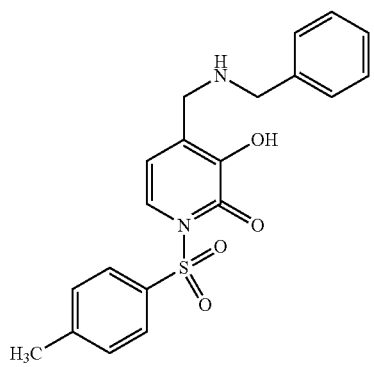

9

Reagants and conditions: (a) benzyl bromide, HCHO, H₂O/EtOH; rt, 12 hr.

EXAMPLE 4

1-(4'-Methylbenzenesulfonyl)-3-hydroxy-4-[(benzy-lamino)methyl]-pyridin-2(1H)-one (9)

1-(4'-Methylbenzenesulfonyl)-3-hydroxy-4-(benzylaminomethyl)pyridin-2(1H)-one (9): 1-(4'-Methylbenzenesulfonyl)-3-hydroxypyridin-2(1H)-one (7) (250 mg, 0.94 mmol) and formaldehyde (200 mg, 2.07 mmol) are combined in aqueous ethanol (10 mL) and stirred for 30 minutes. Benzylamine (229 mg, 2.07 mmol) is then added and the reaction stirred for 12 hours. The solvent is removed by evaporation and the residue dissolved in methanol (5 mL) and purified via prep HPLC eluting with water/acetonitrile to afford the desired product as the trifluoracetate salt. $^1$H NMR (300 MHz, DMSO) δ 2.44 (s, 3H), 3.96 (s, 2H), 4.16 (s, 2H), 6.69 (d, J=8.1 Hz), 7.40 (m, 7H), 7.52 (m, 1H), 7.73 (d, J=8.1 Hz, 1H), 7.97 (d, J=8.1 Hz, 1H), 9.71 (broad s, 2H), 10.44 (broad s, 1H); ES MS(M+1) 396.67; HRMS Calcd. For $C_{20}H_{20}N_2O_4S$, 384.45. Found (M+1) 385.12.

The following is a further non-limiting example of this category of HIF-1α prolyl hydroxylase inhibitors.

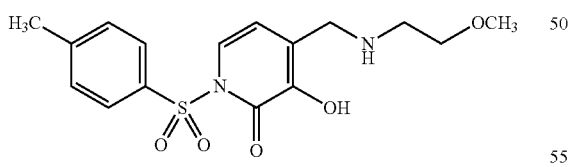

1-(4'-Methylbenzenesulfonyl)-3-hydroxy-4-[(2-methoxy-ethylamino)methyl]-pyridin-2(1H)-one: $^1$H NMR (300 MHz, DMSO) δ 2.43 (s, 3H), 3.12 (m, 2H), 3.29 (s, 3H), 3.56 (t, J=5.1 Hz, 2H), 3.99 (s, 2H), 6.51 (d, J=7.5 Hz, 1H), 7.51 (d, J=8.4 Hz, 1H), 7.76 (d, J=7.5 Hz, 1H), 7.98 (d, J=8.1 Hz); $^{19}$F NMR (252 MHz, DMSO) δ 88.6; $^{13}$C NMR (75 MHz, DMSO) δ 21.5, 43.8, 46.2, 46.5, 58.5, 67.2, 106.7, 119.2, 120.2, 123.9, 128.4, 129.7, 130.1, 133.1, 146.8, 147.0, 156.0; ES MS(M+1) 353.12. HRMS Calcd. For $C_{16}H_{20}N_2O_5S$, 352.41. Found (M+1) 353.11.

Category VI of HIF-1α prolyl hydroxylase inhibitors relates to compounds having the formula:

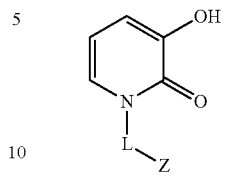

wherein L is chosen from $CH_2$ or $SO_2$, and Z is substituted or unsubstituted phenyl. Non-limiting examples of inhibitors according to this category are disclosed in Table VI below.

TABLE VI

| No. | L | Z |
|---|---|---|
| F1 | CH₂ | 2-chlorophenyl |
| F2 | CH₂ | 3-chlorophenyl |
| F3 | CH₂ | 4-chlorophenyl |
| F4 | CH₂ | 2-fluorophenyl |
| F5 | CH₂ | 3-fluorophenyl |
| F6 | CH₂ | 4-fluorophenyl |
| F7 | CH₂ | 2,3-dichlorophenyl |
| F8 | CH₂ | 2,4-dichlorophenyl |
| F9 | CH₂ | 2,5-dichlorophenyl |
| F10 | CH₂ | 2,6-dichlorophenyl |
| F11 | CH₂ | 3,4-dichlorophenyl |
| F12 | CH₂ | 3,5-dichlorophenyl |
| F13 | CH₂ | 2,3-difluorophenyl |
| F14 | CH₂ | 2,4-difluorophenyl |
| F15 | CH₂ | 2,5-difluorophenyl |
| F16 | CH₂ | 2,6-difluorophenyl |
| F17 | CH₂ | 3,4-difluorophenyl |
| F18 | CH₂ | 3,5-difluorophenyl |
| F19 | CH₂ | 2-cyanophenyl |
| F20 | CH₂ | 3-cyanophenyl |
| F21 | CH₂ | 4-cyanophenyl |
| F22 | SO₂ | 2-chlorophenyl |
| F23 | SO₂ | 3-chlorophenyl |
| F24 | SO₂ | 4-chlorophenyl |
| F25 | SO₂ | 2-fluorophenyl |
| F26 | SO₂ | 3-fluorophenyl |
| F27 | SO₂ | 4-fluorophenyl |
| F28 | SO₂ | 2,3-dichlorophenyl |
| F29 | SO₂ | 2,4-dichlorophenyl |
| F30 | SO₂ | 2,5-dichlorophenyl |
| F31 | SO₂ | 2,6-dichlorophenyl |
| F32 | SO₂ | 3,4-dichlorophenyl |
| F33 | SO₂ | 3,5-dichlorophenyl |
| F34 | SO₂ | 2,3-difluorophenyl |
| F35 | SO₂ | 2,4-difluorophenyl |
| F36 | SO₂ | 2,5-difluorophenyl |
| F37 | SO₂ | 2,6-difluorophenyl |
| F38 | SO₂ | 3,4-difluorophenyl |
| F39 | SO₂ | 3,5-difluorophenyl |
| F40 | SO₂ | 2-cyanophenyl |
| F41 | SO₂ | 3-cyanophenyl |
| F42 | SO₂ | 4-cyanophenyl |

The compounds encompassed within this category can be prepared according to Scheme I for Z equal to $CH_2$ and according to Scheme III for Z equal to $SO_2$.

Pharmaceutically Acceptable Salts

The disclosed HIF-1α prolyl hydroxylase inhibitors can be in the form of a pharmaceutically acceptable salt. Pharmaceutically acceptable salts can be used by the formulator to provide a form of the disclosed inhibitor that is more compatible with the intended delivery of the inhibitor to a subject or for compatibility of formulation.

The following are examples of procedures for preparing the pharmaceutically acceptable salt of the disclosed inhibitor, tert-butyl-{[1-(4-chlorobenzyl)-3-hydroxy-2-oxo-1,2-dihydropyridin-4-yl]methyl}piperazine-1-carboxylate.

A suspension of tert-butyl-{[1-(4-chlorobenzyl)-3-hydroxy-2-oxo-1,2-dihydropyridin-4-yl]methyl}piperazine-1-carboxylate (242 mg, 0.56 mmol) in MeOH (15 mL) was heated at reflux until a homogeneous solution was obtained. Heating was stopped and 0.1N HCl (6.7 mL, 1.2 eq.) was added while still hot and the solution was cooled to room temperature. The volatiles were evaporated under reduced pressure and the amorphous residue was crystallized in acetone (5 mL). The solid was collected by filtration.

A suspension of tert-butyl-{[1-(4-chlorobenzyl)-3-hydroxy-2-oxo-1,2-dihydropyridin-4-yl]methyl}piperazine-1-carboxylate (217 mg, 0.5 mmol) in MeOH (15 mL) was heated at reflux until a homogeneous solution was obtained. Heating was stopped and methanesulfonic acid (115.2 mg, 1.2 eq.) was added while still hot and the solution was cooled to room temperature. The volatiles were evaporated under reduced pressure and the amorphous residue was crystallized in acetone (5 mL). The solid was collected by filtration.

Table VII herein below provides examples of pharmaceutically acceptable salts of tert-butyl-{[1-(4-chlorobenzyl)-3-hydroxy-2-oxo-1,2-dihydropyridin-4-yl]methyl}-piperazine-1-carboxylate formed from organic and inorganic acids. Start

TABLE VII

| Acid | Yield | Purity* | M.P. (° C.) | color |
|---|---|---|---|---|
| Free base | — | 99.3% | 183-184 | pink |
| HCl | 90% | 99.7% | 185-186 | white |
| H₂SO₄ | 93% | 99.7% | 175 (dec.) | slightly pink |
| p-toluenesulfonyl | 74% | 99.8% | 185-186 | white |
| methanesulfonyl | 79% | 99.9% | 155-157 | white |

*HPLC analysis

¹H NMR analysis was used to determine the form of the salt, for example, that the mesylate salt formed herein above had the following formula:

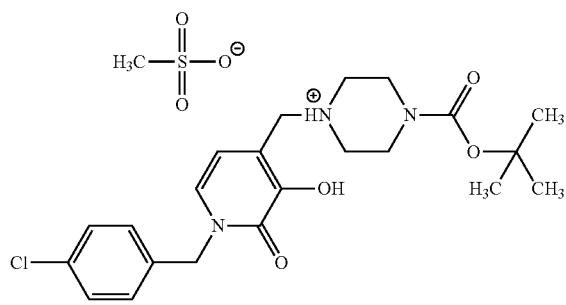

¹H NMR analysis was used to determine at which site of the molecule salt formation was taking place. The chemical shifts for the protons on the methylene group bridging the piperazine and the pyridinone rings shifted from 3.59 ppm in the free base to 4.31 ppm of the salt. In addition, the piperazine methylene groups adjacent to the tertiary amine shifted from 2.50 ppm to approximately 3.60 ppm. The chemical shifts for the remaining protons were largely unchanged. These data indicate that the tertiary amine nitrogen of the piperazine ring is protonated in salt forms. In addition, integration of the methyl protons of the methane sulfonyl unit relative to the core compound indicates the presence of one equivalent of the acid.

The formulator can determine the solubility of the pharmaceutically acceptable salts of the disclosed inhibitors by any method desirable. The following is a non-limiting example of a procedure for evaluating the solubility of a salt of a disclosed inhibitor. A suspension of tert-butyl-{[1-(4-chlorobenzyl)-3-hydroxy-2-oxo-1,2-dihydropyridin-4-yl]methyl}-piperazine-1-carboxylate methanesulfonate (26.6 mg) in distilled deionized water (3.0 mL) is sonicated for 20 min with water bath temperature under 25° C. The suspension is filtered to remove any insoluble salt. The clear filtrate solution (200 μL) is diluted with distilled deionized water (800 μL) and subjected to HPLC analysis. The following are results for the pharmaceutically acceptable salts outlined in Table VII above.

| Salt | Solubility (mg/mL) | Purity* |
|---|---|---|
| Free base | ~0.001 | 99.3% |
| hydrochloride | 5.9 | 99.7% |
| hydrogensulfonate | 13.2 | 99.7% |
| p-toluenesulfonate | 2.3 | 99.8% |
| methanesulfonate | 16.6 | 99% |

*HPLC analysis

The following are non-limiting examples of other acids that can be used to form pharmaceutically acceptable salts of the disclosed inhibitors: acetate, ctrate, maleate, succinate, lactate, glycolate and tartrate.

Further disclosed herein is a process for preparing the disclosed HIF-1α prolyl hydroxylase inhibitors, comprising:

a) protecting the hydroxyl moiety of hydroxypyridin-2 (1H)-one to prepare a protected pyridone having the formula:

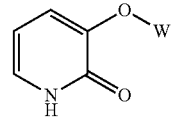

wherein W represents a protecting group;

b) reacting the protected pyridone with a compound having the formula:

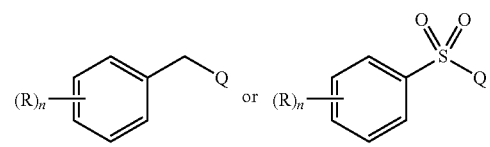

wherein R represents from 1 to 5 substitutions for hydrogen as defined herein, the index n is an integer from 0 to 5, Q is a leaving group, to form a O-protected N-benzyl pyridone or N-sulfonylphenyl pyridone having the formula:

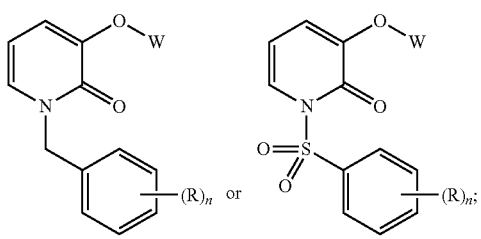

c) removing the protecting group from the O-protected N-benzyl pyridone or N-sulfonylphenyl pyridone to form an N-benzyl pyridone or N-sulfonylphenyl pyridone having the formula:

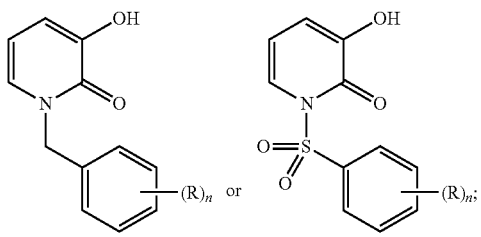

d) reacting an amine having the formula:

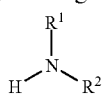

wherein $R^1$ and $R^2$ are the same as defined herein, with formaldehyde to form an N-formylamine having the formula:

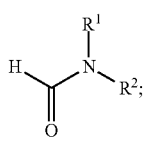

and e) reacting the N-formylamine formed in step (d) with the N-benzyl pyridone or N-sulfonylphenyl pyridone formed in step (c) to form a compound having the formula:

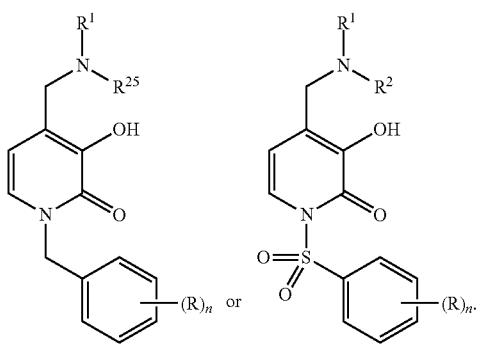

Step (a) Preparation of an O-protected hydroxypyridin-2(1H)-one

Step (a) relates to the formation of an O-protected hydroxypyridin-2(1H)-one having the formula:

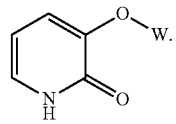

W can be any protecting group. Non-limiting examples of protecting groups include carbamates, for example, tert-butoxycarbonyl and methoxycarbonyl, alkylsilanes, for example, trimethylsilyl and tert-butyldimethylsilyl, and the like.

Step (b) Preparation of O-protected N-benzyl hydroxypyridin-2(1H)-one or O-protected N-sulfonylphenyl hydroxypyridin-2(1H)-one Step (b) relates to the formation of an O-protected N-benzyl hydroxypyridin-2(1H)-one or O-protected N-sulfonylphenyl hydroxypyridin-2(1H)-one having the formula

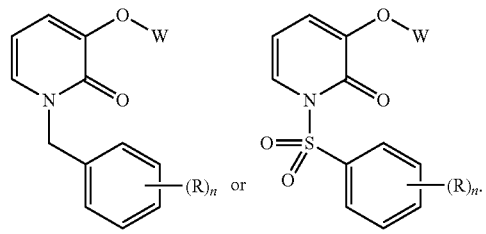

The protected hydroxypyridin-2(1H)-one formed in step (a) is reacted with a compound having the formula:

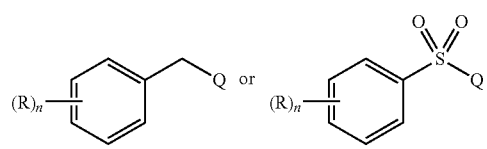

wherein Q is a leaving group capable of being eliminated by the protected hydroxypyridin-2(1H)-one ring nitrogen.

Step (c) Preparation of N-benzyl-3-hydroxypyridin-2 (1H)-one or N-sulfonylphenyl-3-hydroxypyridin-2 (1H)-one Step (c) relates to the formation of an N-benzyl-3-hydroxypyridin-2(1H)-one or N-sulfonylphenyl-3-hydroxypyridin-2 (1H)-one the having the formula:

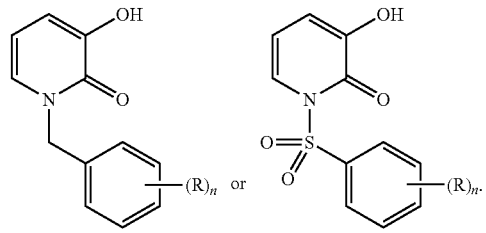

Wherein the O-protected N-benzyl hydroxypyridin-2(1H)-one or O-protected N-sulfonylphenyl hydroxypyridin-2(1H)-one formed in step (b) is reacted with one or more reagents suitable for removing protecting group W in a manner compatible with any R substitutions for hydrogen on the phenyl ring.

Step (d) Preparation of an N-Formylamine Synthon

Step (d) relates to the formation of an N-formylamine synthon having the formula:

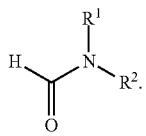

The N-formylamine is formed by reacting an amine having the formula:

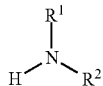

with formaldehyde or a reagent capable of generating formaldehyde in situ.

Step (e) Preparation of the Disclosed HIF-1α Prolyl Hydroxylase Inhibitors

Step (e) relates to the formation of the final disclosed compounds having the formula:

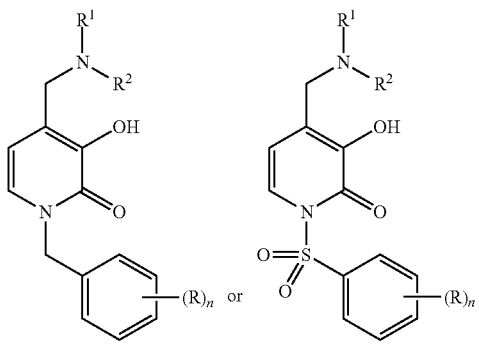

by reacting the N-formylamine formed in step (d) with the N-benzyl-3-hydroxypyridin-2(1H)-one or N-sulfonylphenyl-3-hydroxypyridin-2(1H)-one formed in step (c).

Formulations

Medicaments and Pharmaceutical Compositions

The present disclosure further relates to compositions or formulations that are useful for making a medicament or a pharmaceutical composition. The disclosed medicaments or pharmaceutical compositions comprising the disclosed human protein HIF-1α prolyl hydroxylase inhibitors can comprise:
  a) an effective amount of one or more HIF-1α prolyl hydroxylase inhibitors according to the present disclosure; and
  b) one or more excipients.

Diseases or conditions affected by increased stabilization of HIF-1 by inhibition of HIF-1α prolyl hydroxylase include PVD, CAD, heart failure, ischemia, anemia, wound healing, antimicrobial activity, increased phagocytosis, anti-cancer activity, and increase in the effectiveness of vaccines.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:
  a) from about 0.001 mg to about 1000 mg of one or more human protein HIF-1α prolyl hydroxylase inhibitors according to the present disclosure; and
  b) one or more excipients.

Another example according to the present disclosure relates to the following compositions:
  a) from about 0.01 mg to about 100 mg of one or more human protein prolyl HIF-1α prolyl hydroxylase inhibitors according to the present disclosure; and
  b) one or more excipients.

A further example according to the present disclosure relates to the following compositions:
  a) from about 0.1 mg to about 10 mg of one or more human protein HIF-1α prolyl hydroxylase inhibitors according to the present disclosure; and
  b) one or more excipients.

A still further example of compositions according to the present disclosure comprise:
  a) an effective amount of one or more human protein HIF-1α prolyl hydroxylase inhibitors according to the present disclosure; and
  b) one or more chemotherapeutic agents or chemotherapeutic compounds as further described herein.

A yet still further example of compositions according to the present disclosure comprise:
  a) an effective amount of one or more human protein HIF-1α prolyl hydroxylase inhibitors according to the present disclosure; and
  b) one or more vaccines for treatment of an infectious disease.

The present disclosure further relates to the use of one or more of the HIF-1α prolyl hydroxylase inhibitors disclosed herein for making a medicament for treating anemia.

The present disclosure further relates to the use of one or more of the HIF-1α prolyl hydroxylase inhibitors disclosed herein for making a medicament for treating increasing cellular immunity.

The present disclosure further relates to the use of one or more of the HIF-1α prolyl hydroxylase inhibitors disclosed herein for making a medicament for treating cancer.

The present disclosure further relates to the use of one or more of the HIF-1α prolyl hydroxylase inhibitors disclosed herein for making a medicament for increasing HIF-1 stabilization.

The present disclosure further relates to the use of one or more of the HIF-1α prolyl hydroxylase inhibitors disclosed herein for making a medicament for treating anemia.

The present disclosure further relates to the use of one or more of the HIF-1α prolyl hydroxylase inhibitors disclosed herein for making a medicament for treating peripheral vascular disease.

The present disclosure further relates to the use of one or more of the HIF-1α prolyl hydroxylase inhibitors disclosed herein for making a medicament for treating wounds.

The present disclosure further relates to the use of one or more of the HIF-1α prolyl hydroxylase inhibitors disclosed herein for making a medicament that is an antimicrobial.

The present disclosure further relates to the use of one or more of the HIF-1α prolyl hydroxylase inhibitors disclosed herein for making a medicament for treating atherosclerotic lesions.

The present disclosure further relates to the use of one or more of the HIF-1α prolyl hydroxylase inhibitors disclosed herein for making a medicament for treating diabetes.

The present disclosure further relates to the use of one or more of the HIF-1α prolyl hydroxylase inhibitors disclosed herein for making a medicament for treating hypertension.

The present disclosure further relates to the use of one or more of the HIF-1α prolyl hydroxylase inhibitors disclosed herein for making a medicament for treating a disease affected by the level of vascular endothelial growth factor (VEGF), glyceraldehyde 3-phosphate dehydrogenase (GAPDH), and erythropoietin (EPO).

The present disclosure further relates to the use of one or more of the HIF-1α prolyl hydroxylase inhibitors disclosed herein for making a medicament for treating a disorder chosen from Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

The present disclosure further relates to the use of one or more of the HIF-1α prolyl hydroxylase inhibitors disclosed herein for making a medicament for treating a disorder chosen from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy.

The disclosed compositions and the form of pharmaceutical preparations comprising the HIF-1α prolyl hydroxylase inhibitors alone, or in combination with another drug or other therapeutic agent, inter alia, chemotherapeutic agent or chemotherapeutic compound, can vary according to the intended route of administration.

Orally administered preparations can be in the form of solids, liquids, emulsions, suspensions, or gels, or in dosage unit form, for example as tablets or capsules. Tablets can be compounded in combination with other ingredients customarily used, such as talc, vegetable oils, polyols, gums, gelatin, starch, and other carriers. The HIF-1α prolyl hydroxylase inhibitors can be dispersed in or combined with a suitable liquid carrier in solutions, suspensions, or emulsions.

Parenteral compositions intended for injection, either subcutaneously, intramuscularly, or intravenously, can be prepared as liquids or solid forms for solution in liquid prior to injection, or as emulsions. Such preparations are sterile, and liquids to be injected intravenously should be isotonic. Suitable excipients are, for example, water, dextrose, saline, and glycerol.

Administration of pharmaceutically acceptable salts of the substances described herein is included within the scope of the present disclosure. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., *Journal of Pharmaceutical Sciences* 66:1-19 (1977) the disclosure of which is hereby incorporated by reference.

Substances for injection can be prepared in unit dosage form in ampules, or in multidose containers. The HIF-1α prolyl hydroxylase inhibitors or compositions comprising one or more HIF-1α prolyl hydroxylase inhibitors to be delivered can be present in such forms as suspensions, solutions, or emulsions in oily or preferably aqueous vehicles. Alternatively, the salt of the HIF-1α prolyl hydroxylase inhibitor can be in lyophilized form for reconstitution, at the time of delivery, with a suitable vehicle, such as sterile pyrogen-free water. Both liquids as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms can further comprise suitable formulatory agents, such as starch or sugar, glycerol or saline. The compositions per unit dosage, whether liquid or solid, can contain from 0.1% to 99% of polynucleotide material.

Methods

Methods Relating to Stabilization of HIF-1

The eradication of invading microorganisms depends initially on innate immune mechanisms that preexist in all individuals and act within minutes of infection. Phagocytic cell types, including macrophages and neutrophils, play a key role in innate immunity because they can recognize, ingest, and destroy many pathogens without the aid of an adaptive immune response. The effectiveness of myeloid cells in innate defense reflects their capacity to function in low oxygen environments. Whereas in healthy tissues oxygen tension is generally 20-70 mm HG (i.e. 2.5-9% oxygen), much lower levels (<1% oxygen) have been described in wounds and necrotic tissue foci (Arnold et al., *Br J Exp Pathol* 68, 569 (1987); Vogelberg & Konig, Clin Investig 71, 466 (1993); Negus et al., *Am J Pathol* 150, 1723 (1997)). It has also been shown (Zinkernagel A. S. et al., "Pharmacologic Augmentation of Hypoxia-Inducible Factor-1α with Mimosine Boosts the Bactericidal Capacity of Phagocytes" J. Infectious Diseases (2008):197: 214-217) that the HIF-1α agonist mimosine can boost the capacity of human phagocytes and whole blood to kill the leading pathogen *Staphylococcus aureus* in a dose-dependent fashion and reduce the lesion size in a murine model of *S. aureus* skin infection.

Macrophages are one population of effector cells involved in immune responses. Their role in natural immunity includes mediation of phagocytosis, as well as release of cytokines and cytotoxic mediators. They also facilitate the development of acquired immunity through antigen presentation and release of immunomodulatory cytokines. Although macrophages are immune effectors, they are also susceptible to infection by agents such as bacteria, protozoa, parasites, and viruses (The Macrophage, C. E. Lewis & J. O'D. McGee. eds., IRL Press at Oxford University Press, New York, N.Y., 1992). Viruses capable of infecting macrophages include several RNA viruses such as measles virus (MV) (e.g., Joseph et al., *J. Virol.* 16, 1638-1649, 1975), respiratory syncytial virus (RSV) (Midulla et al., *Am. Rev. Respir. Dis.* 140, 771-777, 1989), and human immunodeficiency virus type 1 (HIV-1) (Meltzer and Gendelman, in Macrophage Biology and Activation, S. W. Russell and S. Gordon, eds., Springer-Verlag, New York, N.Y., pp. 239-263(1992: Potts et al., *Virology* 175, 465-476, 1990).

Disclosed herein is a method for increasing HIF-1 stabilization in a cell, comprising contacting a cell in vivo, in vitro, or ex vivo with an effective amount of one or more of the disclosed HIF-1α prolyl hydroxylase inhibitors.

Also disclosed herein are methods for increasing the cellular immune response of a subject in need of increased cellular immunity, comprising administering to a subject in need with an effective amount of one or more of the disclosed HIF-1α prolyl hydroxylase inhibitors.

Further disclosed herein are methods for increasing the cellular immune response of a subject diagnosed with a medical condition causing a decreased cellular immunity, comprising administering to a subject in need with an effective amount of one or more of the disclosed HIF-1α prolyl hydroxylase inhibitors.

Yet further disclosed herein are methods for increasing the cellular immune response of a subject diagnosed with a medical condition causing a decreased cellular immunity, comprising administering to a subject in need with an effective amount of one or more of the disclosed HIF-1α prolyl hydroxylase inhibitors.

Still further disclosed herein are methods for increasing the cellular immune response of a subject having a medical condition causing a decreased cellular immunity, comprising administering to a subject in need with an effective amount of one or more of the disclosed HIF-1α prolyl hydroxylase inhibitors.

As such, the one or more HIF-1α prolyl hydroxylase inhibitor and any co-administered compounds can be administered or contacted with a cell topically, buccally, orally, intradermally, subcutaneously, mucosally in the eye, vagina, rectum, and nose, intravenously, and intramuscularly Methods Relating to the Treatment of Cancer As used herein cancer is defined herein as "an abnormal growth of cells which tend to proliferate in an uncontrolled way and, in some cases, to metastasize." As such, both metastatic and non-metastatic cancers can be treated by the disclosed methods.

Disclosed are methods for treating cancer in a subject, comprising administering to a subject with a cancer with an effective amount of one or more of the disclosed HIF-1α prolyl hydroxylase inhibitors.

Also disclosed herein are methods for treating a subject diagnosed with cancer, co-administering to a subject one or more chemotherapeutic agent or chemotherapeutic compound together with one or more of the disclosed HIF-1α prolyl hydroxylase inhibitors.

The following are non-limiting examples of malignant and non-malignant cancers. Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sézary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; and Wilms Tumor Further disclosed herein are methods for treating cancer in a subject, comprising co-administering to a subject, together with one or more chemotherapeutic agents or chemotherapeutic compounds, one or more of the disclosed HIF-1α prolyl hydroxylase inhibitors.

Also disclosed herein are methods for treating a subject diagnosed with cancer, co-administering to a subject, together with one or more chemotherapeutic agent or chemotherapeutic compound one or more of the disclosed HIF-1α prolyl hydroxylase inhibitors.

A "chemotherapeutic agent" or "chemotherapeutic compound" is a chemical compound useful in the treatment of cancer. The chemotherapeutic cancer agents that can be used in combination with the disclosed HIF-1α inhibitors include, but are not limited to, mitotic inhibitors (vinca alkaloids). These include vincristine, vinblastine, vindesine and Navelbine™ (vinorelbine, 5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCl), Hycamtin™ (topotecan HCl) and other compounds derived from camptothecin and its analogues. Another category of chemotherapeutic cancer agents that may be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed HIF-1α prolyl hydroxylase inhibitors herein can be administered in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the disclosed methods and compositions include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed HIF-1α inhibitors include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine;

interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A;

sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Methods Related to Treatment of Conditions Involving Microorganisms

Disclosed is a method for prophylactically treating a human or a mammal against infection by a microorganism, comprising administering to a subject an effective amount of one or more of the disclosed HIF-1α prolyl hydroxylase inhibitors.

Further disclosed is a method for decreasing the virulence of a microorganism when a human or a mammal is infected with a microorganism, comprising administering to a subject an effective amount of one or more of the disclosed HIF-1α prolyl hydroxylase inhibitors.

Yet further disclosed is a method for treating an infection in a subject caused by a microorganism, comprising administering to a subject an effective amount of one or more of the disclosed HIF-1α prolyl hydroxylase inhibitors.

Still further disclosed is a method for treating a subject diagnosed with an infection caused by a microorganism, comprising administering to a subject an effective amount of one or more of the disclosed HIF-1α prolyl hydroxylase inhibitors.

Also disclosed is a method for preventing transmission of a disease caused by a microorganism from a subject to a subject, comprising administering to a subject an effective amount of one or more of the disclosed HIF-1α prolyl hydroxylase inhibitors.

Still yet further disclosed is a method for preventing infection of a human or a mammal during a surgical procedure, comprising administering to a subject an effective amount of one or more of the disclosed HIF-1α prolyl hydroxylase inhibitors.

The microorganism can be any benign or virulent microorganism, for example, bacteria, viruses, yeasts, fungi, or parasites. The following are non-limiting examples of microorganisms that can be affected by the disclosed HIF-1α prolyl hydroxylase inhibitors. By the term "affected" is meant, the virulence of the microorganism is reduced, diminished or eliminated. The cause of the reduction, diminishment, or elimination of the virulence can be from the stabilization of HIF-1 and/or from the increased level of phagocytosis due to the administration of one or more of the disclosed HIF-1α prolyl hydroxylase inhibitors. *Acinetobacter calcoaceticus, Acinetobacter haemolyticus, Aeromonas hydrophila, Agrobacterium tumefaciens, Bacillus anthracis, Bacillus halodurans, Bacillus subtilis, Bacteroides distasonis, Bacteroides eggerthii, Bacteroides fragilis, Bacteroides ovalus, Bacteroides* 3452A homology group, *Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Brucella melitensis, Burkholderia cepacia, Burkholderia pseudomallei, Campylobacter coli, Campylobacter fetus, Campylobacter jejuni, Caulobacter crescentus, Citrobacter freundii, Clostridium difficile, Clostridium perfringens, Corynebacterium diphtheriae, Corynebacterium glutamicum, Corynebacterium ulcerans, Edwardsiella tarda, Enterobacter aerogenes, Erwinia chrysanthemi, Enterobacter cloacae, Enterococcus faecalis, Enterococcus faecium, Escherichia coli, Francisella tularensis, Gardnerella vaginalis, Haemophilus ducreyi, Haemophilus haemolyticus, Haemophilus influenzae, Haemophilus parahaemolyticus, Haemophilus parainfluenzae, Helicobacter pylori, Klebsiella oxytoca, Klebsiella pneumoniae, Kluyvera cryocrescens, Legionella pneumophila, Listeria innocua, Listeria monocytogenes, Listeria welshimeri, Methanosarcina acetivorans, Methanosarcina mazei, Morganella morganii, Mycobacterium avium, Mycobacterium intracellulare, Mycobacterium leprae, Mycobacterium tuberculosis, Mesorhizobium loti, Neisseria gonorrhoeae, Neisseria meningitidis, Pasteurella haemolytica, Pasteurella multocida, Providencia alcalifaciens, Providencia rettgeri, Providencia stuartii, Proteus mirabilis, Proteus vulgaris, Pseudomonas acidovorans, Pseudomonas aeruginosa, Pseudomonas alcaligenes, Pseudomonas fluorescens, Pseudomonas putida, Ralstonia solanacearum, Salmonella enterica* subsp. *enteridtidis, Salmonella enterica* subsp. *paratyphi, Salmonella enterica,* subsp. *typhimurium, Salmonella enterica,* subsp. *typhi, Serratia marcescens, Shigella dysenteriae, Shigella flexneri, Shigella sonnei, Sinorhizobium meliloti, Staphylococcus aureus, Streptococcus criceti, Staphylococcus epidemmidis, Staphylococcus haemolyticus, Staphylococcus hominis, Staphylococcus hyicus, Staphylococcus intermedius, Stenotrophomonas maltophilia, Staphylococcus saccharolyticus, Staphylococcus saprophyticus, Staphylococcus sciuri, Streptomyces avermitilis, Streptomyces coelicolor, Streptococcus agalactiae, Streptococcus pneumoniae, Streptococcus pyogenes Sulfobalblobus soffiataricus, Thermotoga maritima, Vibrio cholerae, Vibrio parahaemolyticus, Vogesella indigofera, Xanthomonas axonopodis, Xanthomonas campestris, Yersinia enterocolitica, Yersinia intermedia, Yersinia pestis,* and *Yersinia pseudotuberculosis*

Methods Relating to Vaccination or Innoculation

Disclosed herein are methods for enhancing the effectiveness of a vaccine, comprising co-administering to a subject a vaccine in combination with one or more HIF-1α prolyl hydroxylase inhibitors.

Non-limiting examples of vaccines are those for stimulating antibodies against hepatitis, influenza, measles, rubella, tetanus, polio, rabies, and the like.

Therefore, the disclosed methods includes administering, or in the case of contacting cells in vitro, in vivo or ex vivo, the one or more HIF-1α prolyl hydroxylase inhibitors and any co-administered compounds topically, buccally, orally, intradermally, subcutaneously, mucosally in the eye, vagina, rectum, and nose, intravenously, and intramuscularly.

The following are non-limiting examples of methods according to the present disclosure.

A method for increasing HIF-1 stabilization in a cell, comprising contacting a cell in vivo, in vitro, or ex vivo with an effective amount of one or more of the disclosed HIF-1α prolyl hydroxylase inhibitors.

A method for increasing the cellular immune response of a subject in need of increased cellular immunity, comprising administering to a subject in need with an effective amount of one or more of the disclosed HIF-1α prolyl hydroxylase inhibitors.

A method for increasing the cellular immune response of a subject diagnosed with a medical condition causing a decreased cellular immunity, comprising administering to a subject in need an effective amount of one or more of the disclosed HIF-1α prolyl hydroxylase inhibitors.

A method for increasing the cellular immune response of a subject diagnosed with a medical condition causing a decreased cellular immunity, comprising administering to the subject an effective amount of one or more of the disclosed HIF-1α inhibitors.

A method for increasing the cellular immune response of a subject having a medical condition causing a decreased cellular immunity, said method comprising administering to the subject in need an effective amount of one or more of the disclosed HIF-1α inhibitors.

A method for treating cancer in a subject, comprising administering to the subject having cancer an effective amount of one or more of the disclosed HIF-1α inhibitors.

A method for treating a subject diagnosed with cancer by stabilizing the level of cellular HIF-1 thereby increasing the immune response in the subject, comprising administering to the subject diagnosed with cancer with an effective amount of one or more HIF-1α inhibitors.

A method for treating a subject diagnosed with cancer by stabilizing the level of cellular HIF-1 thereby increasing the immune response in the subject, comprising administering to the subject diagnosed with cancer an effective amount of a composition comprising one or more chemotherapeutic agents or chemotherapeutic compounds and one or more HIF-1α prolyl hydroxylase inhibitors.

A method for treating cancer in a subject by stabilizing the level of cellular HIF-1 thereby increasing the immune response in the subject, comprising administering to the subject with cancer with an effective amount of one or more HIF-1α inhibitors.

A method for treating cancer in a subject by stabilizing the level of cellular HIF-1 thereby increasing the immune response in the subject, said method comprising administering to the subject an effective amount of a composition comprising one or more chemotherapeutic agents or chemotherapeutic compounds and one or more HIF-1α prolyl hydroxylase inhibitors.

A method for treating a subject diagnosed with cancer, comprising administering to the subject diagnosed with cancer with an effective amount of one or more HIF-1α inhibitors.

A method for treating a subject diagnosed with cancer, comprising administering to the subject diagnosed with cancer with an effective amount of a composition comprising one or more chemotherapeutic agents or chemotherapeutic compounds and one or more HIF-1α prolyl hydroxylase inhibitors.

A method for treating a subject diagnosed with cancer by co-administering to the subject one or more chemotherapeutic agents or chemotherapeutic compounds and one or more of the disclosed HIF-1α prolyl hydroxylase inhibitors.

A method for treating a subject having cancer by co-administering to the subject one or more chemotherapeutic agents or chemotherapeutic compounds and one or more of the disclosed HIF-1α prolyl hydroxylase inhibitors.

A method for prophylactically treating infection in a subject against an infection, comprising administering to the subject an effective amount of one or more of the disclosed HIF-1α inhibitors.

A method for treating an infection in a subject caused by a microorganism, comprising administering to the subject an effective amount of one or more of the disclosed HIF-1α prolyl hydroxylase inhibitors.

A method for treating infection in a subject wherein the infection is caused by a pathogen chosen from bacteria, viruses, yeasts, fungi, or parasites, comprising administering to the subject with an infection with an effective amount of one or more HIF-1α inhibitors A method for treating a subject diagnosed with an infection caused by a microorganism, comprising administering to the subject an effective amount of one or more of the disclosed HIF-1α prolyl hydroxylase inhibitors.

A method for preventing transmission of a disease caused by a microorganism from one subject to another subject, comprising administering to the subject an effective amount of one or more of the disclosed HIF-1α prolyl hydroxylase inhibitors.

A method for enhancing the effectiveness of a vaccine, comprising co-administering to a subject a vaccine in combination with one or more of the disclosed HIF-1α prolyl hydroxylase inhibitors.

A method for enhancing the effectiveness of a vaccine, comprising administering to a subject a composition comprising a vaccine in combination with one or more of the disclosed HIF-1α prolyl hydroxylase inhibitors.

A method for inhibiting hypoxia-inducible factor-1alpha (HIF-1α) 4-prolyl hydroxylase activity in a subject thereby stabilizing the cellular level of HIF-1, comprising administering to the subject an effective amount of one or more of the disclosed HIF-1α 4-prolyl hydroxylase inhibitors.

A method for modulating the cellular level of hypoxia-inducible factor-1 (HIF-1) in a subject, comprising contacting the subject with an effective amount of one or more an effective amount of one or more of the disclosed HIF-1α prolyl hydroxylase inhibitors.

A method for increasing the cellular level of HIF-1 in a subject during a state of normoxia, comprising administering to a subject an effective amount of one or more an effective amount of one or more of the disclosed HIF-1α prolyl hydroxylase inhibitors.

A method for treating anemia in a subject, comprising administering to the subject an effective amount of one or more of the disclosed HIF-1α prolyl hydroxylase inhibitors.

A method for treating a subject diagnosed as having anemia, comprising administering to the subject an effective amount of one or more of the disclosed HIF-1α prolyl hydroxylase inhibitors.

A method for increasing angiogenesis in a subject, comprising administering to the subject an effective amount of one or more of the disclosed HIF-1α prolyl hydroxylase inhibitors.

A method for treating a subject having a need for increased angiogenesis, comprising administering to the subject an effective amount of one or more of the disclosed HIF-1α prolyl hydroxylase inhibitors.

A method for treating sepsis in a subject, comprising administering to the subject an effective amount of one or more of the disclosed HIF-1α prolyl hydroxylase inhibitors.

A method for treating a subject diagnosed as having sepsis, comprising administering to a subject an effective amount of one or more HIF-1α prolyl hydroxylase inhibitors.

A method for treating peripheral vascular disease in a subject, comprising administering to a subject an effective amount of one or more of the disclosed HIF-1α prolyl hydroxylase inhibitors.

A method for treating a subject diagnosed as having peripheral vascular disease, comprising administering to a subject an effective amount of one or more of the disclosed HIF-1α prolyl hydroxylase inhibitors.

A method for treating a wound in a subject, comprising administering to a subject an effective amount of one or more of the disclosed HIF-1α prolyl hydroxylase inhibitors.

A method for treating a subject having a wound, comprising administering to a subject an effective amount of one or more of the disclosed HIF-1α prolyl hydroxylase inhibitors.

A method for preventing infection of a wound in a subject, comprising administering to a subject an effective amount of one or more of the disclosed HIF-1α prolyl hydroxylase inhibitors.

A method for treating diabetes in a subject, comprising administering to the subject an effective amount of one or more of the disclosed HIF-1α prolyl hydroxylase inhibitors.

A method for treating a subject diagnosed as having diabetes, comprising administering to the subject an effective amount of one or more of the disclosed HIF-1α prolyl hydroxylase inhibitors.

A method for treating hypertension in a subject, comprising administering to the subject an effective amount of one or more of the disclosed HIF-1α prolyl hydroxylase inhibitors.

A method for treating a subject diagnosed as having hypertension, comprising administering to the subject an effective amount of one or more of the disclosed HIF-1α prolyl hydroxylase inhibitors.

Procedures

EGLN-1 Activity Assay

The EGLN-1 (or EGLN-3) enzyme activity is determined using mass spectrometry (matrix-assisted laser desorption ionization, time-of-flight MS, MALDI-TOF MS. Recombinant human EGLN-1-179/426 is prepared as described above and in the Supplemental Data. Full-length recombinant human EGLN-3 is prepared in a similar way, however it is necessary to use the His-MBP-TVMV-EGLN-3 fusion for the assay due to the instability of the cleaved protein. For both enzymes, the HIF-1α peptide corresponding to residues 556-574 is used as substrate. The reaction is conducted in a total volume of 50 µL containing TrisCl (5 mM, pH 7.5), ascorbate (120 µM), 2-oxoglutarate (3.2 µM), HIF-1α (8.6 µM), and bovine serum albumin (0.01%). The enzyme, quantity predetermined to hydroxylate 20% of substrate in 20 minutes, is added to start the reaction. Where inhibitors are used, compounds are prepared in dimethyl sulfoxide at 10-fold final assay concentration. After 20 minutes at room temperature, the reaction is stopped by transferring 10 µL of reaction mixture to 50 µL of a mass spectrometry matrix solution (α-cyano-4-hydroxycinnamic acid, 5 mg/mL in 50% acetonitrile/0.1% TFA, 5 mM $NH_4PO_4$). Two microliters of the mixture is spotted onto a MALDI-TOF MS target plate for analysis with an Applied Biosystems (Foster City, Calif.) 4700 Proteomics Analyzer MALDI-TOF MS equipped with a Nd:YAG laser (355 nm, 3 ns pulse width, 200 Hz repetition rate). Hydroxylated peptide product is identified from substrate by the gain of 16 Da. Data defined as percent conversion of substrate to product is analyzed in GraphPad Prism 4 to calculate $IC_{50}$ values.

VEGF ELISA Assay

HEK293 cells are seeded in 96-well poly-lysine coated plates at 20,000 cells per well in DMEM (10% FBS, 1% NEAA, 0.1% glutamine). Following overnight incubation, the cells are washed with 100 µL of Opti-MEM (Gibco, Carlsbad, Calif.) to remove serum. Compound in DMSO is serially diluted (beginning with 100 µM) in Opti-MEM and added to the cells. The conditioned media is analyzed for VEGF with a Quantikine human VEGF immunoassay kit (R&D Systems, Minneapolis, Minn.). Optical density measurements at 450 nm are recorded using the Spectra Max 250 (Molecular Devices, Sunnyvale, Calif.). Data defined as % of DFO stimulation is used to calculate $EC_{50}$ values with GraphPad Prism 4 software (San Diego, Calif.).

Mouse Ischemic Hindlimb Study

All animal work is conducted in accordance with the Guide for the Care and Use of Laboratory Animals (National Academy of Sciences; Copyright©1996). Used in these experiments were 9-10 week old male $C_{57}Bl/6$ mice from Charles River Laboratory (Portage, Mich.). The mice are orally dosed with vehicle (aqueous carbonate buffer, 50 mM; pH 9.0) or with the compound to be tested in vehicle at 50 mg/kg or 100 mg/kg. The animals are dosed three times: day 1 at 8 AM and 5 PM, and on day 2 at 8 AM. One hour after the first dose, unilateral arterial ligation is performed under anesthesia using isoflurane. The femoral artery is ligated proximal to the origin of the popliteal artery. The contralateral limb undergoes a sham surgical procedure. Ligation is performed in an alternating fashion between right and left hindlimbs. Two hours after the 8 AM dosing on day 2, blood is obtained by ventricular stick while the mice are anesthetized with isoflurane. Serum samples for EPO analysis are obtained using gel clot serum separation tubes. Heart, liver, and gastrocnemius muscles are harvested, snap-frozen in liquid nitrogen, and stored in –80° C. until use.

Mouse Serum EPO Assay

The mouse serum EPO is detected using Mouse Quantikine Erythropoietin ELISA kit from R&D Systems according to manufacturer's instructions.

Mouse Tissue HIF Western Blot Analysis

Tissues from mice stored at –80° C. are powdered with mortar and pestle chilled with liquid nitrogen. Nuclear extracts are prepared using an NE-PER kit (Pierce Biotechnology). For immunoprecipitation, nuclear extract is added to monoclonal antibody to HIF-1α (Novus, Littleton, Colo.) at a tissue to antibody ratio of 200:1. The suspension is incubated in a conical micro centrifuge tube for 4 hours at 4° C. Protein A/G-coupled agarose beads (40 µL of a 50% suspension) are then added to the tube. Following overnight tumbling at 4° C., the beads are washed 3 times with ice-cold phosphate buffered saline. The beads are then prepared for SDS-PAGE with 40 µL of Laemmli sample buffer. Proteins separated on SDS-PAGE are transferred onto nitrocellulose sheets with XCell-II Blot Module system (Invitrogen, Carlsbad, Calif.). The blots are blocked with 5% BSA prior to incubation with a rabbit antibody to HIF-1α at 1:100 dilution (Novus). The blots are then washed with Tris-buffered saline/Tween-20 buffer and incubated with horseradish peroxidase-conjugated goat anti-rabbit secondary antibody (Pierce, Rockford, Ill.). Blots are developed with the ECL reagent (Amersham, Piscataway, N.J.). Images of blots are captured with an Epson Expression 1600 scanner.

Table VIII below provides non-limiting examples of the in vivo response for compounds according to the present disclosure, for example, HIFPH2 (EGLN1) inhibition and VEGF stimulation.

TABLE VIII

| No. | Compound | HIFPH2 IC$_{50}$ (μM) | VEGF IC$_{50}$ (μM) |
|---|---|---|---|
| C17 | 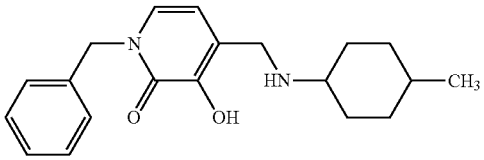 [SMILES: CC1CCC(NCc2ccn(Cc3ccccc3)c(=O)c2O)CC1]<br>1-benzyl-3-hydroxy-4-[(4-methylcyclohexylamino)methyl]pyridin-2(1H)-one | 11 | 27.4 |
| C35 | 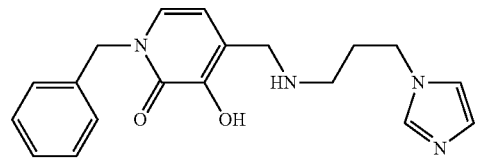 [SMILES: O=c1c(O)c(CNCCCn2ccnc2)ccn1Cc1ccccc1]<br>1-benzyl-3-hydroxy-4-{[3-(1H-imidazol-1-yl)propylamino]methyl}pyridin-2(1H)-one | 12 | 42.5 |
| C14 | 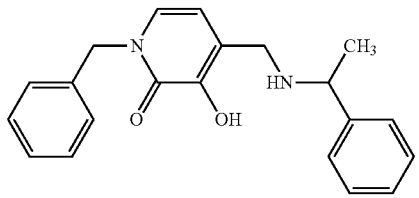 [SMILES: CC(NCc1ccn(Cc2ccccc2)c(=O)c1O)c1ccccc1]<br>1-benzyl-3-hydroxy-4-[(1-phenylethylamino)methyl]pyridin-2(1H)-one | 12 | 20.6 |
| B5 | 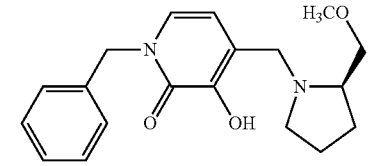 [SMILES: COC[C@H]1CCCN1Cc1ccn(Cc2ccccc2)c(=O)c1O]<br>(R)-1-benzyl-3-hydroxy-4-{[2-(methoxymethyl)pyrrolidin-1-yl]methyl}pyridin-2(1H)-one | 9 | 53 |
| C33 | 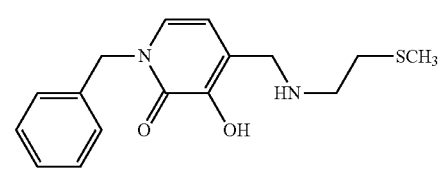 [SMILES: CSCCNCc1ccn(Cc2ccccc2)c(=O)c1O]<br>1-benzyl-3-hydroxy-4-{[2-(methylthio)ethylamino]methyl}pyridin-2(1H)-one | 16 | 53 |

TABLE VIII-continued

| No. | Compound | HIFPH2 IC$_{50}$ (µM) | VEGF IC$_{50}$ (µM) |
|---|---|---|---|
| B14 | 1-benzyl-3-hydroxy-4-{[4-(6-chloropyridazin-3-yl)piperazin-1-yl]methyl}pyridin-2(1H)-one | 11 | 78 |
| C19 | 3-[(1-benzyl-3-hydroxy-2-oxo-1,2-dihydropyridin-4-yl)methylamino]azepan-2-one | 12 | 62.9 |
| B9 | 1-benzyl-3-hydroxy-4-[(4-benzylpiperazin-1-yl)methyl]pyridin-2(1H)-one | 17 | 12.6 |
| A18 | 1-(2-methoxybenzyl)-3-hydroxy-4-(azepan-1-ylmethyl)pyridin-2(1H)-one | 18 | 29.2 |
| D10 | 1-[(4-methylphenyl)sulfonyl]-3-hydroxy-4-(1,4'-bipiperidin-1'-ylmethyl)pyridin-2(1H)-one | 4.4 | 27 |

TABLE VIII-continued

| No. | Compound | HIFPH2 IC$_{50}$ (μM) | VEGF IC$_{50}$ (μM) |
|---|---|---|---|
| D14 | 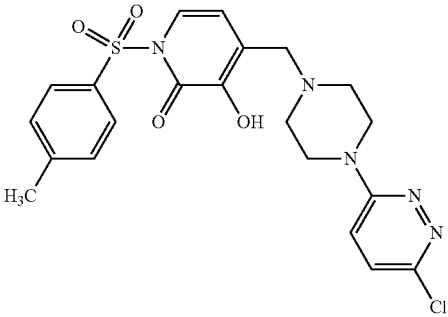 [SMILES: Cc1ccc(S(=O)(=O)n2ccc(CN3CCN(c4ccc(Cl)nn4)CC3)c(O)c2=O)cc1]<br>1-[(4-methylphenyl)sulfonyl]-3-hydroxy-4-{[4-(6-chloropyridazin-3-yl)piperazin-1-yl]methyl}pyridin-2(1H)-one | 12 | 19 |
| C1 | 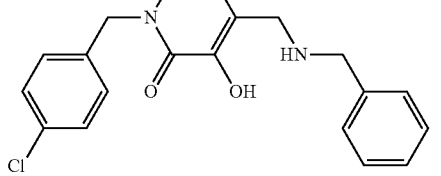<br>1-(4-chlorobenzyl)-3-hydroxy-4-[(4-benzylamino)methyl]pyridin-2(1H)-one | 12 | 42 |
| A41 | 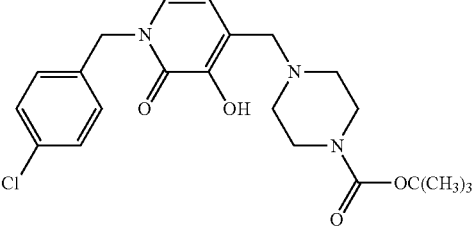<br>tert-butyl 4-{[1-(4-chlorobenzyl)-3-hydroxy-2-oxo-1,2-dihydropyridin-4-yl]methyl}piperazine-1-carboxylate | 14 | 16.6 |
| E33 | 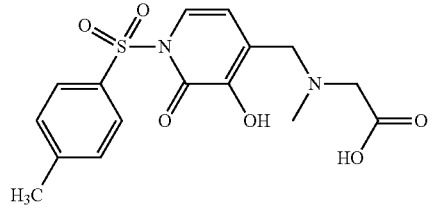 [SMILES: Cc1ccc(S(=O)(=O)n2ccc(CN(C)CC(=O)O)c(O)c2=O)cc1]<br>2-{[(3-hydroxy-2-oxo-1-tosyl-1,2-dihydropyridin-4-yl)methyl](methyl)amino}acetic acid | 21 | 2.1 |
| F3 | 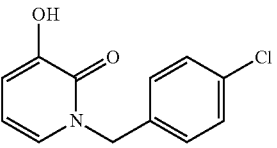<br>1-(4-chlorobenzyl)-3-hydroxypyridin-2(1H)-one | 1.2 | 7.4 |

TABLE VIII-continued

| No. | Compound | HIFPH2 IC$_{50}$ (µM) | VEGF IC$_{50}$ (µM) |
|---|---|---|---|
| F2 | 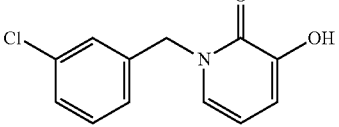<br>1-(3-chlorobenzyl)-3-hydroxypyridin-2(1H)-one | 5 | >100 |

Compound F2 was further tested in the mouse serum EPO assay described herein above and found to have an EPO EC$_{50}$=14 µM.

Enhanced Neutrophil Activity

One aspect of the disclosure relates to the increased neutrophil activity and increased neutrophil life that the disclosed compounds can provide. The following provides methods and examples of increased phagocytosis by the disclosed compounds. In the examples below the *Staphylococcus aureus* Newman cell strain is ATCC #25904 and the methicillin resistant *Staphylococcus aureus* strain is ATCC #33591, and the U937 cell line is ATCC # CRL-1593.2. The HaCaT cells were generated by the procedure of Boukamp P et al., "Normal keratinization in a spontaneously immortalized aneuploid human keratinocyte cell line." *J Cell Biol*. (1988) March: 106(3):761-71.

For bacterial assays, *S. Aureus* (ATCC 33591) can be grown in Todd-Hewitt broth (THB) to logarithmic phase (OD$_{600}$ of 0.4 or ~5×10$^7$ cfu/mL) and then pelleted, washed, and resuspended in PBS or RPMI 1640 tissue-culture medium to the desired concentration. Venous blood from healthy volunteers can be used for whole blood and neutrophil isolation. Neutrophils can be purified using the PolyMorphPrep Kit (Axis Shield) in accordance with manufacturer's instructions. Human monocytic cell line U937 can be propagated in RPMI 1640 plus 10% fetal calf serum, 1 mmol/L NaPyr, 10 mmol/L HEPES, and glucose. Whole blood or phagocytic cells can be preincubated with mimosine (Sigma-Aldrich) (0-500 µmol/L) for 2-4 hours then challenged with *S. Aureus* (either 10$^5$ cfu in 100 µL added to 300 µL of whole blood or at an MOI of 1 bacterium/cell for isolated phagocytes). Aliquots are then plated on THB agar after 30 (whole blood and neutrophils) or 60 (U937 monocytes) min for enumeration of surviving *S. Aureus* colony-forming units.

EXAMPLE 5

Isolated human neutrophils were pre-incubated for 1 hour at 37° C. with a control consisting of dimethyl sulfoxide (DMSO), 50 µM and 200 µM of a compound disclosed in Table VIII. *Staphylococcus aureus* (Newman strain) was then added to the neutrophils at an MOI of approximately 0.1 (1 bacterium for every 10 neutrophils). Samples were taken at 60 and 90 minutes wherein the neutrophils were lysed with water, and the total bacteria remaining were enumerated on Todd-Hewitt broth (THB) agar plates.

Figure 2:
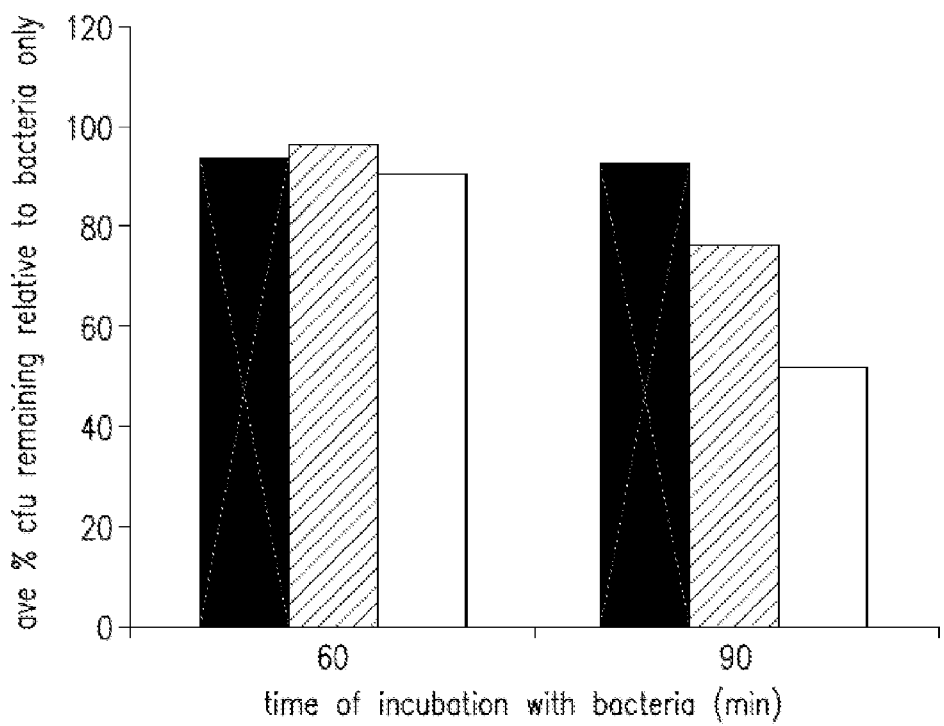
FIG. 2 depicts the enhancement of neutrophil killing of S. aureus (Newman strain) with 50 µM and 200 µM of a compound disclosed in Table VIII versus control (DMSO) at 60 and 90 minutes.

FIG. 2 depicts the effectiveness of a compound disclosed in Table VIII in providing enhanced killing of *S. aureus* (Newman strain) at concentrations of 50 µM and 200 µM versus control. As can be seen in FIG. 2, at 90 minutes post-infection, approximately half of the colony forming units are absent at a concentration of 200 µM.

EXAMPLE 6

Cells from the human monocyte cell line U937 were pre-incubated for 2 hours at 37° C. under an atmosphere of 5% CO$_2$ with a control consisting of DMSO and 10 µM of a compound disclosed in Table VIII. *Staphylococcus aureus* (virulent Newman strain) was then added to the cells at an MOI of approximately 1 (1 bacterium for every 1 cell). Samples are drawn at 30, 60, 90 and 120 minutes post-infection. The U937 cells were lysed with Triton™, and the amount of bacteria remaining were enumerated on THB agar plates.

Figure 3:
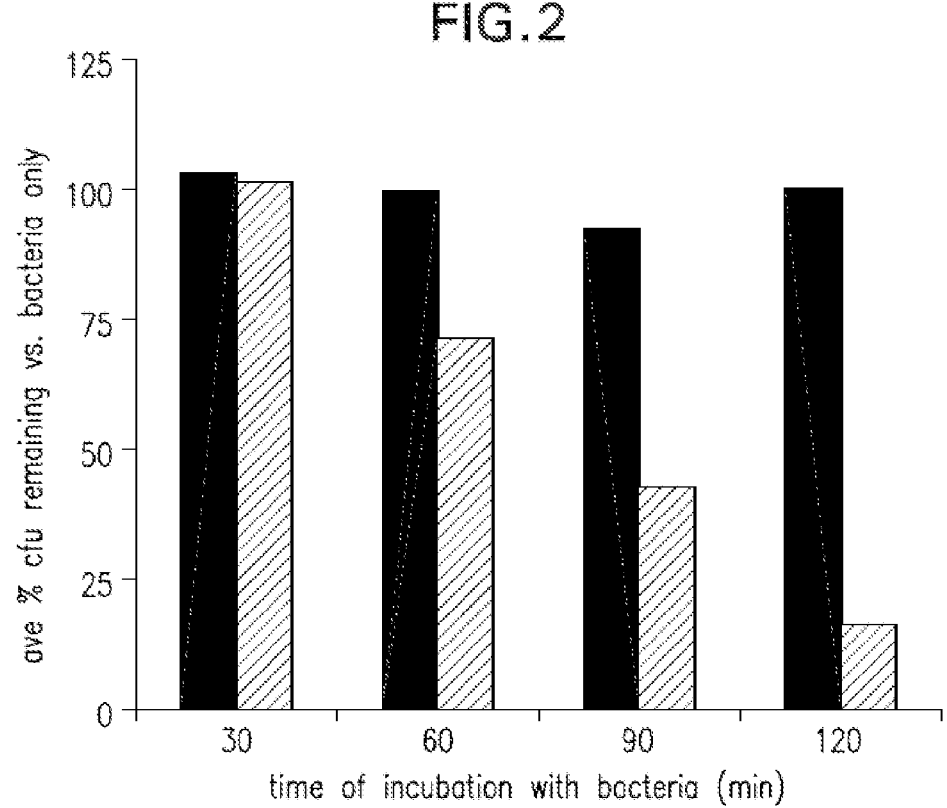
FIG. 3 depicts the enhancement of human monocyte cell line (U937) against S. aureus (Newman strain) by 10 µM a compound disclosed in Table VIII versus untreated samples.

As depicted in FIG. 3, 4-prolyl hydroxylase inhibitor a compound disclosed in Table VIII is effective in killing *S. aureus* when compared to a control (DMSO). At 120 minutes, a compound disclosed in Table VIII produces an 84% kill of Newman strain *S. aureus* when the monocyte cells are treated with 10 µM of a compound disclosed in Table VIII, thereby showing increased phagocytosis due to extended neutrophil life span.

EXAMPLE 7

Two samples of cells from the human monocyte cell line U937 were pre-treated with 10 µM of a compound disclosed in Table VIII. One sample was pre-incubated for 1 hour and the other sample pre-incubated for 2 hours, both at 37° C. under an atmosphere of 5% CO$_2$. *S. aureus* (virulent Newman strain) was then added to the cells at an MOI of approximately 1-2 (1-2 bacteria for every 1 cell). Aliquots of cells were removed from each sample at 30, 60, 90, and 120 minutes post-infection, the U937 cells were immediately lysed with Triton™, and total of remaining bacteria remaining were enumerated on THB agar plates.

Figure 4:
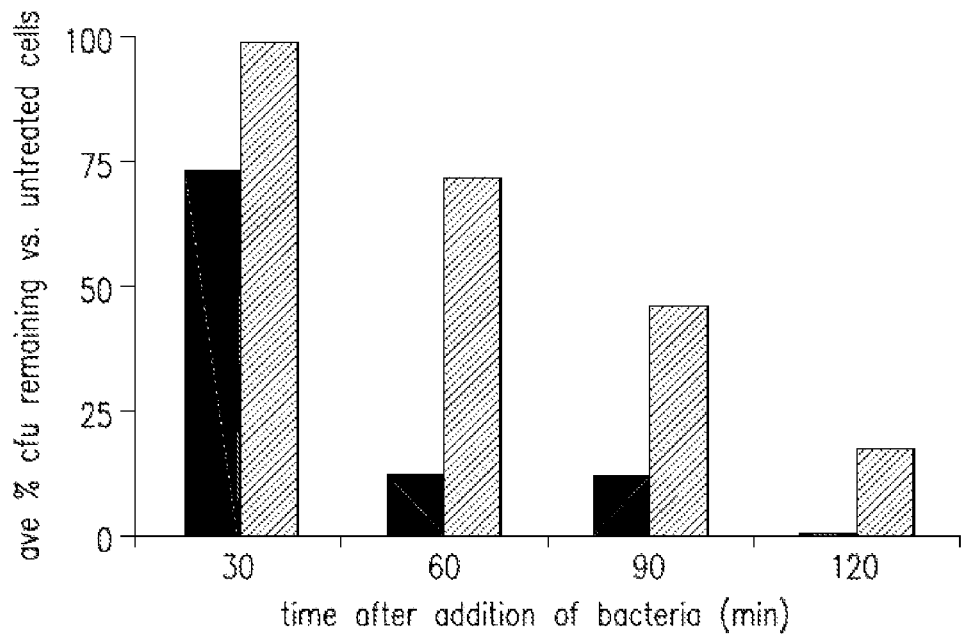
FIG. 4 depicts the average percent surviving bacteria in treated vs. untreated U937 cells after infection with S. aureus (Newman strain) after 1 hour pre-treatment (black) or 2 hour (hatched) pre-treatment with 10 µM of a compound disclosed in Table VIII.

As depicted in FIG. 4, U937 monocyte cells pre-treated with 10 µM of a compound disclosed in Table VIII for 1 hour (black bars) had almost no colony forming units present 120 minutes post-infection, whereas the cells pre-treated two hours prior to infection had approximately 15% colony forming units present as compared to cells that were untreated. In addition, FIG. 4 indicates that within 1 hour after the U937 monocyte cells had bee exposed to *S. aureus* (Newman strain), the number of colony forming units present was significantly reduced relative to cells receiving no HIF-1α inhibitor.

EXAMPLE 8

Two samples of cells from the human monocyte cell line U937 were pre-treated with 10 µM of a compound disclosed in Table VIII for 1 at 37° C. under an atmosphere of 5% CO$_2$. *S. aureus* (Newman strain) was added to one sample and to the other was added methicillin-resistant *S. aureus* (MRSA). Both bacteria were added at an MOI of approximately 2-3 (2-3 bacteria for every 1 cell). Aliquots of cells were removed from each sample at 30, 60, 90, and 120 minutes post-infection. The U937 cells were immediately lysed with Triton™, and total of remaining bacteria remaining were enumerated on THB agar plates.

Figure 5:
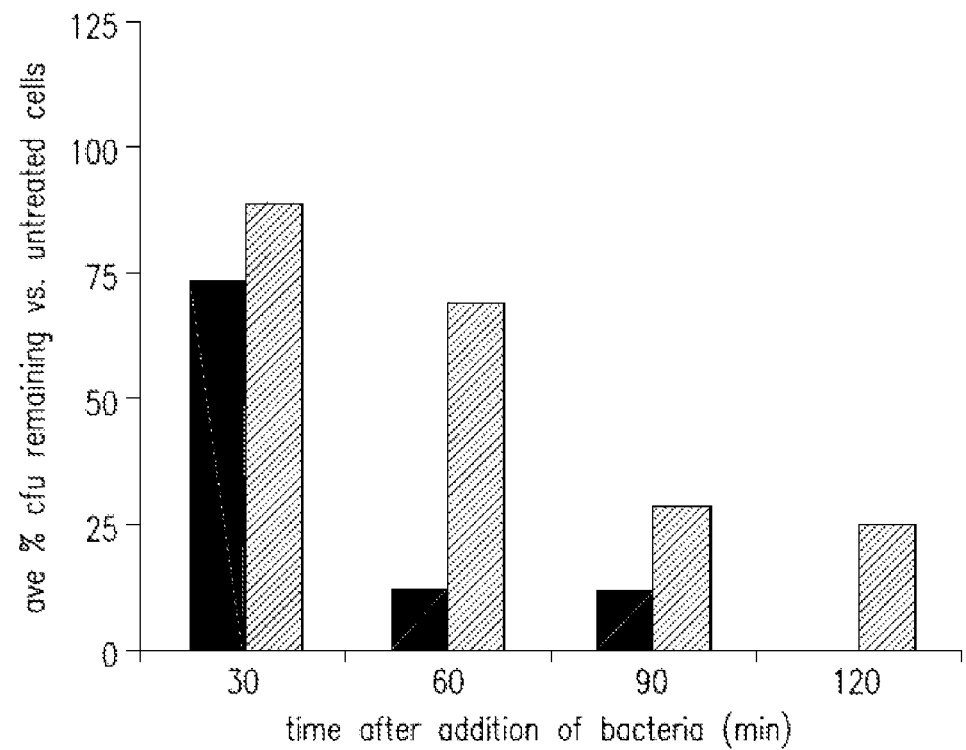
FIG. 5 depicts the average percent surviving bacteria in treated vs. untreated U937 cells after infection with two strains of S. aureus, Newman (black) or methicillin resistant S. aureus (MRSA) (hatched), after 1 hour pre-treatment with 10 µM of a compound disclosed in Table VIII.

As depicted in FIG. 5, at 120 minutes post-infection, the MRSA infected cells had only 25% of the average percentage of colony forming units present when compared to control as represented by the black bars. Also depicted in FIG. 5, at 60 minutes post-infection, the Newman strain of *S. aureus* had only approximately 12% of the average percentage of colony forming units present when compared to control, and almost no colony forming units present at 120 minutes post-infection as represented by the hatched bars.

EXAMPLE 9

Two samples of cells from the human monocyte cell line U937 treated with 10 µM a compound disclosed in Table VIII were infected with either *S. aureus* (Newman strain) and methicillin-resistant *S. aureus* (MRSA). Both bacteria were added at an MOI of approximately 2-3 (2-3 bacteria for every 1 cell). Aliquots of cells were removed from each sample at 30, 60, 90, and 120 minutes post-infection. The U937 cells were immediately lysed with Triton™, and total remaining bacteria were enumerated on THB agar plates.

Figure 6:
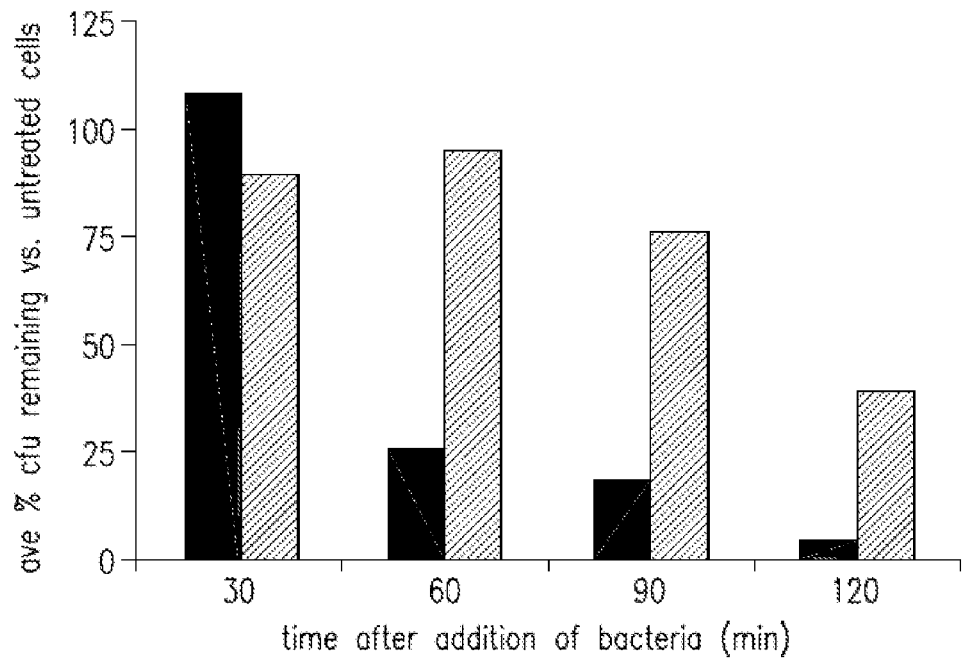
FIG. 6 depicts the average percent surviving bacteria in treated vs. untreated U397 cells after infection with two strains of S. aureus, Newman (black) or MRSA (hatched) and treatment with 10 µM of a compound disclosed in Table VIII.

As depicted in FIG. 6, even without pre-treatment with a compound disclosed in Table VIII, at 60 minutes post-infection, the Newman strain of *S. aureus* had only 25% of the average percentage of colony forming units present when compared to control as represented by the black bars. The MRSA strain was reduced to less than approximately 40% of the average percentage of colony forming units present when compared to control as represented by the hatched bars.

EXAMPLE 10

Three samples of cells from the human monocyte cell line U937 were treated with 100 µM mimosine, 2 µg/mL vancomycin or 10 µM of a compound disclosed in Table VIII. Each sample was infected with either *S. aureus* (Newman strain) or methicillin-resistant *S. aureus* (MRSA). Both bacteria were added at an MOI of approximately 2-3 (2-3 bacteria for every 1 cell). At 120 minutes post-infection aliquots were withdrawn from all six samples and the U937 cells were immediately lysed with Triton™, and total remaining bacteria were enumerated on THB agar plates.

Figure 7:
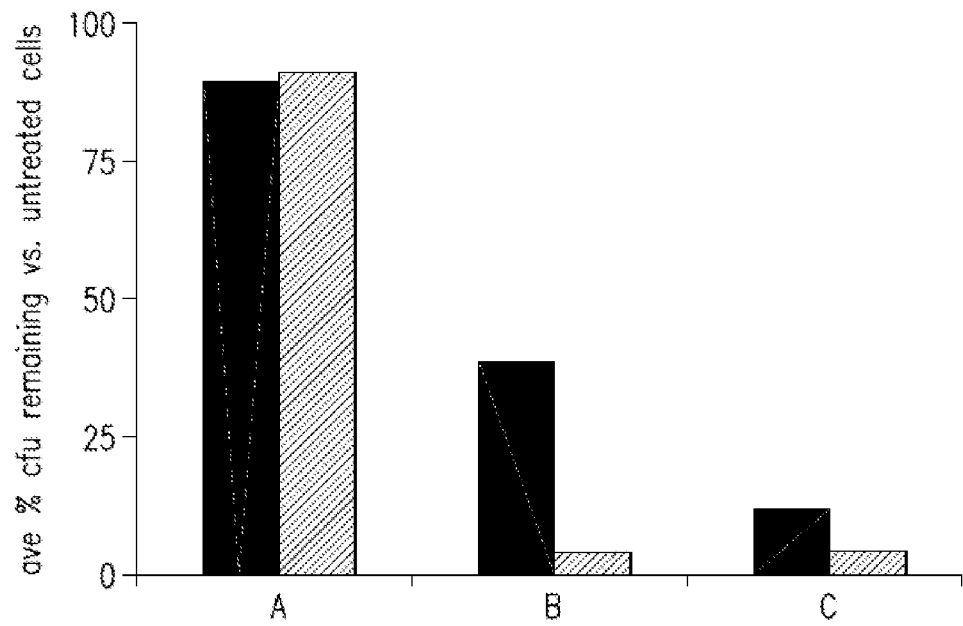
FIG. 7 depicts the average percent surviving bacteria in treated vs. untreated U937 cells after infection with two strains of S. aureus, Newman (hatched bars) or MRSA (black bars), following treatment with 100 mM mimosine (A), 10 µM of a compound disclosed in Table VIII (B), or 2 mg/mL of vancomycin (C) at 2 hours post-infection.

As depicted in FIG. 7, 10 µM a compound disclosed in Table VIII enhanced kill of both bacterial strains, i.e., *S. aureus*, Newman (hatched bars) or MRSA (black bars), when compared to mimosine treated cells. Referring to the hatched bars representing Newman strain, as further depicted in FIG. 7, the sample treated with 10 µM a compound disclosed in Table VIII had a lower average percentage of colony forming units present than the cells treated with vancomycin. The U937 cells infected with MRSA (black bars) had approximately 40% of the colony forming units present versus untreated cells and less than half the number of those treated with mimosine.

Figure 8:
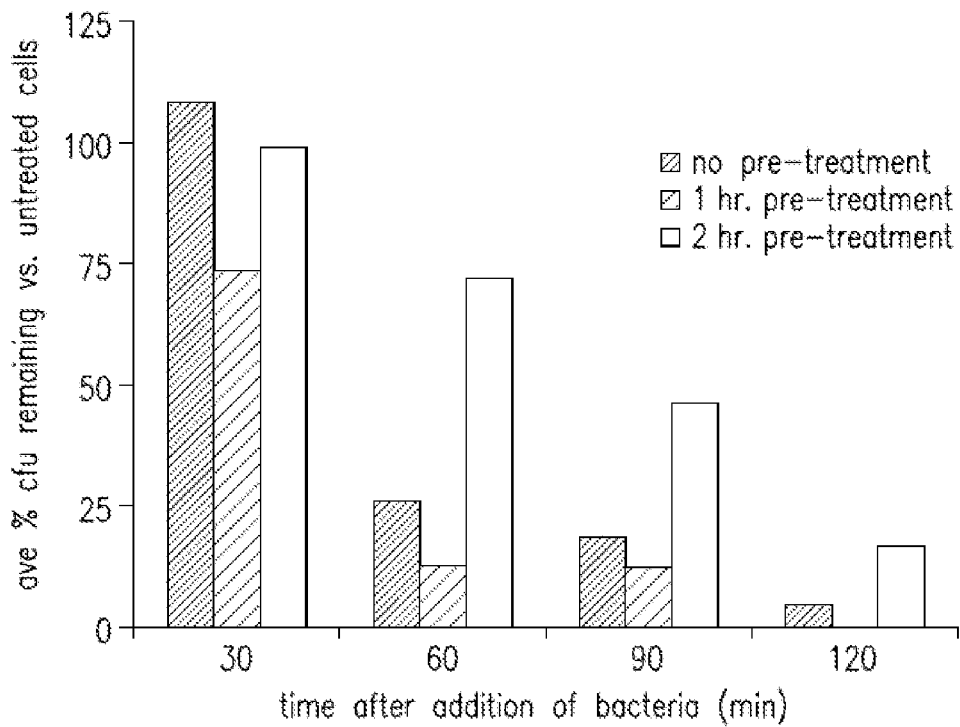
FIG. 8 depicts the average percent surviving bacteria in treated vs. untreated U937 cells after infection with S. aureus (Newman) following no pre-treatment, 1 hour pre-treatment, or 2 hour pre-treatment with 10 µM of a compound disclosed in Table VIII.

FIG. 8 depicts the average percentage of colony forming units present (Newman strain) versus control for human monocyte cells (U937) at 30, 60, 90, and 120 minutes post-infection, when treated with 10 µM a compound disclosed in Table VIII. The black bars represent treatment with a compound disclosed in Table VIII beginning at the time of infection with *S. aureus*, the hatched bars represent cells pretreated with a compound disclosed in Table VIII and white bars represent cells pretreated two hours prior to infection with *S. aureus*.

Figure 9:
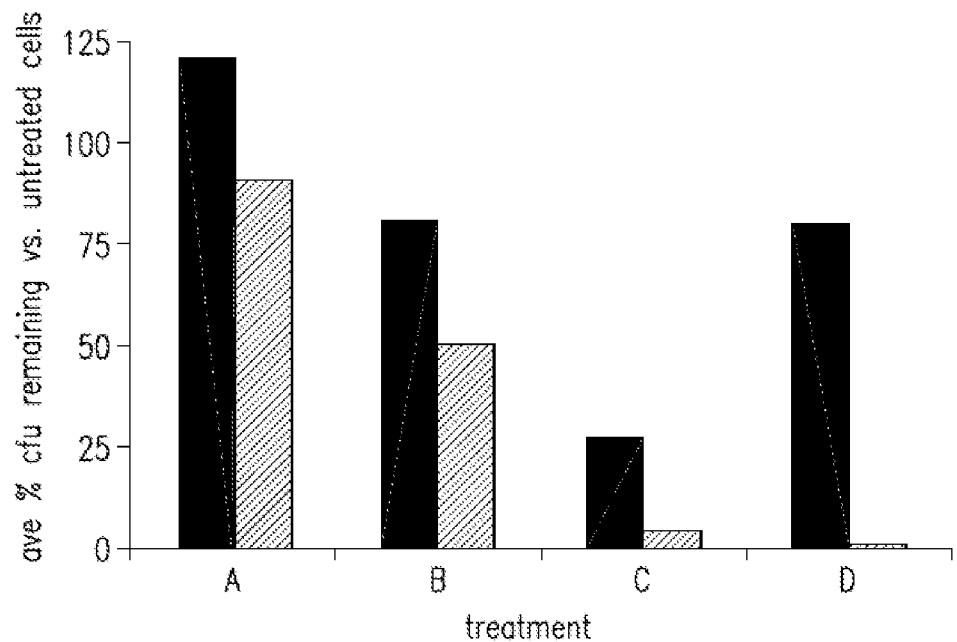
FIG. 9 depicts the average percent surviving bacteria in treated vs. untreated HaCaT cells infected with two strains of S. aureus, Newman (hatched bars) or MRSA (black bars) and pre-treated for 1 hour with either DMSO (control), 800 µM mimosine, 10 µM a compound disclosed in Table VIII or 1 µg/mL vancomycin. Data shown is 2 hours post-treatment.
Figure 10:
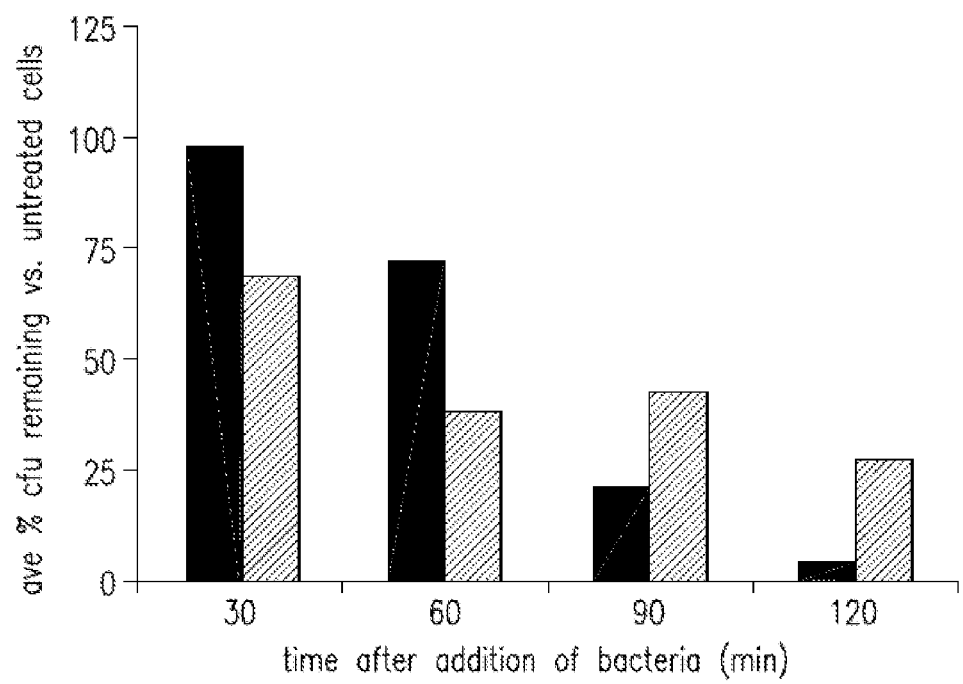
FIG. 10 depicts the average percent surviving bacteria in treated vs. untreated HaCaT cells infected with two strains of S. aureus, Newman (hatched bars) or MRSA (black bars), following pre-treatment with 10 µM a compound disclosed in Table VIII.

FIG. 9 depicts the average percent of colony forming units present at 120 minutes post-infection vs DMSO (control) when HaCaT cells are pre-treated for 1 hour according to the examples above with 800 µM mimosine, 10 µM of compound disclosed in Table VIII or 1 µg mL vancomycin followed by inoculation with *S. aureus* (Newman strain, hatched bars) and methicillin-resistant *S. aureus* (MRSA, black bars). FIG. 10 depicts the average percent of colony forming units present at 30, 60, 90, and 120 minutes post-infection for Newman strain of *S. aureus* (hatched bars) and MRSA (black bars) when HaCaT cells are pre-treated for 1 hour according to the examples above with 10 µM of a compound disclosed in Table VIII.

Figure 11:
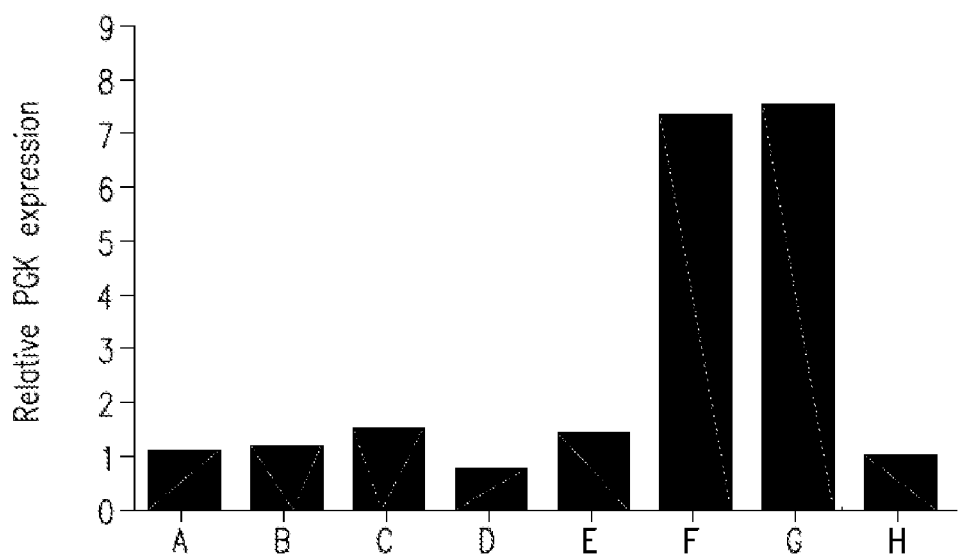
FIG. 11 depicts the up regulation of phosphoglycerate kinase (PGK) expression in wild type murine embryonic fibroblasts as a result of treatment with a compound disclosed in Table VIII at dosages of 1 µM (E), 10 µM (F), and 50 µM (G) vs. wild type control (H) and the lack of up regulation of PGK expression in HIF-1 knock out cells as a result of treatment with a compound disclosed in Table VIII at dosages of 1 µM (A), 10 µM (B), and 50 µM (C) and HIF-1 knock out control (D). Both cell types were treated for 7 hours.

FIG. 11 depicts the up regulation of phosphoglycerate kinase (PGK) expression in wild type murine embryonic fibroblasts as a result of treatment with compound a compound disclosed in Table VIII at dosages of 1 µM (E), 10 µM (F), and 50 µM (G) vs. wild type control (H) and the lack of up regulation of PGK expression in HIF-1 knock out cells as a result of treatment with a compound disclosed in Table VIII at dosages of 1 µM (A), 10 µM (B), and 50 µM (C) and HIF-1 knock out control (D). Both cell types were treated for 7 hours.

Figure 12:
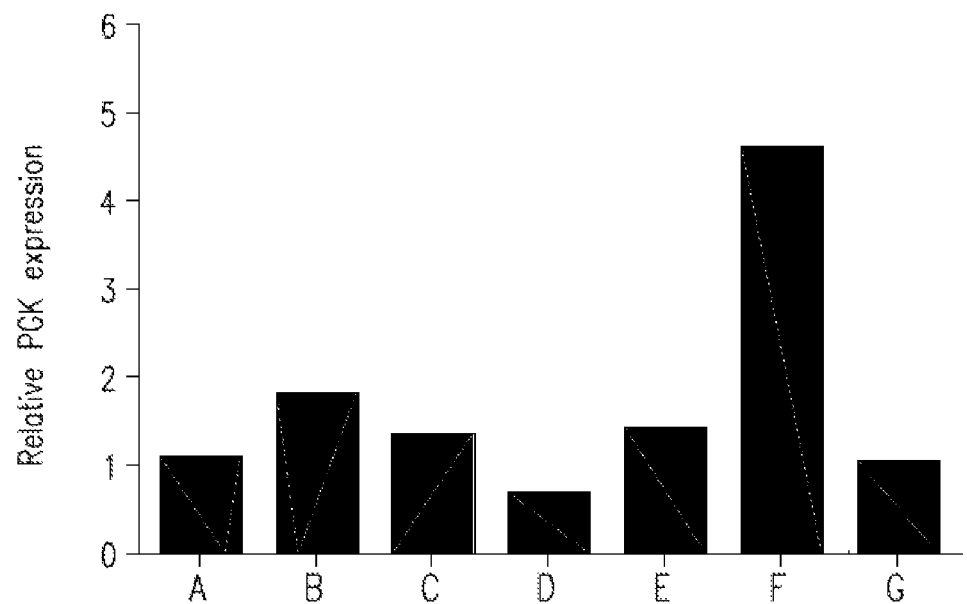
FIG. 12 depicts the up regulation of phosphoglycerate kinase (PGK) expression in wild type murine embryonic fibroblasts as a result of treatment with compound 1-(3-Chlorobenzyl)-3-hydroxypyridin-2(1H)-one at dosages of 1 µM (E), 10 µM (F), vs. wild type control (G) and the lack of up regulation of PGK expression in HIF-1 knock out cells as a result of treatment with a compound disclosed in Table VIII at dosages of 1 µM (A), 10 µM (B), and 50 µM (C) and HIF-1 knock out control (D).

FIG. 12 depicts the up regulation of phosphoglycerate kinase (PGK) expression in wild type murine embryonic fibroblasts as a result of treatment with a compound disclosed in Table VIII at dosages of 1 µM (E), 10 µM (F), vs. wild type control (G) and the lack of up regulation of PGK expression in HIF-1 knock out cells as a result of treatment with a compound disclosed in Table VIII at dosages of 1 µM (A), 10 µM (B), and 50 µM (C) and HIF-1 knock out control (D).

Figure 13:
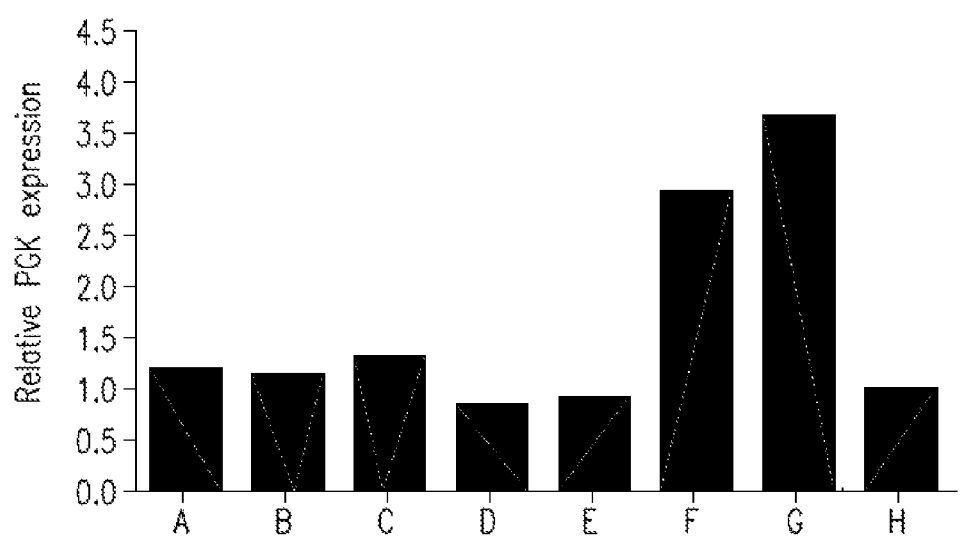
FIG. 13 depicts the up regulation of phosphoglycerate kinase (PGK) expression in wild type murine embryonic fibroblasts as a result of treatment with compound a compound disclosed in Table VIII at dosages of 1 µM (E), 10 µM (F), and 50 µM (G) vs. wild type control (H) and the lack of up regulation of PGK expression in HIF-1 knock out cells as a result of treatment with compound a compound disclosed in Table VIII at dosages of 1 µM (A), 10 µM (B), and 50 µM (C) and HIF-1 knock out control (D).

FIG. 13 depicts the up regulation of phosphoglycerate kinase (PGK) expression in wild type murine embryonic fibroblasts as a result of treatment with a compound disclosed in Table VIII at dosages of 1 µM (E), 10 µM (F), and 50 µM (G) vs. wild type control (H) and the lack of up regulation of PGK expression in HIF-1 knock out cells as a result of treatment with a compound disclosed in Table VIII at dosages of 1 µM (A), 10 µM (B), and 50 µM (C) and HIF-1 knock out control (D).

Figure 14:
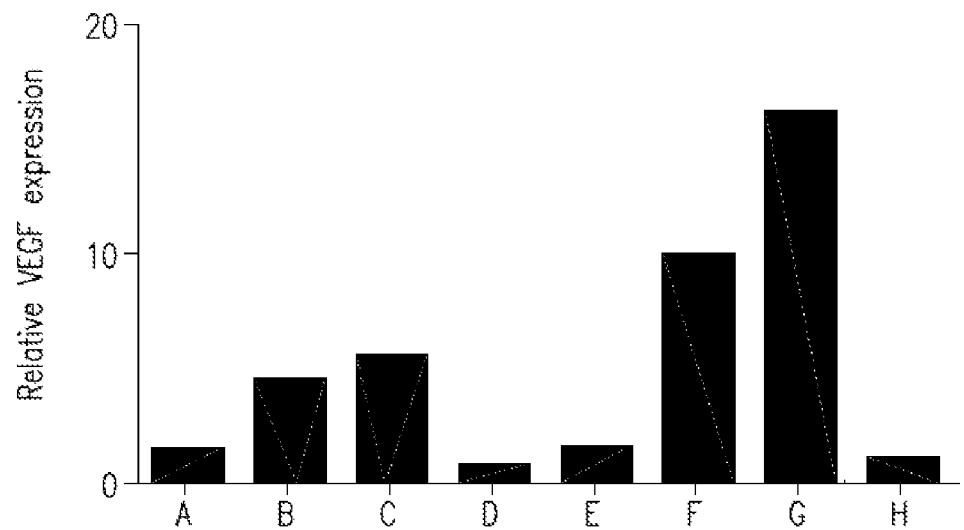
FIG. 14 depicts the up regulation of vascular endothelia growth factor (VEGF) expression in wild type murine embryonic fibroblasts as a result of treatment with compound a compound disclosed in Table VIII at dosages of 1 µM (E), 10 µM (F), and 50 µM (G) vs. control (H) and the lack of up regulation of VEGF expression in HIF-1 knock out cells treated with a compound disclosed in Table VIII at dosages of 1 µM (A), 10 µM (B), and 50 µM (C) and HIF-1 knock out control (D). Both cell types were treated for 7 hours.

Vascular Endothelial Growth Factor (VEGF) is dependent upon the presence of HIF-1 in cells. FIG. 14 depicts the up regulation of vascular endothelia growth factor (VEGF) expression in wild type murine embryonic fibroblasts as a result of treatment with a compound disclosed in Table VIII at dosages of 1 µM (E), 10 µM (F), and 50 µM (G) vs. control (H) and the lack of up regulation of VEGF expression in HIF-1 knock out cells treated with compound a compound disclosed in Table VIII at dosages of 1 µM (A), 10 µM (B), and 50 µM (C) and HIF-1 knock out control (D). Both cell types were treated for 7 hours. As seen in FIG. 14, VEGF is increased when dosed at 10 µM (F) and 50 µM (G). In HIF-1 knock out cells, there is no increase in PGK up regulation when HIF-1 knock out cells are dosed at 1 µM (A), 10 µM (B), and 50 µM (C) when compared to wild type control (H) and HIF-1 knock out control (D).

Wound Healing

EXAMPLE 11

Twenty-four (24) mice were divided into three groups. Group 2 animals were administered bacterial inoculum (*Staphylococcus aureus* antibiotic sensitive Newman strain

[ATCC #25904]) by subcutaneous injection on Day 0 and received 10 µM of a compound disclosed in Table VIII for 6 days starting at 2 hours post-infection (Days 0-5). Group 1 received subcutaneous injections of DMSO. Group 3 served as a control group and received no treatment. Lesion size was monitored daily during the study. Only open wounds were considered lesions; bumps and white patches without an open wound were not measured for lesion size. On Day 7, the final lesion size was measured and mice were sacrificed for determination of bacterial load in skin and kidney. Day 7 post-infection, mice were sacrificed after final lesion size measurement and the lesioned skin tissue and both kidneys were collected. Skin and kidneys were homogenized in phosphate buffered saline, serially diluted, and plated on Todd-Hewitt agar plates to enumerate colony forming units of bacteria.

Figure 15:
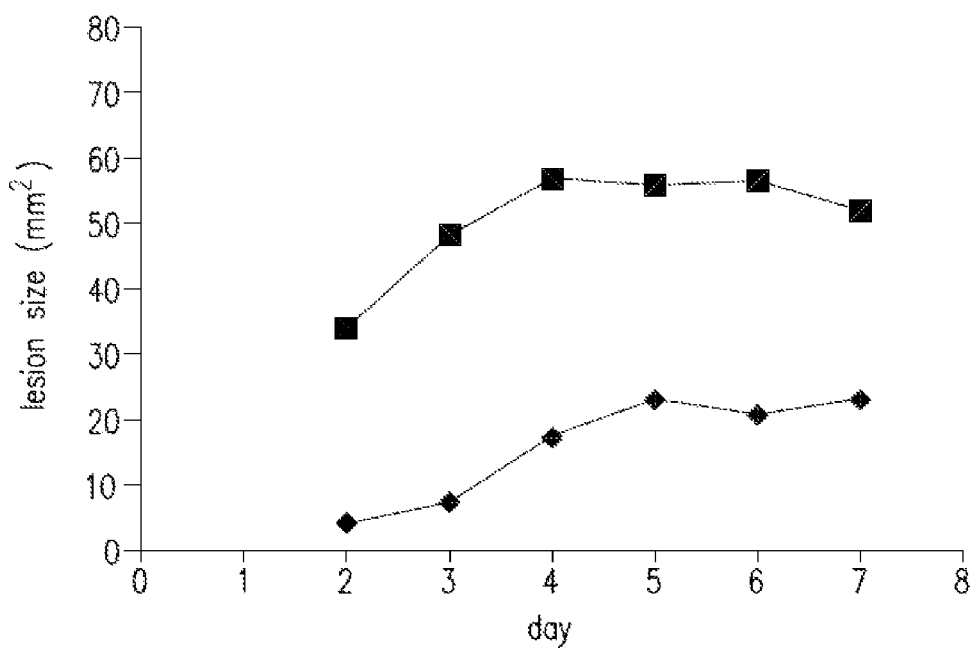
FIG. 15 depicts the results of Example 11 wherein 3 groups of animals are treated with Staphylococcus aureus antibiotic sensitive Newman strain. The data show the significant reduction in the size of skin lesions (wounds) for animals in Group 1 (solid circles (●)) treated with 10 µM of a compound disclosed in Table VIII versus animal given a bolus of DMSO (solid squares (■)).

FIG. 15 shows the significant reduction in the size of skin lesions (wounds) for animals in Group 1 (solid circles (●)) treated with 10 µM of a compound disclosed in Table VIII versus animal treated with DMSO (solid squares (■)). As depicted in FIG. 15, mice infected with Newman strain of *S. aureus* followed by treatment with 10 µM of a compound disclosed in Table VIII or DMSO (control) at 2 hours post-infection. The data show the statistically significant reduction in the size of skin lesions (wounds) for animals treated with a compound disclosed in Table VIII (solid circles (●)) or DMSO (solid squares (■)).

Figure 16:
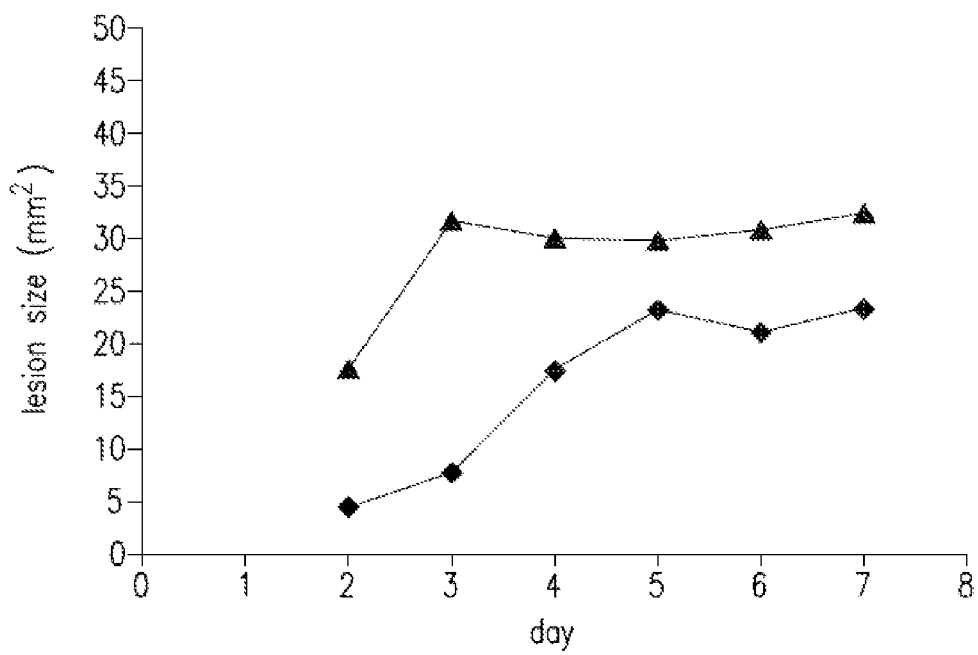
FIG. 16 also depicts the results of Example 11 showing the reduction in the size of skin lesions (wounds) for animals in Group 1 (solid circles (●)) treated with 10 µM a compound disclosed in Table VIII versus animals that are untreated (solid triangles (▲)).

FIG. 16 shows the significant reduction in the size of skin lesions (wounds) for animals in Group 1 (solid circles (●)) treated with 10 µM of a compound disclosed in Table VIII versus untreated animals (solid triangles (▲)). As depicted in FIG. 16, mice infected with Newman strain of *S. aureus* followed by treatment with 10 µM of a compound disclosed in Table VIII or no treatment at 2 hours post-infection. The data show the reduction in the size of skin lesions (wounds) for animals treated with a compound disclosed in Table VIII (solid circles (●)) or untreated (solid triangles (▲)).

EXAMPLE 12

Twenty-four (24) mice were divided into three groups. Group 1 animals were administered bacterial inoculum (*Staphylococcus aureus* antibiotic sensitive Newman strain [ATCC #25904]) by subcutaneous injection on Day 0 and received 10 µM of a compound disclosed in Table VIII for 6 days starting at 2 hours post-infection (Days 0-5). Group 2 received subcutaneous injections of DMSO. Group 3 served as a control group and received no treatment. Lesion size was monitored daily during the study. Only open wounds were considered lesions; bumps and white patches without an open wound were not measured for lesion size. Day 7 post-infection, mice were sacrificed after final lesion size measurement and lesioned skin tissue and both kidneys were collected. Skin and kidneys were homogenized in phosphate buffered saline, serially diluted, and plated on Todd-Hewitt agar plates to enumerate colony forming units of bacteria.

Figure 17:
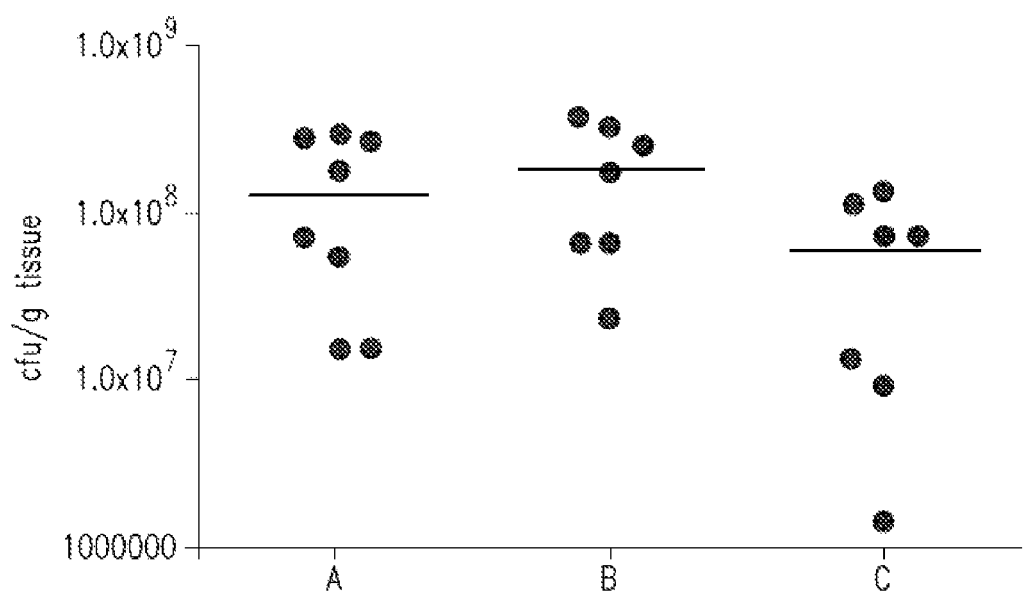
FIG. 17 is a plot histogram that depicts the results of Example 12 wherein 3 groups of animals are treated with *Staphylococcus aureus* antibiotic sensitive Newman strain [ATCC #25904]. The data show the results for the untreated group plotted under (A), the results for the group treated with DMSO plotted under (B) and results for the group treated with 10 µM of a compound disclosed in Table VIII plotted under (C).

FIG. 17 is a plot histogram wherein the number of observed colony forming units per gram of skin tissue is depicted. The straight lines indicate the mean value for each group. The results for the untreated group are plotted under (A), the results for the group treated with DMSO are plotted under (B) and results for the group treated with 10 µM of a compound disclosed in Table VIII are plotted under (C).

Figure 18:
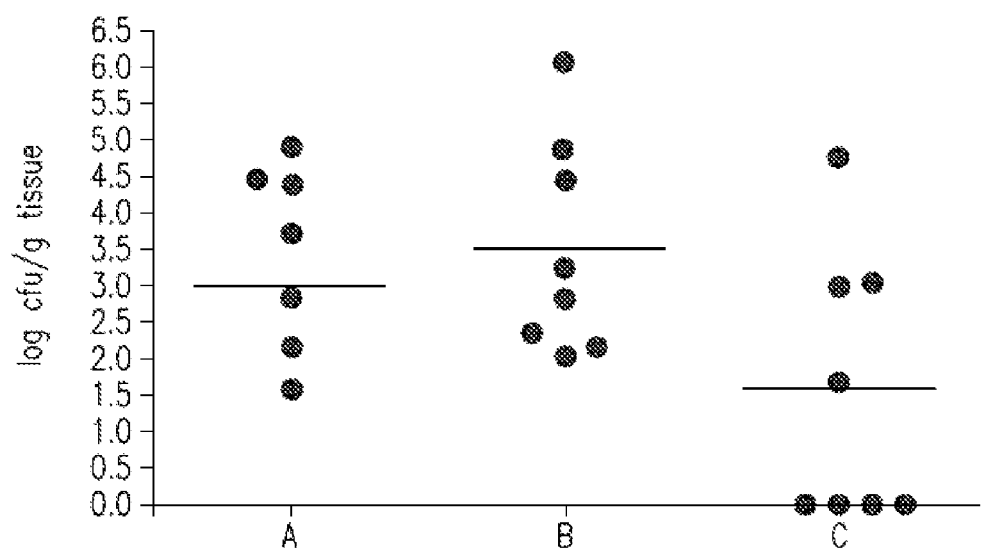
FIG. 18 also depicts the results of Example 12 wherein the number of colony forming units in the kidney are plotted for the various groups: the untreated group is plotted under (A), the group treated with DMSO is plotted under (B) and the group treated with 10 µM of a compound disclosed in Table VIII is plotted under (C).

FIG. 18 is a plot of the observed colony forming units of bacteria found in the kidneys of the animals. The results for the untreated group are plotted under (A), the results for the group treated with DMSO are plotted under (B) and results for the group treated with 10 µM of a compound disclosed in Table VIII are plotted under (C). As can be seen from these data, half of the animals treated with the HIF-1α prolyl hydroxylase inhibitor disclosed in Table VIII had no bacteria in the kidney indicating that the compound disclosed in Table VIII was able to systemically prevent spread of the infection from the wound to the kidney.

EXAMPLE 13

Twenty (20) mice were divided into two groups. Group 1 animals were administered bacterial inoculum (*Streptococcus pyogenes* NZ131 [M49 strain]) by subcutaneous injection on Day 0 and were pretreated with compound a compound disclosed in Table VIII once per day for 4 days, starting 2 hours pre-infection (Days 0-3). Compound a compound disclosed in Table VIII was formulated in cyclodextran and diluted in distilled water prior to subcutaneous injection, at a dose of 0.5 mg/kg. Lesion size was monitored daily during the study. Only open wounds were considered lesions; bumps and white patches without an open wound were not measured for lesion size. On Day 4 post-infection, mice were sacrificed after final lesion size measurement and lesioned skin tissue and both kidneys were collected. Skin and kidneys were homogenized in phosphate buffered saline, serially diluted, and plated on Todd-Hewitt agar plates to enumerate colony forming units of bacteria.

Figure 19:
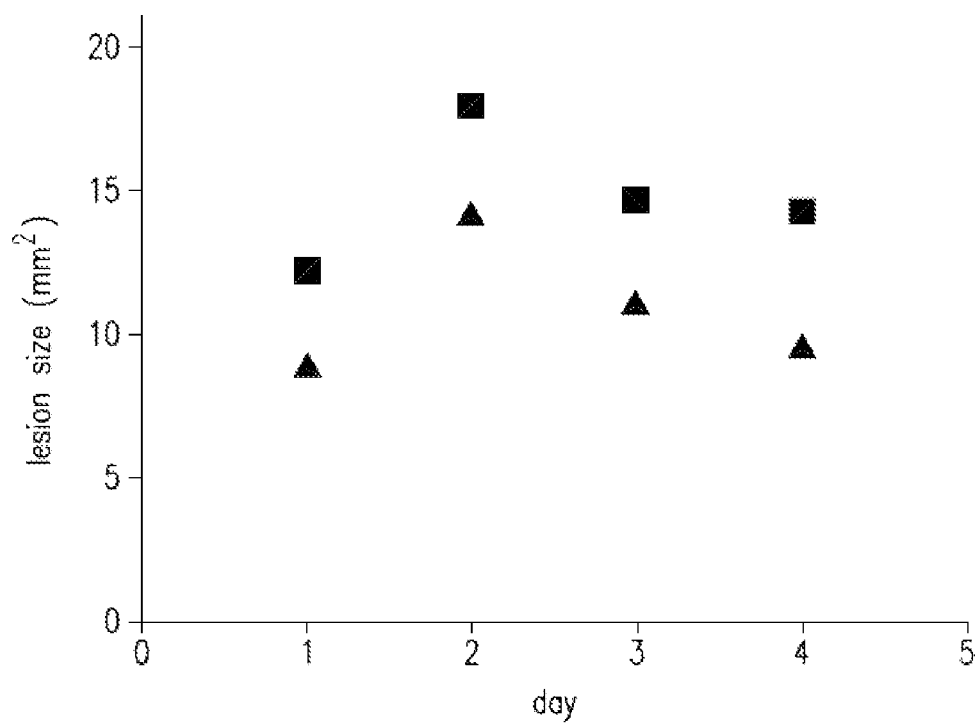
FIG. 19 depicts the results of Example 13 wherein 2 groups of animals are treated with *Streptococcus pyogenes* NZ131 [M49 strain]. The data show the reduction in the size of skin lesions (wounds) for animals in Group 1 (solid triangles (▲)) treated with 0.5 mg/kg of a compound disclosed in Table VIII versus animal treated with vehicle control (cyclodextran) (solid circles (●)).
Figure 20:
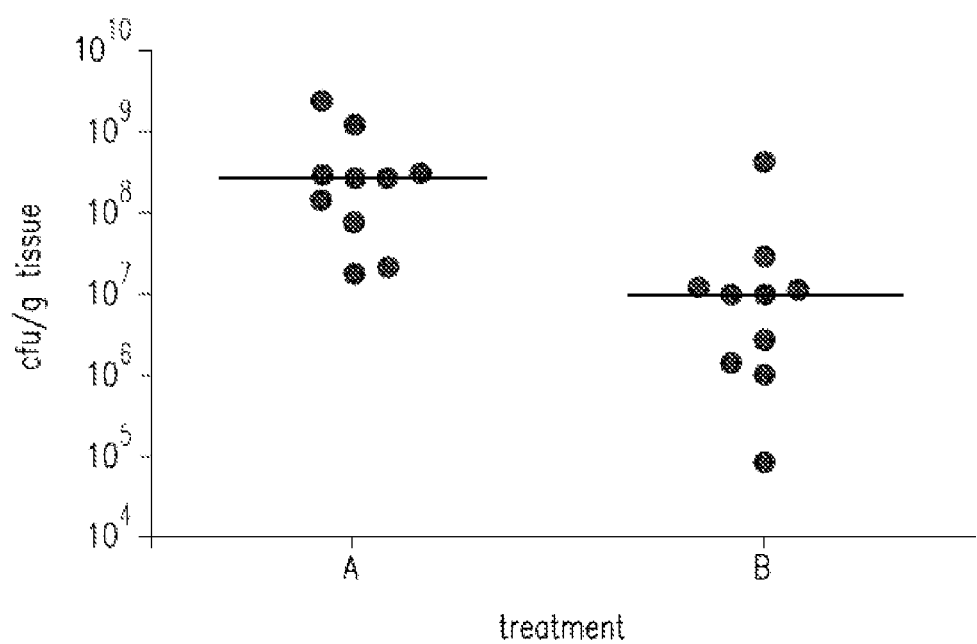
FIG. 20 is a plot histogram that also depicts the results of Example 12 wherein the number of colony forming units for the observed skin lesions on animals treated with vehicle control (cyclodextran) are plotted under (A) and results for the group treated with 0.5 mg/kg of a compound disclosed in Table VIII are plotted under (B).

FIG. 19 depicts the results of Example 13 wherein 2 groups of animals are treated with *Streptococcus pyogenes* NZ131 [M49 strain]. The data show the reduction in the size of skin lesions (wounds) for animals in Group 1 (solid triangles (▲)) treated with 0.5 mg/kg of a compound disclosed in Table VIII versus animal treated with vehicle control (cyclodextran) (solid circles (●)). FIG. 20 is a plot histogram that also depicts the results of Example 12 wherein the number of colony forming units for the observed skin lesions on animals treated with vehicle control (cyclodextran) are plotted under (A) and results for the group treated with 0.5 mg/kg of a compound disclosed in Table VIII are plotted under (B).

KITS

Also disclosed are kits comprising the HIF-1α prolyl hydroxylase inhibitors be delivered into a human, mammal, or cell. The kits can comprise one or more packaged unit doses of a composition comprising one or more HIF-1α prolyl hydroxylase inhibitors to be delivered into a human, mammal, or cell. The units dosage ampules or multidose containers, in which the HIF-1α prolyl hydroxylase inhibitors to be delivered are packaged prior to use, can comprise an hermetically sealed container enclosing an amount of polynucleotide or solution containing a substance suitable for a pharmaceutically effective dose thereof, or multiples of an effective dose. The HIF-1α prolyl hydroxylase inhibitor can be packaged as a sterile formulation, and the hermetically sealed container is designed to preserve sterility of the formulation until use.

The disclosed HIF-1α prolyl hydroxylase inhibitors can also be present in liquids, emulsions, or suspensions for delivery of active therapeutic agents in aerosol form to cavities of the body such as the nose, throat, or bronchial passages. The ratio of HIF-1α prolyl hydroxylase inhibitors to the other compounding agents in these preparations will vary as the dosage form requires.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the HIF-1α prolyl hydroxylase inhibitor in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, referenced above.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

When the HIF-1α prolyl hydroxylase inhibitors are to be delivered into a mammal other than a human, the mammal can be a non-human primate, horse, pig, rabbit, dog, sheep, goat, cow, cat, guinea pig or rodent. The terms human and mammal do not denote a particular age or sex. Thus, adult and newborn subjects, as well as fetuses, whether male or female, are intended to be covered. A patient, subject, human or mammal refers to a subject afflicted with a disease or disorder. The term "patient" includes human and veterinary subjects.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for treating a wound in a subject, comprising administering to a subject in need thereof an effective amount of a compound having the formula:

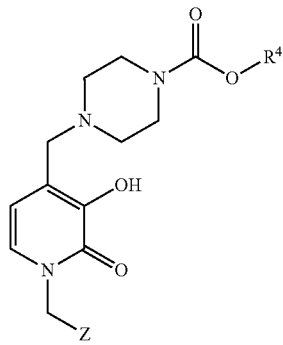

wherein wherein Z has the formula:

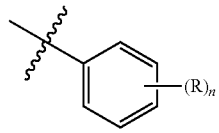

R represents a halogen, and n is an integer from 0 to 5;
$R^4$ is $C_1$-$C_4$ linear alkyl or $C_3$-$C_4$ branched alkyl;
or a pharmaceutically acceptable salt thereof.

2. The method according to claim 1, wherein $R^4$ is tert-butyl.

3. The method according to claim 1, wherein Z is 4-chlorophenyl.

4. The method according to claim 1, wherein the one or more compounds is tert-butyl 4-{[1-(4-chlorobenzyl)-3-hydroxy-2-oxo-1,2-dihydropyridin-4-yl]methyl}-piperazine-1-carboxylate or a pharmaceutically acceptable salt chosen from hydrochloride salt, hydrogen sulfate salt, sulfate salt, p-toluenesulfonyl salt, methansulfonyl salt and mixtures thereof.

5. The method according to claim 1, wherein the wound is infected with methicillin resistant *Staphylococcus aureus*.

6. The method according to claim 1, wherein the wound is infected with bacteria.

7. The method according to claim 6, wherein the compound is co-administered with an antimicrobial.

8. A method for treating peripheral vascular disease in a subject in need thereof, comprising administering to a subject in need thereof an effective amount of a HIF-1α prolyl hydroxylase inhibitor having the formula:

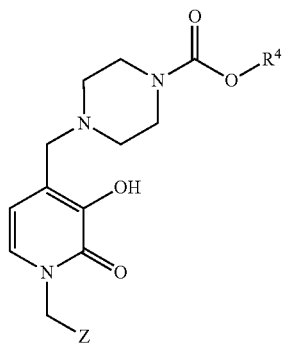

wherein Z has the formula:

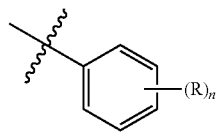

R represents a halogen, and n is an integer from 0 to 5;
$R^4$ is $C_1$-$C_4$ linear alkyl or $C_3$-$C_4$ branched alkyl;
or a pharmaceutically acceptable salt thereof.

9. The method according to claim 8, wherein the compound is tert-butyl 4-{[1-(4-chlorobenzyl)-3-hydroxy-2-oxo-1,2-dihydropyridin-4-yl]methyl}-piperazine-1-carboxylate or a pharmaceutically acceptable salt chosen from hydrochloride salt, hydrogen sulfate salt, sulfate salt, p-toluenesulfonyl salt, methansulfonyl salt and mixtures.

10. A method for up regulation of phosphoglycerate kinase (PGK) in a subject in need thereof, comprising administering to the subject in need thereof a compound of the formula:

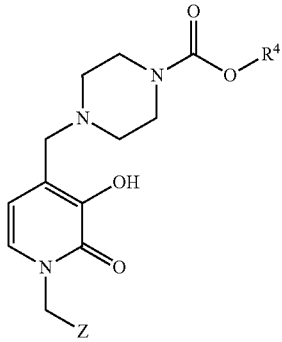

wherein Z has the formula:

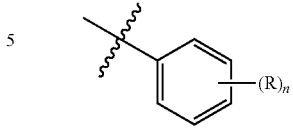

R represents a halogen, and n is an integer from 0 to 5; $R^4$ is $C_1$-$C_4$ linear alkyl or $C_3$-$C_4$ branched alkyl; or a pharmaceutically acceptable salt thereof.

11. The method according to claim 10, wherein $R^4$ is tert-butyl.

12. The method according to claim 10, wherein Z is 4-chlorophenyl.

13. The method according to claim 10, wherein the one or more compounds is tert-butyl4-{[1-(4-chlorobenzyl)-3-hydroxy-2-oxo-1,2-dihydropyridin-4-yl]methyl}-piperazine-1-carboxylate or a pharmaceutically acceptable salt chosen from hydrochloride salt, hydrogen sulfate salt, sulfate salt, p-toluenesulfonyl salt, methansulfonyl salt and mixtures thereof.

* * * * *